United States Patent [19]

Delaney et al.

[11] Patent Number: 5,496,805
[45] Date of Patent: Mar. 5, 1996

[54] INHIBITORS OF NEUTRAL ENDOPEPTIDASE

[75] Inventors: Norma G. Delaney, Princeton; Eric M. Gordon, Pennington, both of N.J.; Jack M. DeForrest, Wycombe, Pa.; David W. Cushman, West Windsor, N.J.

[73] Assignee: E. R. Squibb & Sons, Inc., Princeton, N.J.

[21] Appl. No.: 554,976

[22] Filed: Jul. 12, 1990

Related U.S. Application Data

[63] Continuation of Ser. No. 59,072, Jun. 8, 1987, abandoned.

[51] Int. Cl.⁶ .................................................. A61A 38/05
[52] U.S. Cl. .................................. 514/19; 514/7; 514/11; 514/21; 540/463; 540/524; 540/531
[58] Field of Search ................................. 514/19, 21, 11, 514/7; 540/463, 531, 524

[56] References Cited

U.S. PATENT DOCUMENTS

| | | | |
|---|---|---|---|
| 4,053,651 | 10/1977 | Ondetti et al. | 424/319 |
| 4,105,789 | 8/1978 | Ondetti et al. | 424/309 |
| 4,235,885 | 11/1980 | Sundeen et al. | 424/177 |
| 4,316,896 | 2/1982 | Thorsett et al. | 424/200 |
| 4,339,600 | 7/1982 | Ondetti et al. | 562/426 |
| 4,374,829 | 2/1983 | Harris et al. | 514/21 |
| 4,379,146 | 4/1983 | Greenlee et al. | 514/7 |
| 4,382,081 | 5/1983 | Sundeen et al. | 424/177 |
| 4,401,677 | 8/1983 | Greenberg et al. | 424/317 |
| 4,409,146 | 10/1983 | Thorsett et al. | 540/531 |
| 4,423,242 | 12/1983 | Wilkinson et al. | 560/41 |
| 4,432,972 | 2/1984 | Karanewsky et al. | 424/177 |
| 4,452,791 | 6/1984 | Ryono et al. | 424/200 |
| 4,495,176 | 1/1985 | Brule et al. | 514/7 |
| 4,499,079 | 2/1985 | Gordon et al. | 514/2 |
| 4,508,712 | 4/1985 | Needleman | 514/11 |
| 4,587,238 | 5/1986 | Harris et al. | 540/463 |
| 4,629,787 | 12/1986 | Harris et al. | 540/524 |
| 4,722,810 | 2/1988 | Delaney et al. | 260/402.5 |

FOREIGN PATENT DOCUMENTS

| | | |
|---|---|---|
| 537592 | 10/1980 | Australia. |
| 117429 | 9/1984 | European Pat. Off.. |
| 136883 | 4/1985 | European Pat. Off.. |
| 161789 | 11/1985 | European Pat. Off.. |
| 225292 | 6/1987 | European Pat. Off.. |
| 274234 | 7/1988 | European Pat. Off.. |
| 2194438 | 3/1988 | United Kingdom. |
| 8600066 | 1/1986 | WIPO. |

OTHER PUBLICATIONS

Cushman, Do Wo, et al., "Angiotensin–Converting Enzyme Inhibitors", *Enzyme Inhibitors as Drugs*, pp. 231–247, 1980.
Materson, "Advances in the Management of Hypertension: ACE Inhibitor Therapy", Cardiovascular Medicine, vol. 7, No. 9, Sep. 1986, pp. 175–191.
Vidt et al., "Captopril", The New England Journal of Medicine, vol. 306, No. 4, pp. 214–218 (1982).
Physician's Desk Reference, 1989 Edition, pp. 1408–1410 and 2080–2085.
Marsh et al., "Renal and Blood Pressure Response to Synthetic Atrial Natriuretic Factor . . . ", Hypertension, vol. 7, No. 3, 1985, pp. 386–391.
Seymour et al., "Synthetic Atrial Natriuretic Factor In Conscious Normotensive and Hypertensive Rats", Supp 1 Hypertension, vol. 7, No. 3, 1985, pp. I–35 to I–42.
Cushman et al., "Design of Potent Competitive Inhibitors . . . ", Biochemistry, vol. 16, No. 25, pp. 5484–5491 (1977).
Mumford et al., "Inhibition of Porcine Kidney Enkephalinase . . . ", Biochem & Biophys. Res. Comm., vol. 109, No. 4, pp. 1303–1309 (1982).
Elliott et al., "Synthesis and Biological Evaluation . . . " J. Med. Chem., vol. 28, pp. 1208–1216 (1985).
International Dictionary of Medicine And Biology, pp. 158, 163, 847, 1876 (1986).

*Primary Examiner*—Howard E. Schain
*Attorney, Agent, or Firm*—Stephen B. Davis

[57] ABSTRACT

Diuresis, natriuresis, and the lowering of blood pressure are produced in a host by administering one or more neutral endopeptidase inhibitors. An additional blood pressure lowering agent such as an angiotensin converting enzyme inhibitor can be administered along with the neutral endopeptidase inhibitor.

10 Claims, No Drawings

INHIBITORS OF NEUTRAL ENDOPEPTIDASE

This is a continuation of application Ser. No. 059,072, filed on Jun. 8, 1987, now abandoned.

BACKGROUND OF THE INVENTION

Mercaptoalkanoyl and acylmercaptoalkanoyl α-amino acids are disclosed as anti-hypertensive agents due to their angiotensin converting enzyme inhibition activity by Ondetti et al. in U.S. Pat. No. 4,053,651.

Cushman et al. (Biochemistry, Vol. 16, No. 25, 1977, p. 5484–5491) disclose various carboxyalkanoyl and mercaptoalkanoyl amino acids including

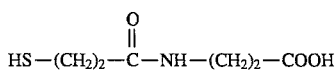

as angiotensin converting enzyme inhibitors.

Greenberg et al. in U.S. Pat. No. 4,401,677 disclose that various mercaptoalkanoyl α-amino acids are useful analgesic agents due to their enkephalinase inhibition activity.

Sundeen et al. in U.S. Pat. No. 4,235,885 and 4,382,081 disclose that certain mercaptoalkanoyl and acylmercaptoalkanoyl amino acids inhibit mammalian collagenase and are thus useful in treating rheumatoid arthritis.

Delaney et al. in European Patent Application 136,883 disclose that mercaptoalkanoyl and acylmercaptoalkanoyl amino acids are useful analgesic agents due to their enkephalinase inhibition activity.

Roques et al. (Nature, Vol. 288, Nov. 1980, p. 286–288) disclose that thiorphan, [(D,L)-3- mercapto-2-benzylpropanol]glycine, is an inhibitor of enkephalinase in vitro in nanomolar concentrations and in vivo after either intracerebroventricular or systemic administration.

Roques et al. [Proc. Natl. Acad. Sci (U.S.A.) Vol. 80, 1983, p. 3178–3182]disclose thiorphan and its retro-inverso isomer, and their activity as inhibitors of enkephalinase.

Roques et al. in U.S. Pat. No. 4,513,009 disclose various α-amino acid derivatives including mercaptoalkanoyl and acylmercaptoalkanoyl derivatives as possessing enkephalinase inhibition activity.

Delaney et al. in European Patent Application 161,769 disclose mercapto and acylmercapto enkephalinase inhibitors of the formula

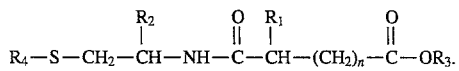

Weller et al. in U.S. Pat. No. 4,560,506 disclose that mercaptocycloalkanoyl, acylmercaptocycloalkanoyl, mercaptoarylcarbonyl, and acylmercaptoarylcarbonyl dipeptides possess angiotensin converting enzyme inhibition activity and depending upon the terminal amino acid may also possess enkephalinase inhibition activity.

Ondetti et al. Australian Patent 537,592 disclose mercaptoalkanoyl and acylmercaptoalkanoyl dipeptides possessing angiotensin converting enzyme inhibition activity.

Gordon et al. in U.S. Pat. No. 4,499,079 disclose that carboxycycloalkylcarbonyl dipeptides possess angiotensin converting enzyme inhibition activity and depending upon the terminal amino acid may also possess enkephalinase inhibition activity.

Berger in U.S. Pat. No. 4,610,816 disclose that carboxyalkyl dipeptides possess enkephalinase inhibition activity.

Mumford et al. (Biochemical and Biophysical Research Comm., Vol. 109, No. 4, 1982, p. 1303–1309) disclose that various substituted N-carboxymethyl dipeptides including those having a terminal β-alanine group possess enkephalinase inhibition activity.

Ksander in PCT Application WO 86/00066 disclose that various carboxyacyl amino acids possess enkephalinase inhibition activity.

Thorsett et al. in U.S. Pat. No. 4,316,896 disclose that phosphoramides including the dipeptides of the formula

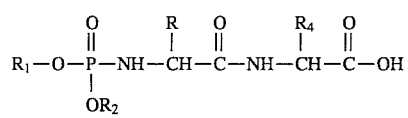

possess angiotensin converting enzyme inhibition activity.

Karanewsky et al. in U.S. Pat. No. 4,432,972 disclose that phosphonamidates including the dipeptides of the formula

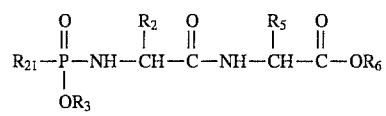

possess angiotensin converting enzyme and enkephalinase inhibition activity.

Karanewsky et al. in U.S. Pat. No. 4,616,005 disclose phosphonate substituted amino acids of the formula

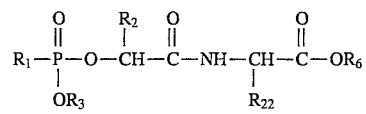

possess angiotensin converting enzyme inhibition activity.

Gaeta in European Patent Application 117,429 disclose phosphorus containing enkephalinase inhibitors of the formula

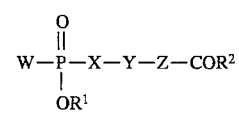

wherein W is $R^1$ or $OR^1$, X is $-(CH_2)_p-CHR^3$ or $-CHR^3-(CH_2)_p-$, Y is

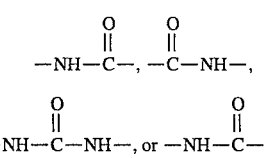

and Z includes $-(CHR^4)_r-$.

Wilkinson et al. in U.S. Pat. No. 4,423,242 disclose enkephalinase inhibitors of the formula

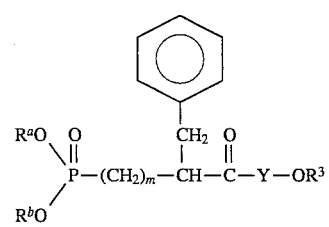

wherein Y is

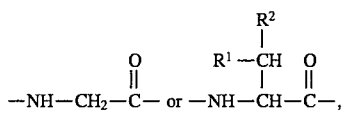

and $R^a$ and $R^b$ are independently selected from hydrogen, alkali metal salt ion, or alkyl.

Ryono et al. in U.S. Pat. No. 4,452,791 disclose angiotensin converting enzyme inhibitors including those of the formula

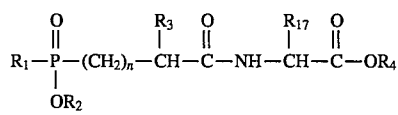

wherein n is zero or one, $R_1$ is alkyl, aryl, aralkyl, etc., and $R_3$ is $-(CH_2)_m-NH_2$,

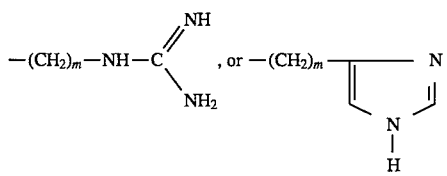

wherein m is zero or an integer from 1 to 5.

Roques et al. in U.S. Pat. No. 4,618,708 disclose enkephalinase inhibitors including those of the formulas

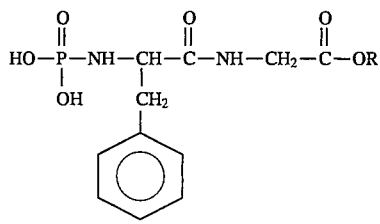

and

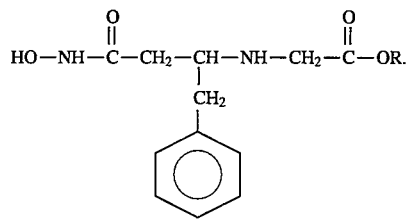

Ondetti et al. in U.S. Pat. No. 4,105,789 disclose hydroxamic acid amino acids of the formula

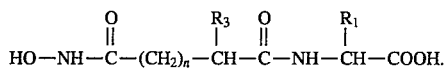

Wilkinson et al. in U.S. Pat. No. 4,504,492 disclose enkephalinase inhibiting hydroxamic acids of the formula

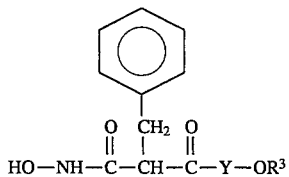

wherein Y is

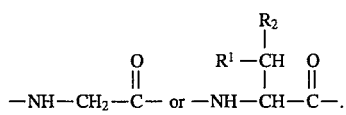

Ura et al. (Kidney International, Vol. 29, No. 1) disclose that phosphoramidon caused changes in kidney function including decreased urinary kininase activity, increased excretion of kinins, increased urine volume, and increased sodium excretion. These actions are attributed to the ability of phosphoramidon to block the degradation of intrarenally generated kinins through the inhibition of neutral endopeptidase.

Elliott et al. (Journal of Medicinal Chemistry, Vol. 28, p 1208–1216, 1985) disclose the enkephalinase and angiotensin converting enzyme inhibition activity of various phosphonamidate dipeptides.

Stephenson et al. (Biochem. J., Vol. 243, p. 183–187) disclose that the hydrolysis of α-human atrial natriuretic peptide by pig kidney microvillar membranes in vitro was suppressed by phosphoramidon.

SUMMARY OF THE INVENTION

Human as well as other mammalian atria contain specific granules which have been found to contain a precursor to a family of peptides collectively called atrial natriuretic factor (deBold, Science, Vol. 230, p. 767–770, 1985). The biologically active segments of this precursor which circulate in the blood are 21–28 amino acid peptides called atrial natriuretic peptides. These peptides cause diuresis, natriuresis, and relaxation of smooth muscle in blood vessels and other tissues (Needleman et al., Hypertension, Vol. 7, p. 469–482, 1985). The putative circulating hormone in man is a 28 amino acid peptide called human ANF 99–126. Exogenous administration of this peptide to man has been reported to cause diuresis, natriuresis, and a fall in blood pressure (Richards et al., Hypertension, Vol. 7, p 812–817, 1985).

Neutral endopeptidase (EC 3.4.24.11) is a membrane-bound metalloendopeptidase found in many tissues including the brain and kidney. Brain endopeptidase has often been referred to as "enkephalinase" due to its role in the degradation of enkephalins. Kidney neutral endopeptidase has been reported to hydrolyze peptide bonds which are on the amino terminal side of hydrophobic amino acids (Matsas et al., The Biochemical Journal, Vol. 223, p. 433–440, 1984).

This invention is directed to the method of producing diuresis, natriuresis, and blood pressure reduction in a mammalian host such as man by administering an effective amount of a neutral endopeptidase inhibitor. The inhibition of the neutral endopeptidase results in reduced inactivation of endogenous or exogenously administered human ANF 99–126 thereby producing the desired biological effect.

DETAILED DESCRIPTION OF THE INVENTION

Numerous classes of compounds are known to be endopeptidase inhibitors. Among the classes of compounds which have been found to possess neutral endopeptidase inhibition activity and thus are useful within the method of this invention are mercapto and acylmercapto amino acids and dipeptides of the formulas

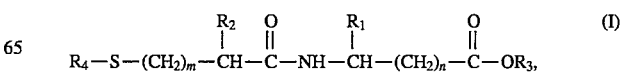 (I)

-continued

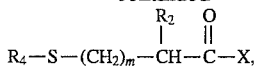 (II)

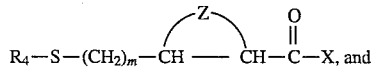 (III)

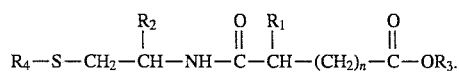

X is 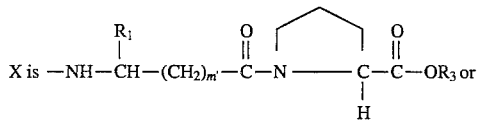 or

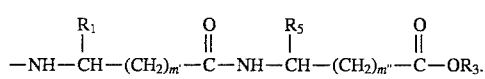

$R_4$ is hydrogen or

Z completes a cycloalkyl ring of 4 to 7 carbons.

m, m' and m" are independently selected from zero and one.

$R_1$, $R_2$ and $R_5$ are independently selected from hydrogen, lower alkyl,

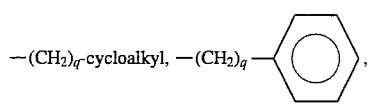

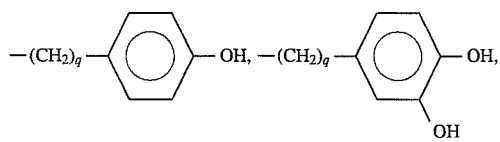

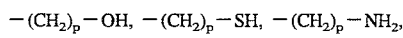

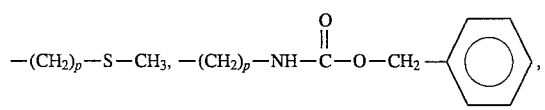

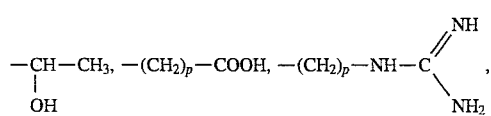

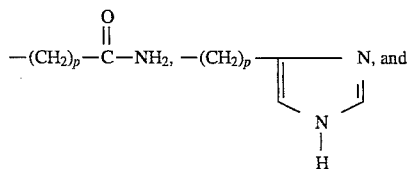

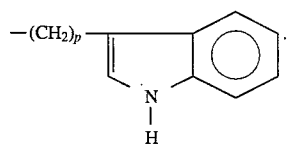

q is zero or an integer from 1 to 4.
p is an integer from 1 to 4.
n is zero or an integer from 1 to 15.

$R_3$ is hydrogen, lower alkyl, benzyl, benzhydryl, or a pharmaceutically acceptable salt forming ion.

$R_6$ is lower alkyl,

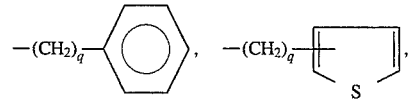

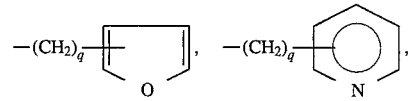

or $-(CH_2)_q$-cycloalkyl.

The carboxyacyl and carboxyalkyl compounds of the following formulas also inhibit neutral endopeptidase and are thus also useful within the method of this invention.

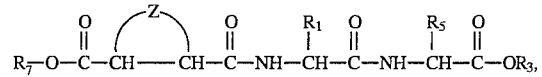 (V)

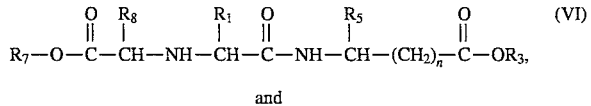 (VI)

and

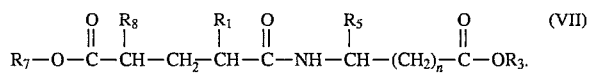 (VII)

$R_1$, $R_3$, $R_5$, Z and n are as defined above.

$R_7$ is hydrogen, lower alkyl, benzyl, benzhydryl, or a pharmaceutically acceptable salt forming ion.

$R_8$ is hydrogen, lower alkyl,

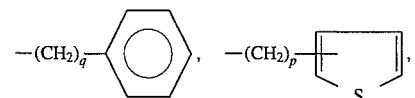

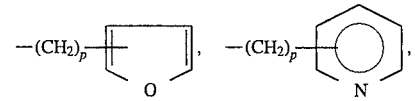

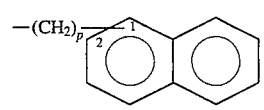

or a 1- or 2-naphthylalkylene of the formula

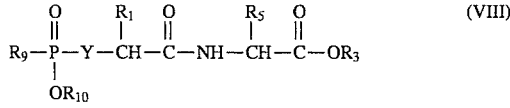

wherein p and q are as defined above.

The phosphorus containing compounds of the following formulas also inhibit neutral endopeptidase and are thus also useful within the method of this invention.

$$R_9-\overset{O}{\underset{OR_{10}}{\overset{\|}{P}}}-Y-\overset{R_1}{\underset{}{\overset{|}{C}H}}-\overset{O}{\overset{\|}{C}}-NH-\overset{R_5}{\underset{}{\overset{|}{C}H}}-\overset{O}{\overset{\|}{C}}-OR_3 \quad (VIII)$$

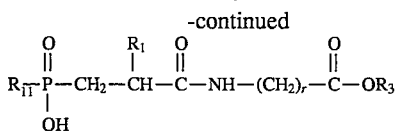

$R_1$, $R_3$ and $R_5$ are as defined above.
r is an integer from 2 to 4.
Y is -NH, -CH$_2$ or -O.
$R_9$ is lower alkyl,

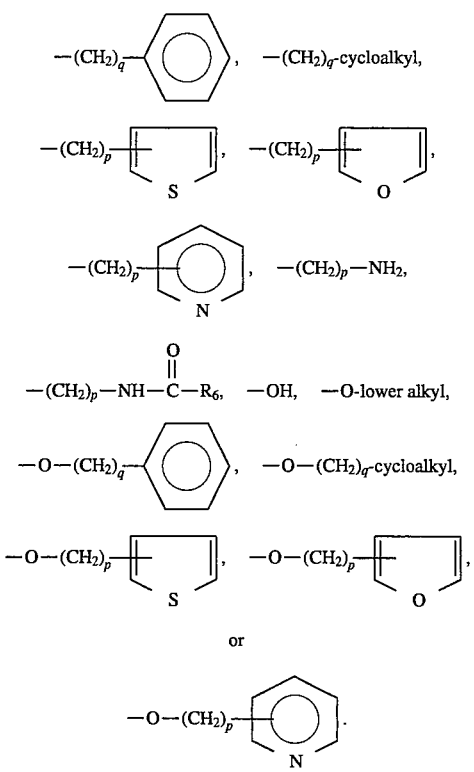

$R_{10}$ is hydrogen, lower alkyl, benzyl, benzhydryl, or a pharmaceutically acceptable salt forming ion.
$R_{11}$ is lower alkyl,

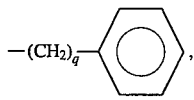

hydroxy, -O-lower alkyl,

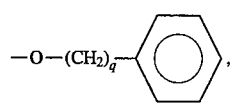

-(CH$_2$)$_q$-cycloalkyl, or -O-(CH$_2$)$_q$-cycloalkyl.

It has also been found that phosphoramidon, N-($\alpha$-L-rhamnopyranosyloxyhydroxyphosphinyl)-L-leucyl-L-tryptophan, inhibits neutral endopeptidase and is thus also useful within the method of this invention.

The hydroxamic acid compounds of the following formula also inhibit neutral endopeptidase and are thus also useful within the method of this invention.

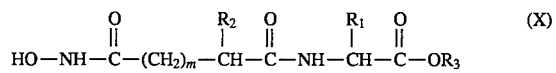

wherein $R_1$, $R_2$, m, and $R_3$ are as defined above.

The term "lower alkyl" refers to straight or branched chain saturated hydrocarbons of 1 to 7 carbons, preferably 1 to 4 carbons. Similarly, the term "cycloalkyl" refers to saturated hydrocarbon rings of 4 to 7 carbons, preferably 5 or 6 carbons.

The mercapto and acylmercapto compounds of formula I can be prepared as disclosed by Ondetti et al. in U.S. Pat. No. 4,053,651 and Delaney et al. in European Patent Application No. 136,883. An amino acid or ester compound of the formula

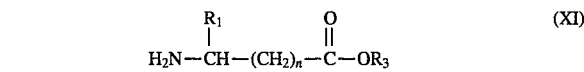

is acylated with an acid or its chemical equivalent of the formula

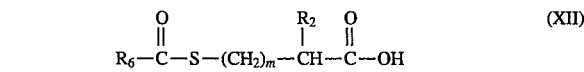

to yield the acylmercapto compounds of formula I. Conventional hydrolysis yields the corresponding mercapto compounds of formula I.

The mercapto and acylmercapto dipeptides of formulas II can be prepared as disclosed by Ondetti et al. in Australian Patent No. 537,592. These compounds can be prepared by acylating the dipeptide

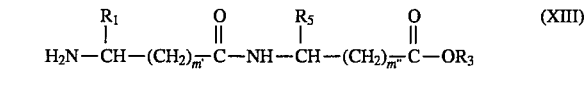

or

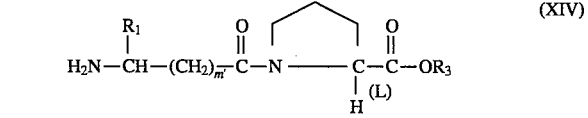

with the acid or its chemical equivalent of formula XII to yield the desired acylmercapto dipeptide products. Conventional hydrolysis yields the corresponding mercapto dipeptides of formula II.

These dipeptides can also be prepared as disclosed by Sundeen et al. in U.S. Pat. No. 4,235,885. These compounds can be prepared by converting the acyl amino acid of the formula

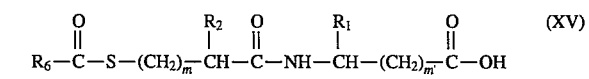

to an activated form such as the p-nitrophenyl ester and reacting with the amino acid of the formula

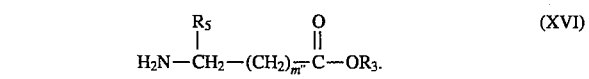

Conventional hydrolysis yields the corresponding mercapto dipeptides of formula II.

Similarly, the acylmercapto and mercapto cycloalkanoyl dipeptides of formula III are prepared as disclosed by Weller et al. in U.S. Pat. No. 4,560,506. These compounds when m is zero can be prepared by coupling an acylmercaptocycloalkyl carboxylic acid or its chemical equivalent of the formula

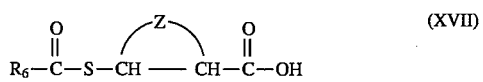

with the dipeptide of formulas XIII or XIV. Conventional hydrolysis yields the corresponding mercapto compounds of formula III.

The acylmercapto and mercapto compounds of formula IV are prepared as disclosed by Delaney et al. European Patent No. 161,769. These compounds can be prepared by reacting an acylthiol of the formula

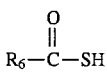  (XVIII)

with the intermediate of the formula

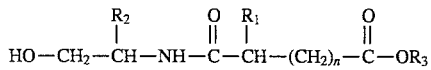  (XIX)

in the presence of triphenylphosphine and a dialkyl azodicarboxylate. Again, conventional hydrolysis yields the corresponding mercapto compounds of formula IV.

The intermediate of formula XIX can be prepared by coupling an amine of the formula

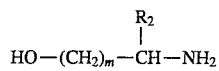  (XX)

with an acid or its chemical equivalent of the formula

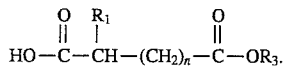  (XXI)

The carboxyacyl dipeptides of formula V can be prepared as disclosed by Gordon et al. in U.S. Pat. No. 4,499,079. For example, a carboxylic acid or its chemical equivalent of the formula

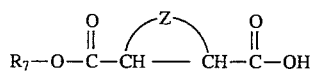  (XXII)

is coupled to the dipeptide of formula XIII.

The compounds of formula III wherein m is one can be prepared as described by Weller et al. in U.S. Pat. No. 4,560,506. For example, the carboxylic acid cycloalkanoyl-dipeptide of formula V is treated with borane in tetrahydrofuran to yield the alcohol of the formula

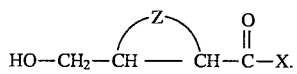  (XXIII)

The alcohol of formula XXIII is treated with the acylmercaptan of the formula

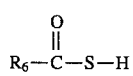  (XXIV)

in the presence of diisopropylazodicarboxylate and triphenylphosphine. Conventional hydrolysis yields the mercaptan compounds of formula III wherein m is one.

The carboxylic acid dipeptide compounds of formula VI can be as disclosed by Berger in U.S. Pat. No. 4,610,816. For example, an amino acid of the formula

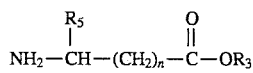  (XXV)

can be coupled with the amino acid of the formula

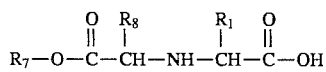  (XXVI)

in the presence of a coupling reagent such as dicyclohexylcarbodiimide.

The carboxylic acid alkanoyl amino acids of formula VII can be prepared as disclosed by Ksander in PCT Application WO 86/00066. For example, an amino acid of formula XXV can be coupled with the carboxylic acid or its chemical equivalent of the formula

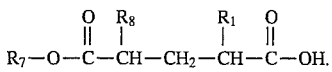  (XXVII)

The phosphoryl compounds of formula VIII wherein $R_9$ is hydroxy, alkoxy, aralkoxy, cycloalkylalkoxy, or heterocycloalkoxy and Y is O or NH can be prepared as taught by Thorsett et al. in U.S. Pat. No. 4,316,896. For example, the phosphorochloridate diester of the formula

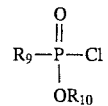  (XXVIII)

can be reacted with the dipeptide of formula XIII wherein m' and m" are both zero to give the compounds of formula VIII wherein $R_9$ is as defined above and Y is NH.

Similarly, the phosphorochloridate of formula XXVIII can be reacted with an alcohol of the formula

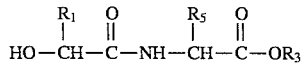  (XXIX)

to give the compounds of formula VIII wherein $R_9$ is hydroxy or a substituted oxygen as defined above and Y is O.

The phosphorus compounds of formula VIII wherein Y is $CH_2$ and the phosphorus compounds of formula IX can be prepared as disclosed by Gaeta in European Patent Application No. 117,429. For example, an acid of the formula

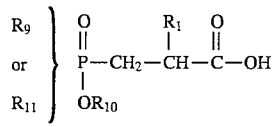  (XXX)

or its chemical equivalent is coupled to the amino acid of formula XXV wherein n is zero to give the phosphorus compounds of formula VIII wherein Y is $CH_2$. Similarly, the acid of formula XXX is coupled to the amino acid of the formula

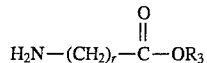  (XXXI)

to give the phosphorus compounds of formula IX.

The phosphonamidate compounds of formula VIII wherein $R_9$ is lower alkyl, aralkyl, aryl, cycloalkyl, cycloalkylalkyl, heterocycloalkyl, aminoalkyl, or acylaminoalkyl and Y is NH can be prepared as taught by Karanewsky et al. in U.S. Pat. No. 4,432,972. For example, these compounds can be prepared by coupling a phosphonochloridate of formula XXVIII wherein $R_9$ is as defined above to the dipeptide of formula XIII wherein m' and m" are both zero.

The phosphonyl compounds of formula VIII wherein $R_9$ is lower alkyl, aralkyl, aryl, cycloalkyl, cycloalkylalkyl, heterocycloalkyl, aminoalkyl, or acylaminoalkyl and Y is O can be prepared as taught by Karanewsky et al. in U.S. Pat. No. 4,616.005. For example, these compounds can be prepared by coupling an acid of the formula

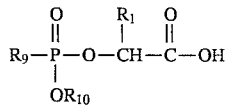  (XXXII)

or its chemical equivalent to the amino acid of formula XXV wherein n is zero.

The compound phosphoramidon can be prepared as taught by Suda et al. (Journal of Antibiotics, Vol. 26, p.

621–623, 1973) and Umezawa et al. (Tetrahedron Letters, No. 1, p 97–100, 1972).

The hydroxamic acid compounds of formula X can be prepared as disclosed by Ondetti et al. in U.S. Pat. No. 4,105,789 and Wilkinson et al. in U.S. Pat. No. 4,504,492. For example, these compounds can be prepared by treating a carboxylic acid of the formula

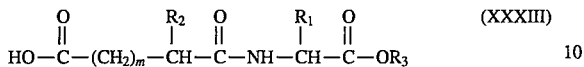  (XXXIII)

or its chemical equivalent with hydroxylamine.

The carboxylic acid of formula XXXIII can be prepared by coupling a malonic or succinic acid monoester of the formula

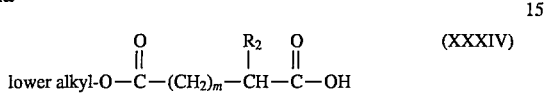  (XXXIV)

or its chemical equivalent to the amino acid of formula XI wherein n is zero. Saponification removes the ester group and gives the carboxylic acid of formula XXXIII.

The compounds of formulas I to X can contain one or more asymmetric centers. Thus, these compounds can exist in diastereoisomeric forms or in mixtures thereof. The above described processes can utilize racemates, enantiomers, or diastereomers as starting materials. When diastereomeric compounds are prepared, they can be separated by conventional chromatographic or fractional crystallization methods.

In the above reactions, depending upon the definition of $R_1$, $R_2$, and $R_5$ it may be necessary to employ a protecting group which is then removed as the last step in the synthesis. Suitable protecting groups and methods for their introduction and removal are well known. Also, many of the reactions described above are coupling reactions which can be best performed in the presence of a reagent such as dicyclohexylcarbodiimide or carbonyldiimidazole or can be best performed by converting an acid reagent to an activated form. Suitable activated forms include acid chlorides, anhydrides, mixed anhydrides, etc.

The compounds of formulas I to X which are useful within the method of this invention can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of the base supplying the desired ion in a medium in which the salt precipitates or in an aqueous medium and then lyophilizing.

Some of the compounds can also form salts with a variety of pharmaceutically acceptable inorganic and organic acids such as those formed with hydrochloric acid, methanesulfonic acid, maleic acid,, etc. Again, these salts can be prepared by reacting the compound with an equivalent amount of the acid in a medium in which the salt precipitates.

Preferred compounds for use within the method of this invention are the neutral endopeptidase inhibitors of formula I wherein:

$R_4$ is hydrogen.

m is one.

$R_2$ is benzyl or straight or branched chain lower alkyl of 1 to 4 carbons, especially benzyl, -$CH_3$ or -$CH_2$-CH-($CH_3)_2$.

$R_3$ is hydrogen or a pharmaceutically acceptable salt forming ion.

n is zero.

$R_1$ is hydrogen, straight or branched chain lower alkyl of 1 to 4 carbons, benzyl,

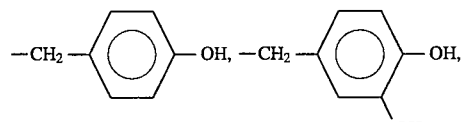

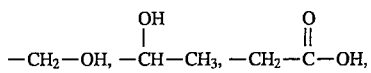

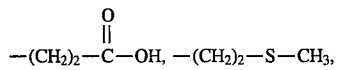

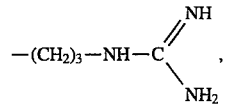

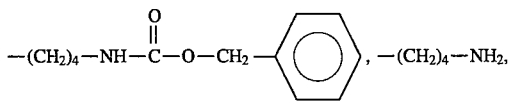

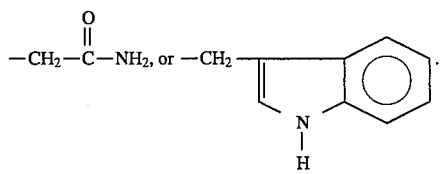

Also preferred compounds for use within the method of this invention are the neutral endopeptidase inhibitors of formula I wherein:

$R_4$ is hydrogen.

m is one.

$R_2$ is benzyl.

$R_1$ is hydrogen or benzyl, especially hydrogen.

n is an integer from 1 to 9.

$R_3$ is hydrogen or a pharmaceutically acceptable salt forming ion.

Also preferred compounds for use within the method of this invention are the neutral endopeptidase inhibitors of formula II wherein:

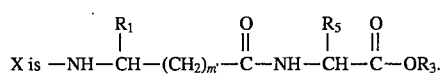

$R_4$ is hydrogen.

m and m' are independently selected from zero and one.

m" is zero.

$R_2$ is hydrogen, -$CH_2$-CH–($CH_3)_2$, or

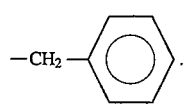

$R_1$ and $R_5$ are independently selected from hydrogen, straight or branched chain lower alkyl of 1 to 4 carbons, benzyl,

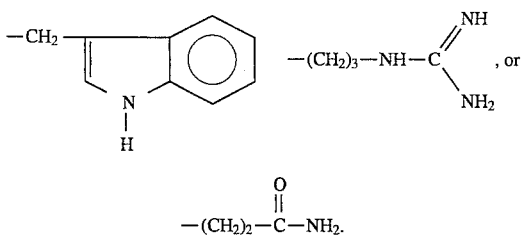

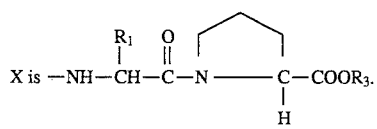

$R_3$ is hydrogen or a pharmaceutically acceptable salt forming ion.

Also preferred compounds for use within the method of this invention are the neutral endopeptidase inhibitors of formula II wherein:

$$X \text{ is } -NH-\underset{\underset{R_1}{|}}{CH}-\underset{\underset{}{\overset{O}{\|}}}{C}-N\underset{\underset{H}{|}}{\phantom{X}}\overbrace{\phantom{XXXX}}C-COOR_3.$$

$R_4$ is hydrogen.
m is zero or one.
$R_2$ is benzyl.
$R_1$ is methyl.
$R_3$ is hydrogen or a pharmaceutically acceptable salt forming ion.

Also preferred compounds for use within the method of this invention are the neutral endopeptidase inhibitors of formula IV wherein:
$R_4$ is hydrogen.
$R_2$ is benzyl.
$R_1$ is hydrogen.
n is zero or an integer from 1 to 5.
$R_3$ is hydrogen or a pharmaceutically acceptable salt forming ion.

Also preferred compounds for use within the method of this invention are the neutral endopeptidase inhibitors of formula VI wherein:
$R_1$ and $R_8$ are both benzyl.
$R_5$ is hydrogen and n is zero or an integer from 1 to 5 or $R_5$ is straight or branched chain lower alkyl of 1 to 4 carbons and n is zero.
$R_3$ and $R_7$ are both hydrogen or both a pharmaceutically acceptable salt forming ion.

Also a preferred compound for use within the method of this invention is the neutral endopeptidase inhibitor phosphoramidon.

Also preferred compounds for use within the method of this invention are the neutral endopeptidase inhibitors of formula VIII wherein:
Y is -NH, -$CH_2$, or O.
$R_1$ is benzyl.
$R_5$ is -$CH_2$-$CH(CH_3)_2$.
$R_9$ is methyl.
$R_3$ and $R_{10}$ are both hydrogen or both a pharmaceutically acceptable salt forming ion.

Also preferred compounds for use within the method of this invention are the neutral endopeptidase inhibitors of formula IX wherein:
$R_9$ is hydroxy.
$R_1$ is benzyl.
r is two.
$R_3$ is hydrogen or a pharmaceutically acceptable salt forming ion.

Diuresis and natriuresis are produced in a mammalian host by the administration of from about 1 mg. to about 100 mg. per kg. of body per day, preferably from about 1 mg. to about 50 mg. per kg. of body per day, of one or more neutral endopeptidase inhibitors resulting in the lowering of the blood pressure of the host. The neutral endopeptidase inhibitor is preferably administered orally, but parenteral routes such as subcutaneous, intramuscular, and intravenous can also be employed. The daily dose can be administered singly or can be divided into two to four doses administered throughout the day.

The neutral endopeptidase inhibitor can also be administered in combination with other blood pressure lowering agents. For example, the neutral endopeptidase inhibitor can be combined for dual administration with an angiotensin converting enzyme (ACE) inhibitor such as captopril, zofenopril, fosenopril, enalopril, lisinopril, etc. Such combination would be at a weight ratio of endopeptidase inhibitor to ACE inhibitor of from about 1:10 to about 10:1.

The neutral endopeptidase inhibitor and other pharmaceutically active ingredient can be formulated for use in the reduction of blood pressure in compositions such as tablets, capsules or elixirs for oral administration, or in sterile solutions or suspensions for parenteral administration. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade.

EXAMPLE 1

N-[2-(Mercaptomethyl)-1-oxo-3-phenylpropyl]-L-leucine (Isomer A)

Oxalyl chloride (4.54 ml., 52 mmole) is added to a solution of 3-acetylthio-2-benzylpropanoic acid (11.92 g., 50 mmole) in ether (100 ml.). This mixture is cautiously treated with a catalytic amount of dimethylformamide (3 drops) and then stirred for one hour at room temperature. The mixture is concentrated in vacuo producing an oil that is dissolved in tetrahydrofuran (80 ml.) and again concentrated in vacuo. The resulting residue is dissolved in methylene chloride (80 ml.) and added dropwise over 1 hour to a cold (−5°), stirred solution of L-leucine, methyl ester, monohydrochloride (8.45 g., 51 mmole) and diisopropylethylamine (18.12 ml., 104 mmole) in methylene chloride (100 ml.). After stirring in the cold (−5°) for 2.5 hours, the mixture is concentrated in vacuo. The residue is taken up into ethyl acetate (300 ml.), filtered, and the filtrate is washed sequentially with 10% potassium bisulfate, water, 50% saturated sodium bicarbonate, water, and 50% brine (3 ×50 ml. each). The organic layer is dried over sodium sulfate and concentrated to yield 17.64 g. of yellow foam. One half of this material is applied to a column of silica gel (Merck, 230–400 mesh) eluting with petroleum ether/ethyl acetate (7:2). Fractions containing only the faster moving isomer are pooled and concentrated. After all of the slower moving diastereomer is eluted, the column is flushed with about one liter of the same solvent. The remaining half of the mixture is applied to this column and eluted in the same manner to yield a total of 8.76 g. of N-[2-(acetylthiomethyl)-1-oxo-3-phenylpropyl]-L-leucine, methyl ester (isomer A) as a white solid, m.p. 64°–66°.

This methyl ester product (8.75 g., 23.94 mmole) is dissolved in methanol (72 ml.) and chilled in an ice bath under nitrogen. 1N Sodium hydroxide (72 ml., approximately 3 equivalents) is added dropwise to this solution over 10 minutes. The mixture is stirred at 0° for 10 minutes and then allowed to warm to room temperature and stirred for 3 hours. The mixture is concentrated to half volume in vacuo. The residue is diluted with water (100 ml.), washed with chloroform (2×40 ml.), and the aqueous portion is acidified to pH of about 1.5 with concentrated HCl. The resulting white suspension is extracted with ethyl acetate (3×40 ml.). These extracts are combined, washed with water and brine (40 ml. each), dried over sodium sulfate, and concentrated to yield 7.2 g. of a colorless oil. This oil is applied to a column of silica gel (Merck, 230–400 mesh) eluting with toluene/acetic acid (6:1) to yield a colorless oil. This oil is taken up in benzene, concentrated and dried for 48 hours to yield 6.0 of white solid N-[2-(mercapto-methyl)- 1-oxo-3-phenylpropyl]-L-leucine (isomer A); 87°–88° (sinters at greater than 81°). TLC (silica gel; benzene:acetic acid, 4:1) $R_f$=0.44 (trace at 0.29). TLC (silica gel; chloroform:acetic acid, 15:1) $R_f$=0.32 (trace at 0.14). Anal. calc'd. for $C_{16}H_{23}NO_3S$: C, 62.11; H, 7.49; N, 4.53; S, 10.35 Found: C, 62.06; H, 7.52; N, 4.52; S, 10.08.

EXAMPLE 2

N-(3-Mercapto-1-oxopropyl)-L-phenylalanine

This compound can be prepared as described in detail in Example 6 of U.S. Pat. No. 4,053,651.

EXAMPLE 3

N-(DL-3-Mercapto-2-methyl-1-oxopropyl)-L-arginine

This compound can be prepared as described in detail in Example 21 of U.S. Pat. No. 4,053,651.

EXAMPLE 4

N-[DL-2-(Mercaptomethyl)-1-oxo-3,-phenylpropyl]-L-arginine

This compound can be prepared as described in detail in Example 34 of U.S. Pat. No. 4,053,651.

EXAMPLE 5

N-(DL-3-Mercapto-2-methyl-1-oxopropyl)-L-tryptophan

This compound can be prepared as described in detail in Example 29 of U.S. Pat. No. 4,053,651.

EXAMPLE 6

N-(DL-3-Mercapto-2,methyl1-oxopropyl)-L-tyrosine

This compound can be prepared as described in detail in Example 28 of U.S. Pat. No. 4,053,651.

EXAMPLE 7

3-Hydroxy-N-(DL-3-mercapto-2-methyl-1-oxopropyl)-L-tyrosine

This compound can be prepared as described in detail in Example 76 of U.S. Pat. No. 4,339,600.

EXAMPLE 8

(±)-N-[2-(Mercaptomethyl)-4-methyl-1-oxopentyl]-glycine

This compound can be prepared as described in detail in Example 3 of U.S. Pat. No. 4,235,885.

EXAMPLE 9

(±)-N-[2-(Mercaptomethyl)-1-oxo-3-phenylpropyl]-glycine

Benzyl malonic acid (13 g., 67 mmole) is mixed with 40% aqueous dimethylamine (7.6 g., 68 mmole) and 37% formalin (5.4 g., 68 mmole) in water (150 ml.). The resulting solid that forms is filtered off after 2 hours, washed with water and partially air dried. The solid (20.8 g.) is melted in an oil bath and heated for 10 minutes until amine evolution stops and bubbling has virtually ceased. The cooled product, a mobile liquid, is acidified with 10% potassium bisulfate, extracted with hexane, dried over sodium sulfate, and evaporated to give 6.3 g. of solid benzylacrylic acid.

Benzylacrylic acid (6.2 g., 40 mmole) in methylene chloride (350 ml.) is treated with ethyl glycinate hydrochloride (5.4 g., 40 mmole) and triethylamine (3.9 g., 4 mmole). The mixture is cooled in an ice bath and dicyclohexylcarbodiimide (7.9 g., 40 mmole) is added. The mixture is stirred at room temperature for 16 hours and then filtered. The filtrate is shaken with aqueous bicarbonate, 10% potassium bisulfate, and water, dried over sodium sulfate, and evaporated to an oil. This oil is taken up in methanol (200 ml.) and treated with excess 10% sodium hydroxide. The mixture is heated for 15 minutes on a steam cone, and then evaporated to an aqueous slurry. This is filtered and the filtrates are extracted with ether. The aqueous layer is acidified with 10% HCl and extracted with chloroform. The extracts are dried over sodium sulfate and evaporated to an oil (7.3 g.).

Thiolacetic acid (10 ml.) is added to the above glycine derivative (3.2 g., 14 mmole) and after 16 hours the resulting solution is evaporated in vacuo. Trituration with isopropyl ether gives 2.9 g. of a near white solid. Recrystallization from ethyl acetate-hexane gives 2.5 g. of (±)-N-[2-(acetylthiomethyl)-1-oxo-3-phenylpropy-propyl]glycine;9 m.p. 97°–101°.

This acetylthiomethyl product (0.5 g., 1.7 mmole) is taken up in 10% sodium hydroxide (5 ml.) under argon. After 30 minutes at room temperature excess 10% potassium bisulfate is added, and the product is extracted into chloroform under an argon atmosphere. Drying over sodium sulfate and evaporation gives a solid. This solid is triturated with isopropyl ether and dried over phosphorus pentoxide in vacuo to give 0.3 g. of white solid (±)-N-[2-(mercaptomethyl)-1- oxo-3-phenylpropyl]glycine; m.p. 129°–134°.

Anal. calc'd. for $C_{12}H_{15}NO_3S$: C, 56.89; H, 5.97; N, 5.53; S, 12.66 Found: C, 56.46; H, 6.04; N, 5.37; S, 12.36.

EXAMPLE 10

(±)-N-[2-(Mercaptomethyl)-3-methyl-1-oxohexyl]-glycine, N-cyclohexylcyclohexanamine salt (1:1)

Following the procedure of Example 9 but employing the malonic acid

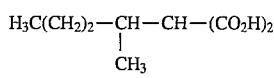

one obtains the acrylic acid

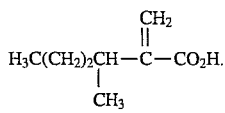

This acrylic acid is then reacted with ethyl glycinate hydrochloride and triethylamine in the presence of dicyclohexylcarbodiimide according to the procedure of Example 9. The resulting glycine derivative (5.4 g., 28 mmole) is dissolved in thiolacetic acid (15 ml.) and allowed to stand at room temperature for 16 hours. Evaporation in vacuo at room temperature gives a viscous oil. This oil is taken up in isopropyl ether and treated with excess dicyclohexylamine. The volume of isopropyl ether is increased to 200 ml. and in several hours the product solidifies. This material is filtered off and washed with ethyl acetate and hexane. Recrystallization from ethyl acetate gives 0.4 g. of (±)-N-[2-(acetylthiomethyl)- 3-methyl-1-oxohexyl]glycine, N-cyclohexylcyclohexanamine salt (1:1); m.p. 121°–123°.

This acetylthiomethyl product (0.5 g., 1.1 mmole) is shaken with 10% sodium hydroxide (4 ml.) and ether under argon. The aqueous phase is reextracted with ether, then acidified with 10% potassium bisulfate, and extracted with chloroform. Drying and evaporation gives 0.3 g. of colorless oil. This oil is taken up in ethyl acetate (5 ml.) and treated with excess dicyclohexylamine. Dilution with hexane and filtering after one day gives 0.25 g. of white solid (±)-N-[2-(mercaptomethyl)- 3-methyl-1-oxohexyl]glycine, N-cyclohexylcyclohexanamine salt (1:1); m.p. 112°–116°.

Anal. calc'd. for $C_{10}H_{19}NO_3S \cdot C_{12}H_{23}N \cdot 0.25\ H_2O$: C, 63.04; H, 10.22; N, 6.68; S, 7.64 Found: C, 63.02; H, 10.32; N, 6.63; S, 7.93.

EXAMPLE 11

(±)-$N^2$-[2-(Mercaptomethyl)-4-methyl-1-oxopentyl]-L-arginine (L)-Arginine (1.9 g., 11 mmole) is dissolved in water (10 ml.) containing sodium bicarbonate (0.9 g., 11 mmole). This suspension is cooled to 5° and 2-acetylthiomethyl-4-methylpentanoyl chloride (2.5 g., 11 mmole) in ether (5 ml.) is added dropwise. The pH of the reaction mixture is maintained between 7–8 by the occasional dropwise addition of saturated aqueous sodium bicarbonate. After stirring for 5 hours at room temperature, the reaction mixture is washed with ether and the aqueous solution is lyophilized to yield 3.6 g. of crude material. This is dissolved in absolute ethanol (10 ml.) and poured through a 100 ml. column of XAD-4 (previously washed with ethanol). After 200 ml. of ethanol goes through the column, the product is eluted in two 50 ml. fractions (2.3 g.). This material is chromatographed through 100 g. of silica gel using (9:1) methanol:water. The product is eluted in two 100 ml. fractions. Lyophilization of the first fraction gives 0.6 g. of (±)-$N^2$-[2-(acetyl-thiomethyl)- 4-methyl-1-oxopentyl]-L-arginine; m.p. softens at 64°–80°.

The above acetylthiomethyl product (0.6 g.) is dissolved in water and purged with argon. Aqueous ammonium hydroxide (37%, 2 ml.) is added and the mixture is stirred at room temperature for 2 hours. It is lyophilized over 16 hours. The resulting white solid is washed with acetonitrile (60 ml.) containing water (6 drops). The granular solid is filtered and dried in vacuo at 60° for 2 hours to give white solid (±)-$N^2$-[2-(mercaptomethyl)- 4-methyl-1-oxopentyl]-L-arginine; m.p. softens at 127°.

Anal. calc'd. for $C_{13}H_{26}N_4O_3S \cdot 1H_2O$: C, 46.41; H, 8.39; N, 16.65; S, 9.53 Found: C, 46.38; H, 8.21; N, 16.38; S, 9.42.

EXAMPLE 12

N-[2-(Mercaptomethyl)-4-methyl-1-oxopentyl]-L-alanine (isomer A)

2-Acetylthiomethyl-4-methylpentanoic acid (2.04 g., 10.0 mmole) is dissolved in dry dioxane (20 ml.). The solution is cooled to 15° and N-hydroxysuccinimide (1.15 g., 10.0 mmole) is added followed by the portionwise addition of dicyclohexylcarbodiimide. The mixture is stirred at room temperature for 5 hours and is then filtered into an aqueous solution of sodium bicarbonate (0.84 g., 15 ml.) and (L)-alanine (0.9 g.). After stirring for 20 hours, the reaction mixture is concentrated in vacuo. The pot residue is dissolved in water (20 ml.) and washed with ethyl acetate. The aqueous solution is acidified with concentrated HCl and the product is extracted with ethyl acetate. The extract is dried over magnesium sulfate, filtered, and concentrated in vacuo to yield 1.5 g. of crude product. This material is placed on 50 g. of silica and petroleum ether (250 ml.) is filtered through followed by (1:1) ether:petroleum ether (250 ml.). The product is eluted with ether (250 ml.) to yield 1.2 g.

This crude product is treated with dicyclohexylamine in ethyl acetate. The first crop is allowed to crystallize for two days; m.p. 145°–152°. It is filtered and recrystallized once from ethyl acetate and then from (1:1) ethyl acetate:acetonitrile to give N-[2-(acetylthiomethyl)- 4-methyl-1-oxopentyl]-L-alanine, (isomer A), N-cyclohexylcyclohexanamine salt (1:1).

The above salt (1.0 g.) is dissolved in water (10 ml.), layered with ether, and saturated with argon. 10% Sodium hydroxide (5 ml.) is added and the mixture is allowed to stand at room temperature for 30 minutes. Ether is decanted and the aqueous solution is washed a second time with ether. The basic solution is then acidified with 10% potassium bisulfate and the product is extracted with methylene chloride, dried over sodium sulfate, filtered, and concentrated in vacuo at 50° to give N-[2-(mercaptomethyl)-4-methyl-1-oxopentyl]-L-alanine (isomer A); $[\alpha]_D = -33°$ (c=1%, 95% ethanol).

Anal. calc'd. for $C_{10}H_{19}NO_3S \cdot 0.2H_2O$: C, 50.70; H, 8.25; N, 5.91; S, 13.53 Found: C, 50.88; H, 7.75; N, 5.74; S, 13.34.

Example 13

N-[2-(Mercaptomethyl)-4-methyl-1-oxopentyl]-L-alanine (isomer B)

The filtrates from the dicyclohexylamine treatment in Example 12 are concentrated in vacuo and the free acid is liberated by washing an ethyl acetate solution with 10% potassium bisulfate. After concentrating the organic extract in vacuo, the crude acid is chromatographed on silica (200 g.) eluting with (9:1) ethyl acetate:acetic acid to give 1.3 g. of crude product. This sample is converted to the dicyclohexylamine salt and is recrystallized twice from acetonitrile to yield 1.2 g. of N-[2-(acetyl-thiomethyl) -4-methyl-1- oxopentyl]-L-alanine (isomer B), N-cyclohexylcyclohexanamine salt (1:1); m.p. 131°–134 °; $[\alpha]_D$=+36° (c=1% in 95% ethanol).

The above salt (0.9 g.) is dissolved in water. This solution is purged with argon and layered with ether. 10% Sodium hydroxide (2 ml.) is added and the mixture is allowed to stand for 5 minutes. The ether is discarded. The aqueous layer is acidified with 10% HCl and the free acid is extracted with ether. After drying over sodium sulfate and concentrating in vacuo, the acid is dissolved in absolute ethanol and 37% ammonia (1 ml.). The mixture is stirred under argon for 2 hours, concentrated in vacuo, and dissolved in ether. The ether layer is washed with 10% HCl, dried over magnesium sulfate, filtered, and dried in vacuo at 40° to yield 0.5 g. of N-[2-(mercapto-methyl) -4-methyl-1-oxopentyl]-L-alanine (isomer B); $[\alpha]_D$=–35.7° (c=1% in 95% ethanol)

Anal. calc'd. for $C_{10}H_{19}NO_3S$: C, 51.48; H, 8.21; N, 6.00; S, 13.74 Found: C, 51.29; H, 8.10; N, 5.82; S, 13.53.

EXAMPLE 14

3-Hydroxy-N-(D-3-mercapto-2-methyl-1-oxopropyl)-L-tyrosine

D-3-Acetylthio-2-methylpropanoyl chloride (10.84 g., 60 mmole) is added in 5 portions to 3-hydroxy-L-tyrosine (11.83 g., 60 mmole) simultaneously with an equal portion of 1N sodium hydroxide (60 ml.) at 0° under nitrogen. The reaction is allowed to stir at room temperature for 4 hours. It is then layered with ethyl acetate (200 ml.) and made strongly acidic with concentrated HCl. The aqueous extract is then extracted with ethyl acetate (2×200 ml.) and the combined organic layers are dried over magnesium sulfate. The solvent is removed and the residue is dissolved in ethyl acetate (30 ml.). Ether (250 ml.) is added and then dicyclohexylamine (9.05 g., 50 mmole) in ether (30 ml.). The white crystalline dicyclohexylamine salt of 3-hydroxy-N-[D-3-(acetylthio)-2-methyl-1-oxopropyl]-L-tyrosine forms immediately. This salt is filtered and dried overnight; m.p. softens at 60°, 75°–80°.

This salt is converted to the free acid by using ethyl acetate and potassium bisulfate.

The resulting acetylthio compound is treated with aqueous ammonia under nitrogen to give 3-hydroxy-N-(D-3-mercapto-2-methyl-1-oxopropyl)-L -tyrosin; m.p. softens at 45°, 50°–55 °; $[\alpha]_D$=–1.1° (c=1, methanol). TLC (silica gel; chloroform:acetic acid, 7:3) $R_f$=0.29.

Anal. calc'd. for $C_{13}H_{17}NO_5S \cdot 0.5\ H_2O$: C, 50.63; H, 5.88; N, 4.54; S, 10.39 Found: C, 50.09; H, 6.06; N, 4.60; S, 10.39.

EXAMPLE 15

3-Hydroxy-N-(R-3-mercapto-2-methyl-1-oxopropyl)-L-tyrosine

Following the procedure of Example 14 but employing R-3-acetylthio-2-methylpropanoyl chloride, one obtains 3-hydroxy-N-(R-3-mercapto-2-methyl-1-oxopropyl)-L-tyrosine; m.p. 40°–50°; $[\alpha]_D$=+21.9° (c=1, methanol).

Anal. calc'd. for $C_{13}H_{17}NO_5S \cdot 0.6\ H_2O$: C, 50.34; H, 5.81; N, 4.52; S, 10.34 Found: C, 50.01; H, 6.02; N, 4.51; S, 10.54.

EXAMPLE 16

(±)-N-(3-Mercapto-2-methyl-1-oxopropyl)glycine

3-Acetylthio-2-methylpropanoyl chloride (12.6 g., 66 mmole) and a solution of sodium carbonate (12 g., 880 mmole) in water (50 ml.) are added simultaneously, in 5 separate portions over a 15 minute period, with thorough stirring to a cooled (0°) solution of glycine (5.7 g., 75 mmole), sodium carbonate (4.0 g., 38 mmole) and water (100 ml.). The mixture is then washed with three portions of ethyl acetate, acidified with concentrated HCl to a pH of 2, and extracted with three portions of ethyl acetate. The organic phases are combined, dried over sodium sulfate, and concentrated in vacuo to give 12.5 g. of (±)-N-[3-(acetylthio)-2-methyl-1-oxopropyl]glycine.

A solution of the acetylthio product (12.3 g., 60 mmole) in water (34 ml.) and concentrated ammonia (23 ml.) is stirred for one hour at room temperature and then washed with three portions of ethyl acetate. The aqueous phase is acidified with concentrated HCl to pH 2 and extracted with three portions of ethyl acetate. The organic extracts are combined, washed with water, dried over sodium sulfate, and concentrated in vacuo to give 5.89 g. of a yellow oil. The oil is crystallized from ethyl acetate to give 1.39 g. of white solid (±)-N-(3-mercapto-2-methyl-1-oxopropyl)-glycine; m.p. 121.5°–123.5°. TLC (silica gel; acetone:acetic acid, 15:1) $R_f$=0.57.

Anal. calc'd. for $C_6H_{11}NO_3S$: C, 40.70; H, 6.26; N, 7.91; S, 18.09 Found: C, 40.67; H, 6.20; N, 7.94; S, 17.87.

EXAMPLE 17

(±)-N-(3-Mercapto-2-methyl-1-oxopropyl),L-phenyl, alanine, 1,-dimethylethanamine salt (1:1)

Following the procedure of Example 16, L-phenylalanine is reacted with 3-acetylthio-2-methylpropanoyl chloride to give (±)-N-[3-(acetylthio)-2-methyl-1-oxopropyl]-L-phenylalanine.

A solution of this acetylthio product in water is treated with concentrated ammonia and methanol under argon for two hours. The mixture is acidified to pH of about 2 with concentrated HCl and then extracted with ethyl acetate. The organic layers are combined, washed with water, dried over sodium sulfate, and concentrated in vacuo to a golden yellow oil. Tert-butylamine (0.36 g., 5.04 mmole) is added to a solution of this oil (1.27 g., 4.95 mmole) in diethyl ether (10 ml.). The mixture is allowed to react for 5 minutes at room temperature, and then the white precipitate is triturated with diethyl ether (2×25 ml.). Drying overnight gives 1.15 g. of (±)-N-(3-mercapto-2-methyl-1-oxopropyl)-L-phenylalanine, 1,1-dimethylethanamine salt (1:1) as a white powder; m.p. 151.5°–157°. TLC (silica gel; acetone:acetic acid, 30:1) $R_f$=0.51.

Anal. calc'd. for $C_{13}H_{17}NO_3S \cdot C_4H_{11}N$: C, 59.97; H, 8.29; N, 8.23; S, 9.24 Found: C, 59.31; H, 8.17; N, 8.06; S, 9.20.

EXAMPLE 18

(±)-N-(3-Mercapto-2-methyl-1-oxopropyl)-L-leucine, 1,1-dimethylethanamine salt (1:1)

Following the procedure of Example 16, L-leucine is reacted with 3-acetylthio-2-methylpropanoyl chloride to give (±)-N-[3-(acetylthio)-2-methyl -1-oxopropyl]-L-leucine.

An aqueous solution of this acetylthio product is treated with concentrated ammonia under argon for 1.5 hours and extracted with ethyl acetate. The aqueous portion is then acidified to pH of 2 with concentrated HCl. The resulting white oily mixture is extracted with ethyl acetate and the organic layers are combined, washed with water, dried over sodium sulfate, and concentrated in vacuo to yield a clear oil. A solution of this oil in diethyl ether is treated with tert-butylamine to give (±)-N-(3-mercapto-2-methyl-1-oxopropyl)-L-leucine, 1,1-dimethylethanamine salt (1:1); m.p. 143–154 (dec.). TLC (silica gel; acetone:acetic acid, 30:1) $R_f$=0.54.

Anal. calc'd. for $C_{10}H_{19}NO_3S \cdot C_4H_{11}N$: C, 54.87; H, 9.87; N, 9.14; S, 10.46 Found: C, 54.44; H, 9.69; N, 8.81; S, 10.25.

EXAMPLE 19

(±)-N-(3-Mercapto-2-methyl-1-oxopropyl)-L-glutamic acid, 1,1-dimethylethanamine salt (1:2)

Following the procedure of Example 16, L-glutamic acid is reacted with 3-acetylthio-2-methylpropanoyl chloride to give (±)-N-[3-(acetylthio)-2-methyl -1-oxopropyl]-L-glutamic acid.

An aqueous solution of this acetylthio product is treated with concentrated ammonia under argon and worked up as in Example 18. A solution of the 3-mercapto product in diethyl ether is treated with tert-butylamine to give (±)-N-(3-mercapto-2-methyl-1-oxopropyl) -L-glutamic acid, 1,1-dimethylethanamine salt (1:2); 167°–185° (dec.); TLC (silica gel; butanol: acetic acid:water, 3:1:1) $R_f$=0.55.

Anal. calc'd. for $C_9H_{15}NO_5S \cdot 2C_4H_{11}N \cdot 0.5 H_2O$: C, 50.47; H, 9.22; N, 10.39; S, 7.93 Found: C, 50.72; H, 9.14; N, 10.31; S, 8.44.

EXAMPLE 20

(±)-N-(3-Mercapto-2-methyl-1-oxopropyl)-L-valine

Following the procedure of Example 16, L-valine is reacted with 3-acetylthio-2-methyl-propanoyl chloride to give (±)-N-[3-(acetylthio)-2-methyl -1-oxopropyl]-L-valine.

An aqueous solution of this acetylthio product is treated with concentrated ammonia and worked up according to the procedure of Example 16 to give (±)-N-(3-mercapto-2-methyl-1-oxopropyl)-L-valine; m.p. 150°–157°. TLC (silica gel; butanol: acetic acid:water, 3:1:1) $R_f$=0.61/0.64 overlapping.

Anal. calc'd. for $C_9H_{17}NO_3S$: C, 49.29; H, 7.81; N, 6.39; S, 14.62 Found: C, 49.18; H, 7.47; N, 6.64; S, 14.43.

EXAMPLE 21

(±)-N-(3-Mercapto-2-methyl-1-oxopropyl)-L-serine, N-cyclohexylcyclohexamine salt(1:1)

Following the procedure of Example 16, L-serine is reacted with 3-acetylthio-2-methylpropanoyl chloride to give (±)-N-[3-(acetylthio)-2-methyl -1-oxopropyl]-L-serine.

An aqueous solution of this acetylthio product is treated with concentrated ammonia under argon and worked up as in Example 18. A solution of the 3-mercapto product in acetonitrile is treated with a solution of dicyclohexylamine in diethyl ether. A white precipitate forms and is triturated in diethyl ether. Drying overnight gives (±)-N-(3-mercapto-2-methyl -1-oxopropyl)-L-serine, N-cyclohexylcyclo-hexan-amine salt (1:1) as a white powder; m.p. 163°–171°. TLC (silica gel;. butanol:acetic acid:water, 3:1:1) $R_f$=0.65.

Anal. calc'd. for $C_7H_{13}NO_4S \cdot C_{12}H_{23}N$: C, 58.73; H, 9.34; N, 7.21; S, 8.25 Found: C, 58.39; H, 9.27; N, 7.20; S, 8.22.

EXAMPLE 22

(±)-N-[2-(Mercaptomethyl)-1-oxo-3-phenylpropyl]-L -methionine

3-Acetylthio-2-benzylpropanoyl chloride (3.85 g., 15 mmole) is added dropwise over seven minutes to a cold (0°) stirred suspension of L-methionine, methyl ester, hydrochloride salt (3.29 g., 16.5 mmole) and triethylamine (4.6 ml.) in methylene chloride (75 ml.). The mixture is stirred for 2.5 hours in the cold and then diluted with methylene chloride (100 ml.). The resulting yellow solution is extracted successively with 10% aqueous HCl (50 ml.), saturated sodium bicarbonate (50 ml.), and brine (75 ml.), dried over sodium sulfate, and concentrated in vacuo to give 5.94 g. of (±)-N-[2-(acetylthiomethyl)-1-oxo-3-phenylpropyl]-L -methionine, methyl ester as a dark yellow oil.

1N Sodium hydroxide (16.9 ml.) is added with thorough stirring to a cold (−5°), argon flushed, solution of this acetylthio product (2.94 g., 7.67 mmole) in methanol (20 ml.). The mixture is stirred for 3 hours in the cold, then poured into water (125 ml.), and extracted with diethyl ether (2×40 ml.). The aqueous portion is acidified to pH of about 1 with concentrated HCl and extracted with ethyl acetate (3×40 ml.). The organic layers are combined, washed with brine (60 ml.), dried over sodium sulfate, and concentrated in vacuo to a light yellow solid (2.06 g.). Recrystallization of 1.4 g. from ethyl acetate/ hexane yields 1.07 g. of (±)-N-[2-(mercaptomethyl)-1 -oxo-3-phenylpropyl]-L-methionine as a white powder; m.p. 130°–141°. TLC (silica gel; butanol:acetic acid:water, 4:1:1) $R_f$=0.69.

Anal. calc'd. for $C_{15}H_{21}NO_3S_2$: C, 55.02; H, 6.46; N, 4.28; S, 19.58 Found: C, 55.14; H, 6.46; N, 4.19; S, 19.14.

EXAMPLE 23

(±)-N-(3-Mercapto-2-methyl-1-oxopropyl)-L-methionine, 1,1-dimethylethanamine salt (1:1)

3-Acetylthio-2-methylpropanoyl chloride (3.78 ml., 25 mmole) is added dropwise over six minutes to a cold (−5°), stirred suspension of (L)-methionine, methyl ester, hydrochloride salt (4.99, 25 mmole) and triethylamine (13.94 g.) in methylene chloride (100 ml.). The mixture is stirred in the cold for three hours and then diluted with methylene chloride (100 ml.). The resulting yellow solution is washed sequentially with 10% aqueous HCl (70 ml.), saturated sodium bicarbonate (70 ml.) and brine (100 ml.), dried over sodium sulfate, and concentrated in vacuo to give (±)-N-[3-(acetylthio)-2 -methyl-1-oxopropyl]-L-methionine, methyl ester.

A solution of this acetylthio product in methanol is treated with 1N sodium hydroxide and worked up according to the procedure of Example 22 to give (±)-N-(3-mercapto)-2-methyl-1-oxopropyl)-L-methionine. Tert-butylamine is added to a solution of the mercapto product in diethyl ether. The resulting yellow gum is triturated in ether to give a light yellow solid. Recrystallization from ethyl acetate/ethyl ether gives (±)-N-(3-mercapto-2-methyl-1-oxopropyl)-L-methionine, 1,1-dimethylethanamine salt (1:1) as a white powder; m.p. decomposes slowly above 109°. TLC (silica gel; butanol:acetic acid: water, 4:1:1) $R_f$=0.64.

Anal. calc'd. for $C_9H_{17}NO_3S_2 \cdot C_4H_{11}N$ C, 48.12; H, 8.70; N, 8.63; S, 19.76 Found: C, 47.87; H, 8.68; N, 8.45; S, 19.59.

EXAMPLE 24

(±)-3-Hydroxy-N-[2-(mercaptomethyl)-1-oxo-3-phenylpropyl] -L-tyrosine, 1,1-dimethylethanamine salt (1:1)

3-Hydroxy-(L)-tyrosine (6.9 g., 35 mmole) and ether (30 ml.) are added to a stirred, chilled (–5°) solution of sodium borate decahydrate (7.03 g., 17.5 mmole) in 1N sodium hydroxide (75 ml.) under argon. 3-Acetylthio-2-benzylpropanoyl chloride (8.97 g., 34.9 mmole) and in sodium hydroxide (63 ml.) are added over 15 minutes with vigorous stirring to the light brown mixture. The resulting emulsion is allowed to react in the cold for 2 hours. Then the aqueous layer is separated, washed with ether (30 ml.), acidified to pH of 1.5 with concentrated HCl, and extracted with ethyl acetate (3×40 ml.). The organic layers are combined, washed with brine (100 ml.), dried over sodium sulfate, and concentrated in vacuo to give 4.57 g. of (±)-3-hydroxy-N-[2-(acetyl-thiomethyl) -1-oxo-3-phenylpropyl]-L-tyrosine as a yellow gum.

Concentrated ammonia (9.2 ml.) is added to a stirred solution of the acetylthio product (4.57 g., 10.95 mmole) in methanol (17 ml.) under nitrogen. The mixture is stirred for 1.5 hours at room temperature, then poured into water (120 ml.), and washed with ether (2×40 ml.). The aqueous layer is acidified to pH of about 1.5 with concentrated HCl and extracted with ethyl acetate (3×40 ml.). The organic layers are combined, washed with brine (100 ml.), dried over sodium sulfate, and concentrated in vacuo to give 4.19 g. of (±)-3-hydroxy-N-[2-(mercaptomethyl)-1-oxo -3-phenylpropyl]-L-tyrosine as a light yellow-brown foam.

A solution of dicyclohexylamine (2.2 ml., 11 mmole) in ether (20 ml.) is added to a solution of this mercaptomethyl product (4.15 g., 9.94 mmole) in ether (250 ml.). The light yellow precipitate that forms is allowed to stand for 30 minutes then filtered and triturated in ether (100 ml.) to give 4.37 g. of the cyclohexylcyclohexanamine salt as a light yellow powder. The free acid is regenerated by partitioning this salt (4.02 g., 6.71 mmole) between aqueous HCl (pH of 1, 50 ml.) and ether (2×50 ml.) and ethyl acetate (50 ml.). The organic layers are collected, washed with brine (75 ml.), dried over sodium sulfate, and concentrated in vacuo to a yellow foam. This foam is allowed to dissolve in ether (100 ml.) and a solution of tert-butylamine (0.68 ml., 6.47 mmole) in ether (10 ml.) is added to it. The white, curdy precipitate that forms is allowed to stand for 5 minutes, then triturated with ether (2×100 ml.), filtered, and dried in vacuo to give 2.88 g. of (±)-3-hydroxy-N-[2-(mercaptomethyl)-1-oxo-3-phenylpropyl] -L-tyrosine, 1,1-dimethylethanamine salt (1:1) as a white powder; m.p. decomposes above 68°. TLC (silica gel; butanol:acetic acid:water, 4:1:1) $R_f$=0.79.

Anal. calc'd. for $C_{19}H_{21}NO_5S \cdot C_4H_{11}N$ C, 61.58; H, 7.19; N, 6.24; S, 7.15 Found: C, 61.68; H, 7.22; N, 6.02; S, 5.73.

EXAMPLE 25

(±)-N-(3-Mercapto-2-methyl-1-oxopropyl)-L-alanine, N-cyclohexylcyclohexanamine salt (1:1)

Thionyl chloride (72.6 ml., 1 mole) is added with stirring to a cooled (5°) suspension of (L)-alanine (44.55 g., 0.5 mole) in methanol (300 ml.). The reaction is allowed to proceed for 16 hours while warming to room temperature. The solvent and excess thionyl chloride are distilled off in vacuo to give 69.58 g. of (L)-alanine, methyl ester, hydrochloride salt; m.p. 108°–111.5°.

3-Acetylthio-2-methylpropanoyl chloride (3.61 g., 20 mmole) is added with vigorous stirring over 10 minutes to a chilled suspension of (L)-alanine, methyl ester, hydrochloride (2.85 g., 20 mmole) and triethylamine (5.76 g.) in methylene chloride (75 ml.). The mixture is allowed to react in the cold for 4 hours. It is then extracted sequentially with 10% HCl (40 ml.), saturated sodium bicarbonate (40 ml.) and brine (75 ml.), dried over sodium sulfate, and concentrated in vacuo to give 4.85 g. of (±)-N-[3-(acetylthio)-2-methyl-1-oxopropyl]-L -alanine, methyl ester as a yellow oil.

1N Sodium hydroxide (40.38 ml.) is added to a stirred, chilled (–5°) solution of this acetylthio product (4.59 g., 18.59 mmole) in methanol (30 ml.) under argon while maintaining the temperature below 5°. The solution is stirred for 3 hours in the cold, then poured into water (150 ml.), and washed with ethyl acetate. The aqueous layer is acidified to a pH of about 1.5 with concentrated HCl and extracted with ethyl acetate (3×40 ml.). The organic layers are combined, dried over sodium sulfate, and concentrated in vacuo to give 3.09 g. of (±)-N-(3-mercapto -2-methyl-1-oxopropyl)-L-alanine as a yellow oil.

Dicyclohexylamine (2.45 ml.) is added to a solution of this mercapto product (2.14 g., 11.19 mmole) in ethyl acetate (30 ml.). Upon standing for 16 hours at 4°, a white crystalline mass forms which is filtered and dried in vacuo to give 3.34 g. of (±)-N-(3-mercapto-2-methyl-1-oxopropyl)-L -alanine, N-cyclohexylcyclohexanamine salt (1:1) as a white powder; m.p. 149°–153°. TLC (silica gel; butanol:acetic acid:water, 4:1:1) $R_f$=0.66 and 0.50.

Anal. calc'd. for $C_7H_{13}NO_3S \cdot C_{12}H_{23}N$: C, 61.25; H, 9.74; N, 7.52; S, 8.61 Found: C, 61.10; H, 9.85; N, 7.40; S, 8.38.

EXAMPLE 26

(±)-$N^2$-[2-(Mercaptomethyl)-1-oxo-3-phenylpropyl]-$N^6$-[(phenylmethoxy)carbonyl]-L-lysine, N-cyclohexylcyclohexanamine salt (1:1)

Thionyl chloride (12.19 ml., 177.7 mmole) is added with stirring to a chilled (–10°) suspension of $N^6$-[(phenylmethoxy)carbonyl]-L-lysine (24.92 g., 88.9 mmole) in methanol (150 ml.) while maintaining the temperature below –5°. The resulting slurry is stirred for 16 hours while allowing the temperature to rise to room temperature. The mixture is concentrated in vacuo to a yellow oil which crystallizes to a light yellow mass. Trituration from ether gives 28 g. of $N^6$-[(phenylmethoxy)carbonyl]-L-lysine, methyl ester, hydrochloride.

3-Acetylthio-2-benzylpropanoyl chloride (12.84 g., 50 mmole) is added to a stirred, chilled (–10°) suspension of $N^6$-[(phenylmethoxy)carbonyl]-L -lysine, methyl ester, hydrochloride (14.72 g., 50 mmole) and diisopropylethylamine (18.3 ml., 110 mmole) in methylene chloride (300 ml.) while maintaining the temperature below 0°. The mixture is allowed to react for 3 hours in the cold. It is then poured into additional methylene chloride (200 ml.), washed successively with 10% HCl (100 ml.), saturated sodium bicarbonate (100 ml.), and brine (150 ml.), dried over sodium sulfate, and concentrated in vacuo to give 26.12 g. of (±)-$N^2$-[2-(acetylthiomethyl)-1-oxo-3-phenylpropyl]-$N^6$-

[(phenylmethoxy)carbonyl]-L-lysine, methyl ester as a brown solid.

A solution of 1N sodium hydroxide (104.7 ml., 104.7 mmole) is added to a stirred, chilled (−8°) solution of this acetylthiomethyl product (26.04 g., 49.9 mmole) in methanol (250 ml.) under nitrogen while maintaining the temperature below 0°. After the mixture is stirred for 3 hours in the cold, it is concentrated in vacuo to about a quarter of its volume and poured into water (400 ml.). 4N Sodium hydroxide is added bringing the solids into solution which is then washed with ethyl acetate (2×100 ml.), acidified to pH of about 2 with concentrated HCl, and extracted with ethyl acetate (3×70 ml.). The organic layers are combined, washed with brine (100 ml.), dried over sodium sulfate, and concentrated in vacuo to give 20.51 g. of (±)-$N^2$-[2-(mercaptomethyl)-1-oxo-3-phenylpropyl]-$N^6$-[(phenylmethoxy)carbonyl]-L-lysine as a brown foam.

Dicyclohexylamine (0.84 ml.) is added to a solution of this mercaptomethyl product (1.7 g., 3.82 mmole) in ethyl acetate and ether. The yellow gum that forms is solidified by the addition of hexane, and triturated from hexane to a light yellow powder (2.05 g.). A portion (1.6 g.) is recrystallized from ether/benzene/hexane to yield 1.41 g. of white solid (±)-$N^2$-[2-(mercaptomethyl)-1-oxo-3-phenylpropyl]-$N^6$-[(phenylmethoxy)carbonyl]-L-lysine, N-cyclohexylcyclohexanamine salt (1:1); m.p. decomposes above 66°. TLC (silica gel; butanol:acetic acid:water, 4:1:1) $R_f$=0.78.

Anal. calc'd. for $C_{24}H_{30}N_2O_5S \cdot C_{12}H_{23}N$: C, 67.57; H, 8.35; N, 6.57; S, 5.01 Found: C, 67.19; H, 8.22; N, 6.37; S, 4.80.

EXAMPLE 27

(±)-N-[2-(Mercaptomethyl)-1-oxo-3-phenylpropyl]-L-alanine

3-Acetylthio-2-benzylpropanoyl chloride and (L)-alanine, methyl ester, hydrochloride are reacted in the presence of triethylamine according to the procedure of Example 25 to give (±)-N-[2-(acetyl-thiomethyl)-1-oxo-3-phenylpropyl]-L-alanine, methyl ester.

A chilled, stirred solution of this methyl ester product in methanol is treated with 1N sodium hydroxide under argon and worked up as described in Example 25 to give (±)-N-[2-(mercaptomethyl)-1-oxo-3-phenylpropyl]-L-alanine as a white powder; m.p. 119.5°–124.5°. TLC (silica gel; benzene:acetic acid, 4:1) $R_f$=0.21, 0.23 (superimposed).

Anal. calc'd. for $C_{13}H_{17}NO_3S$: C, 58.40; H, 6.41; N, 5.24; S, 11.99 Found: C, 58.27; H, 6.59; N, 5.14; S, 11.00.

EXAMPLE 28

(±)-N-[2-(Mercaptomethyl)-1-oxo-3-phenylpropyl]-L-tryptophan, 1,1-dimethylethanamine salt (1:1)

3-Acetylthio-2-benzylpropanoyl chloride and (L)-tryptophan, methyl ester, hydrochloride are reacted in the presence of diisopropylethylamine according to the procedure of Example 26 to give (±)-N-[2-(acetylthiomethyl)-1-oxo-3-phenylpropyl]-L-tryptophan, methyl ester.

1N Sodium hydroxide is added to a stirred, chilled (−10°) solution of this methyl ester product in methanol and worked up according to the procedure of Example 26 to give (±)-N-[2-(mercaptomethyl)-1-oxo-3-phenylpropyl]-L-tryptophan as a light brown foam.

Tert-Butylamine in ether is added to a solution of this mercaptomethyl product in ether. Work up according to the procedure of Example 24 gives (±)-N-[2-(mercaptomethyl)-1-oxo-3-phenylpropyl]-L-tryptophan, 1,1-dimethylethanamine salt (1:1); m.p. decomposes above 74°. TLC (silica gel; butanol:acetic acid:water, 4:1:1) $R_f$=0.73.

Anal. calc'd. for $C_{21}H_{22}N_2O_3S \cdot C_4H_{11}N$: C, 65.39; H, 7.24; N, 9.15; S, 6.98 Found: C, 65.38; H, 7.54; N, 9.08; S, 5.91.

EXAMPLE 29

(±)-N-[2-(Mercaptomethyl)-1-oxo-3-phenylpropyl]-L-tyrosine

3-Acetylthio-2-benzylpropanoyl chloride and (L)-tyrosine, methyl ester, hydrochloride are reacted in the presence of diisopropylethylamine according to the procedure of Example 26 to give (±)-N-[2-(acetyl-thiomethyl)-1-oxo-3-phenylpropyl]-L-tyrosine, methyl ester.

1N Sodium hydroxide is added to a stirred, chilled (−10°) solution of this methyl ester product in methanol and worked up according to the procedure of Example 26 to give (±)-N-[2-(mercapto-methyl)-1-oxo-3-phenylpropyl]-L-tyrosine as a yellow foam.

Tert-Butylamine (1.1 ml.) is added to a solution of this mercaptomethyl product (3.41 g., 9.49 mmole) in ether. The yellow gum that forms is further precipitated by the addition of hexane. Trituration in ligroin (2×50 ml.) gives 3.15 g. of (±)-N-[2-(mercaptomethyl)-1-oxo-3-phenylpropyl]-L-tyrosine, 1,1-dimethylethanamine salt.

This salt (2.5 g., 5.78 mmole) is partitioned between 10% HCl and ethyl acetate (3×30 ml.). The organic layers are combined and washed with water (50 ml.) and brine (80 ml.), dried over sodium sulfate, and concentrated in vacuo. The residue, a yellow foam, is taken up in ether (40 ml.) and dicyclohexylamine (1.24 ml., 6.22 mmole) in ether (10 ml.) is added to it. A yellow gum forms which is solidified by the addition of hexane to give 2.04 g. of (±)-N-[2-(mercaptomethyl)-1-oxo-3-phenylpropyl]-L-tyrosine, N-cyclohexylcyclohexanamine salt as an amorphous solid, m.p. decomposes above 64°.

A portion of this N-cyclohexylcyclohexanamine salt (0.6 g., 1.11 mmole) is partitioned between 0.2 N sodium hydroxide (15 ml.) and ethyl acetate (4×7 ml.). The aqueous portion is then acidified to pH of about 1 with concentrated HCl and extracted with ethyl acetate (4×10 ml.). The organic layers are combined, washed with 10% potassium bisulfate (30 ml.) and brine (30 ml.), dried over sodium sulfate, and concentrated in vacuo to give (±)-N-[2-(mercaptomethyl)-1-oxo-3-phenylpropyl]-L-tyrosine as a white foam. TLC (silica gel; benzene:acetic acid, 3.5:1) $R_f$0.23, 0.25.

Anal. calc'd. for $C_{19}H_{21}NO_4S$: C, 62.65; H, 5.96; N, 3.85; S, 8.80 Found: C, 62.65; H, 5.76; N, 3.77; S, 8.54.

EXAMPLE 30

N-[2,(Mercaptomethyl)-1-oxo,3-phenylpropyl]-L-norleucine (isomer B)

(L)-Norleucine (2.62 g., 20 mmole) is suspended in a solution of 95% ethanol (30 ml.) and 1N sodium hydroxide (7 ml.) and chilled to −10°. 3-Acetylthio-2-benzylpropanoyl chloride (5.32 g., 20 mmole) and 1N sodium hydroxide (14 ml.) are added with vigorous stirring in 5 equal portions over 20 minutes. The mixture is then stirred for 1.5 hours in the cold, poured into water, the pH is adjusted to about 9 with 2N potassium carbonate, and extracted with ethyl acetate (3×7 ml.). The aqueous layer is then acidified to pH of about 1.5 with concentrated HCl, and extracted with ethyl acetate (3×50 ml.). The organic layers are combined, washed with brine, dried over sodium sulfate and concentrated in vacuo to give 3.9 g. of (±)-N-[2-(acetylthiomethyl)-1-oxo- 3-phenylpropyl]-L-norleucine as a yellow oil.

1N Sodium hydroxide (14.4 ml.) is added to a chilled (−10°) solution of the above acetylthiomethyl product (3.48, 9.6 mmole) in methanol (20 ml.) with thorough stirring under nitrogen while maintaining the reaction temperature below 0°. The mixture is stirred for 3.5 hours in the cold, then partially concentrated in vacuo, poured into water (200 ml.), and washed with ethyl acetate (3×50 ml.). The aqueous layer is acidified to pH of about 1.5 with concentrated HCl and extracted with ethyl acetate (3×40 ml.). The organic layers are combined, washed with brine (100 ml.), dried over sodium sulfate, and concentrated in vacuo to give 2.99 g. of (±)-N-[2-(mercaptomethyl) -1-oxo-3-phenylpropyl]-L-norleucine as a yellow oil that begins to crystallize on standing.

The above mercaptomethyl product (2.99 g., 9.57 mmole) is applied to a chromatographic column (E. Merck silica gel, 230–400 mesh, 260 g.) and eluted under pressure with (8:1) toluene:acetic acid. Fractions numbered 36–40 (30–40 ml. each) are pooled and concentrated in vacuo to give 0.18 g. of the desired product. Recrystallization from benzene/hexane gives 0.13 g. of N-[2-(mercapto-methyl) -1-oxo-3-phenylpropyl]-L-norleucine (isomer B); m.p. decomposes above 105°; $[\alpha]_D$=56.8° (c=1.0, methanol). TLC (silica gel; benzene:acetic acid, 4:1) $R_f$=0.26.

Anal. calc'd. for $C_{16}H_{23}NO_3S$: C, 62.11; H, 7.49; N, 4.53; S, 10.36 Found: C, 61.96; H, 7.49; N, 4.42; S, 10.03.

EXAMPLE 31

N-[2,(Mercaptomethyl)-1-oxo-3-phenylpropyl]-L-phenylalanine (isomer A)

3-Acetylthio-2-benzylpropanoyl chloride (2.57 g., 10 mmole) is added to a chilled (−5°), stirred suspension of (L)-phenylalanine, methyl ester, hydrochloride (2.37 g., 11 mmole) and triethylamine (3.07 ml., 22 mmole) in methylene chloride (60 ml.) while maintaining the temperature below 0°. The mixture is allowed to react in the cold for 3 hours, then poured into additional methylene chloride (60 ml.), then washed sequentially with 10% HCl (30 ml.), saturated sodium bicarbonate (30 ml.), and brine (50 ml.), then dried over sodium sulfate, and finally concentrated in vacuo to give 4.02 g. of (±)-N-[2 -(acetylthiomethyl)-1-oxo-3-phenylpropyl]-L-phenylalanine, methyl ester.

A solution of this methyl ester product (13.36 g., 29.4 mmole) in a small amount of (2.5:1) hexane:ethyl acetate is applied to silica gel (1.5 kg., 230–400 mesh) and eluted under pressure with (2.5:1) hexane: ethyl acetate. A portion of the high $R_f$ isomer (2.81 g.) is isolated. The residue from the first chromatography (8.17 g.) is then applied to a Waters 500 preparative L.C. using two silica cartridges and eluting with (3.5:1) hexane:ethyl acetate. An additional 2.36 g. of the high $R_f$ isomer is obtained and pooled with the first batch to give 5.17 g. of white, crystalline N-[2 -(acetylthiomethyl)-1-oxo-3-phenylpropyl]-L-phenylalanine, methyl ester (isomer A); m.p. 95°–98.5°.

1N Sodium hydroxide (25.3 ml.) is added with thorough stirring to a solution of the above methyl ester (isomer A) product (5.02 g., 12.57 mmole) in methanol (30 ml.) chilled to −10° under nitrogen. The solution, which solidifies on the addition of the sodium hydroxide, is allowed to warm to 10° and is stirred at this temperature for 3 hours. The mixture is then partially concentrated in vacuo and poured into water (150 ml.), basified to pH of about 10 with 1N sodium hydroxide, and washed with ether (2×80 ml.). The aqueous portion is separated, acidified to pH of about 1.5 with concentrated HCl, and extracted with ethyl acetate (3×60 ml.). These extracts are washed with 50% saturated sodium chloride solution (100 ml.), dried over sodium sulfate, and concentrated in vacuo to a white solid (4.16 g.). This material is dissolved in benzene, cooled with the addition of hexane resulting in a gel, which is filtered and dried in vacuo to give 3.66 g. of N-[2-(mercaptomethyl)-1-oxo-3-phenylpropyl]-L-phenylalanine (isomer A) as a white solid; m.p. 98°–103°; $[\alpha]_D$=+19.5° (c=1, methanol). TLC (silica gel; chloroform:acetic acid, 10:1) $R_f$=0.56.

Anal. calc'd. for $C_{19}H_{21}NO_3S$: C, 66.43; H, 6.16; N, 4.08; S, 9.33

Found: C, 66.71; H, 6.32; N, 3.93; S, 9.30.

EXAMPLE 32

N-[2-( Mercaptomethyl-1-oxo-3-phenylpropyl]-L-phenylalanine (isomer B)

Employing the chromatographic separation described in Example 31, one obtains 4.66 g. of white solid N-[2-(acetylthiomethyl)-1-oxo-3-phenylpropyl]-L-phenylalanine, methyl ester (isomer B); m.p. 75.5°–79°.

Treatment of a solution of this methyl ester product in methanol with 1N sodium hydroxide and work up according to the procedure of Example 31 gives 2.7 g. of N-[2-(mercaptomethyl)-1-oxo-3-phenylpropyl]-L-phenylalanine (isomer B) as a white foam; $[\alpha]_D$=−9.0° (c=1, methanol). TLC (silica gel; chloroform:acetic acid, 10:1) $R_f$=0.42.

Anal. calc'd. for $C_{19}H_{21}NO_3S \cdot 0.31\ H_2O$: C, 65.38; H, 6.24; N, 4.01; S, 9.19

Found: C, 65.49; H, 6.21; N, 3.87; S, 9.07.

EXAMPLE 33

(±)-N-[2-(Mercaptomethyl)-4-methyl-1-oxopentyl]-L-phenylalanine

2-Acetylthiomethyl-4-methylpentanoyl chloride and (L)-phenylalanine, ethyl ester are reacted in methylene chloride in the presence of diisopropylethylamine at a temperature below 0° according to the procedure of Example 26 to yield (±)-N-[2-(acetylthiomethyl)- 4-methyl-1-oxopentyl]-L-phenylalanine, ethyl ester as an off-white foam.

A solution of this ethyl ester product in methanol is treated with 1N sodium hydroxide at a temperature below 0° and worked up according to the procedure of Example 26 to give (±)-N-[2-(mercaptomethyl)- 4-methyl-1-oxopentyl]-L-phenylalanine as a clear viscous oil. TLC (silica gel; benzene:acetic acid, 4:1) $R_f$=0.12, 0.17.

Anal. calc'd. for $C_{16}H_{23}NO_3S$: C, 62.11; H, 7.49; N, 4.53; S, 10.36

Found: C, 61.81; H, 7.30; N, 4.35; S, 10.14.

EXAMPLE 34

(±)-N-[2-(Mercaptomethyl)-4-methyl-1-oxopentyl]-L-leucine

2-Acetylthiomethyl-4-methylpentanoyl chloride and (L)-leucine, ethyl ester are reacted in methylene chloride in the presence of diisopropylethylamine at a temperature below 0° according to the procedure of Example 26 to yield (±)-N-[2-(acetylthiomethyl)-4-methyl- 1-oxopentyl]-L-leucine, ethyl ester.

A solution of this ethyl ester product in methanol is treated with 1N sodium hydroxide at a temperature below 0° and worked up according to the procedure of Example 26 to give (±)-N-[2-(mercaptomethyl)- 4-methyl-1-oxopentyl]-L-leucine as a yellow solid. TLC (silica gel; chloroform:acetic acid, 10:1) $R_f$=0.30, 0.39.

Anal. calc'd. for $C_{13}H_{25}NO_3S$: C, 56.69; H, 9.15; N, 5.09; S, 11.64

Found: C, 56.72; H, 9.05; N, 4.99; S, 11.44.

EXAMPLE 35

(±)-N-[2-(Mercaptomethyl)-4-methyl-1-oxopentyl]-L-tryptophan

2-Acetylthiomethyl-4-methylpentanoyl chloride and (L)-tryptophan, methyl ester are reacted in methylene chloride in the presence of diisopropylethylamine at a temperature below 0° according to the procedure of Example 26 to yield (±)-N-[2-(acetylthiomethyl)- 4-methyl-1-oxopentyl]-L-tryptophan, methyl ester.

A solution of this methyl ester product in methanol is treated with 1N sodium hydroxide at a temperature below 0° and worked up according to the procedure of Example 26 to give (±)-N-[2-(mercaptomethyl)- 4-methyl-1-oxopentyl]-L-tryptophan as an amorphous yellow solid. TLC (silica gel; chloroform: acetic acid, 8:1) $R_f$=0.19, 0.25.

Anal. calc'd. for: $C_{18}H_{24}N_2O_3S \cdot 0.47\ H_2O$: C, 60.57; H, 6.78; N, 7.84; S, 8.98

Found: C, 60.98; H, 7.01; N, 7.40; S, 8.80.

EXAMPLE 36

N-[2-(Mercaptomethyl)-1-oxo-3-phenylpropyl]-L-leucine (isomer B)

In the procedure of Example 1, fractions containing the slower moving isomer are pooled and concentrated to yield N-[2-(acetylthiomethyl)- 1-oxo-3-phenylpropyl]-L-leucine, methyl ester (isomer B). Treatment with sodium hydroxide as described in Example 1 yields white, crystalline solid N-[2-(mercaptomethyl)-1-oxo-3-phenylpropyl]-L-leucine (isomer B); m.p. 143°–145°; $[\alpha]_D$=75.7° (c=0.89, methanol). TLC (silica gel; benzene:acetic acid, 4:1) $R_f$=0.38. TLC (silica gel, chloroform:acetic acid, 15:1) $R_f$=0.25, Anal. calc'd. for $C_{16}H_{23}NO_3S$: C, 62.11; H, 7.49; N, 4.53; S, 10.36

Found: C, 62.01; H, 7.49; N, 4.49; S, 10.32.

EXAMPLE 37

(R)-N-(2-Mercapto-1-oxo-3-phenylpropyl)-L-leucine, N-Cyclohexylcyclohexanamine salt (1:1)

Sodium nitrite (32.75 g., 482 mmole) is added over a period of one hour to a cooled solution of (L)-phenylalanine (51 g., 309 mmole) and potassium bromide (125 g.) in sulfuric acid (2.5 N, 620 ml.) while maintaining the reaction mixture at 0°. The mixture is stirred for an additional hour at 0°, and then for one hour at room temperature. The reaction solution is extracted with ether, back extracted with water, and the ether layer is dried over sodium sulfate. The ether is removed in vacuo, and distillation of the oily residue gives 44.9 g. of (S)-2-bromo-3-phenylpropionic acid; b.p. 142°–144° (0.25 mm of Hg.). A mixture of thiolacetic acid (8.7 ml., 121.5 mmole) and potassium hydroxide (6.8 g., 121.5 mmole) in acetonitrile (225 ml.) is stirred under argon at room temperature for 75 minutes. The mixture is cooled in an ice bath and a solution of (S)-2-bromo-3-phenylpropionic acid (25.3 g., 110.5 mmole) in acetonitrile (25 ml.) is added over a 10 minute period. The reaction is stirred under argon at room temperature for 5 hours, filtered, and the acetonitrile is removed in vacuo. The oily residue is redissolved in ethyl acetate and washed with 10% potassium bisulfate and water. Removal of the ethyl acetate in vacuo gives 24 g. of the crude product. This crude product is purified by converting it to its dicyclohexylamine salt using isopropyl ether as the solvent for crystallization to give (R)-2-acetylthio- 3-phenylpropionic acid, N-cyclohexylcyclohexanamine salt (1:1).

The above salt (2.83 g., 7.0 mmole) is suspended in water (50 ml.), acidified with concentrated HCl to pH of about 1.0, and extracted with ethyl acetate (3×25 ml.). The combined organic extracts are washed with 0.1N HCl (30 ml.) and brine (30 ml.), dried over sodium sulfate, and concentrated in vacuo to a clear, light yellow oil. Dicyclohexylcarbodiimide (1.44 g., 7.0 mmole) in tetrahydrofuran (10 ml.) is added to a chilled (−5°) solution of this oil, (L)-leucine, 1,1-dimethylethyl ester (1.31 g., 7.0 mmole), and hydroxybenzotriazole hydrate (0.95 g., 7.0 mmole) in tetrahyrofuran (50 ml.). The mixture is stirred overnight, warming to room temperature. The mixture is filtered and the filtrate is concentrated, taken up in ethyl acetate (60 ml.), filtered, washed with saturated sodium bicarbonate, 10% potassium bisulfate, and brine (30 ml. each), dried over sodium sulfate, and concentrated in vacuo to a clear, yellow oil. This oil is applied to column of silica gel (15 g., 230–400 mesh) and eluted with (1:1) ether:hexane (100 ml.). The eluant is concentrated in vacuo to give 2.49 g. of (R)-N-[2-(acetylthio)-1-oxo-3-phenylpropyl]-L-leucine, 1,1-dimethylethyl ester as a clear, light yellow oil. $[\alpha]_D$=+24.7° (c=1, methanol).

Trifluoroacetic acid (2.0 ml.) in methylene chloride (5 ml.) is added to a mixture of (R)-N-[ 2-(acetylthio)-1-oxo-3-phenylpropyl]-L-leucine,1,1-dimethylethyl ester (1.88 g., 5.09 mmole) and anisole (0.1 ml.). The mixture is stirred overnight under a drying tube. Afterwards, the mixture is concentrated in vacuo, toluene (10 ml.) is added, and the mixture is again concentrated (twice). The pink residue is taken up in isopropyl ether and dicyclohexylamine (0.86 ml., 5.21 mmole) is added. A white precipitate forms and is filtered off. The mother liquors are concentrated and the residue is taken up in ethyl acetate (40 ml.) and washed with 10% potassium bisulfate (2×20 ml.), water (20 ml.) and saturated sodium bicarbonate (3×20 ml.). The aqueous basic portions are combined, acidified to pH of about 2 with concentrated HCl, and extracted with ethyl acetate (3×30 ml.). The organic layers are combined, washed with brine (30 ml.), dried over sodium sulfate, and concentrated in vacuo to give 1.47 g. of (R)-N-[2-(acetylthio)- 1-oxo-3-phenylpropyl]-L-leucine as a clear, light yellow oil.

A solution of this oil (0.9 g., 2.87 mmole) in methanol (5 ml.) is flushed with nitrogen and chilled to −10°. Concentrated ammonia (5 ml.) is added dropwise over 10 minutes and the mixture is stirred for 2 hours and then concentrated in vacuo. The residue is taken up in water (40 ml.) and the pH is adjusted to about 8.5 with 0.1N sodium hydroxide, washed with ethyl acetate (2×20 ml.), acidified to pH of about 3 with 1N HCl, and extracted with ethyl acetate (3×20 ml.). These layers are combined and concentrated to a yellow oil (0.93 g.). A portion of this oil (0.73 g.) is taken up in isopropyl ether (80 ml.)(gentle warming) and dicyclohexylamine (0.56 ml., 2.8 mmole) in warm isopropyl ether is added. Hexane (80 ml.) is added and the mixture is chilled overnight in a freezer. The white precipitate that forms is filtered, washed with 50% isopropyl etherhexane (3×), and dried in vacuo to give 0.87 g. of (R)-N-(2-mercapto-1-oxo-3-phenylpropyl)-L-leucine, N-cyclohexylcyclohexanamine salt (1:1); m.p. 176°–178°; $[\alpha]_D$=–28.6° (c=1, methanol). TLC (silica gel; benzene:acetic acid, 4:1) $R_f$=0.17, 0.37 (lower spot due to the dicyclohexylamine).

Anal. calc'd. for $C_{15}H_{21}NO_3S \cdot C_{12}H_{23}N \cdot 0.3\ H_2O$: C, 67.26; H, 9.32; N, 5.81; S, 6.65
Found: C, 67.36; H, 9.20; N, 5.83; S, 6.41.

EXAMPLE 38

(S)-N-( 2-Mercapto-1-oxo-3-phenylpropyl)-L-leucine, N-cyclohexylcyclohexanamine salt (1:1)

Following the procedure of Example 37 but employing D-phenylalanine, one obtains (R)-2-bromo- 3-phenylpropionic acid. Treatment of this acid with thiolacetic acid and potassium hydroxide and work up according to the procedure of Example 37 gives (S)- 2-acetylthio-3-phenylpropionic acid, N-cyclohexylcyclohexanamine salt (1:1).

This salt is converted to the free acid. Dicyclohexylcarbodiimide in tetrahydrofuran is added to a solution of (S)-2-acetylthio-3-phenylpropionic acid, (L)-leucine, 1,1-dimethylethyl ester, and hydroxybenzotriazole hydrate in tetrahydrofuran at –8° and the reaction mixture is stirred overnight warming to room temperature, and is then worked up according to the procedure of Example 37 to yield (S)-N-[2-(acetylthio)-1-oxo-3-phenylpropyl]-L-leucine, 1,1-dimethylethyl ester as a clear, light yellow, viscous oil.

A portion of this oil (2.05 g., 5.21 mmole) is flushed with argon and treated with cold (–5°). 5% anisole in trifluoroacetic acid (10.25 ml.). The mixture is stirred for 30 minutes at 0°, and then allowed to warm to room temperature over one hour. The solution is concentrated in vacuo, toluene (30 ml.) is added and removed in vacuo, and the residue is dried overnight under vacuum. The majority of this material (95Z) is dissolved in methanol (5 ml.), and chilled to 0° under nitrogen. Concentrated ammonia (5 ml.) is added dropwise over 10 minutes, and the mixture is stirred overnight warming to room temperature. The mixture is then poured into water (150 ml.), acidified to pH of about 2 with 1N HCl, and extracted with ethyl acetate (3×30 ml.). The organic layers are combined and washed with 0.1N HCl, water and brine (30 ml. each), then dried over sodium sulfate, and concentrated in vacuo. The clear, yellow, viscous residue is taken up in isopropyl ether (60 ml.) and a warm solution of dicyclohexylamine (0.99 ml., 6 mmole) in isopropyl ether (10 ml.) is added. The mixture is allowed to stand overnight at 4° under a blanket of argon. The resulting white precipitate is filtered, washed with isopropyl ether (twice), and dried to give 1.94 g. of white solid (S)-N-(2-mercapto-1-oxo-3-phenylpropyl)-L-leucine, N-cyclohexylcyclohexanamine salt (1:1); m.p. 161.5°–163°; $[\alpha]_D$=–18.0° (c=1 methanol) TLC (silica gel; benzene:acetic acid, 4:1) $R_f$=0.17, 0.41 (lower spot due to the dicyclohexylamine).

Anal calc'd. for $C_{15}H_{21}NO_3S \cdot C_{12}H_{23}N \cdot 0.53\ H_2O$: C, 66.69; H, 9.34; N, 5.76; S, 6.59
Found: C, 66.69; H, 8.98; N, 5.72; S, 6.46.

EXAMPLE 39

(S)-N-(3-Mercapto-2-methyl-1-oxopropyl)-L-phenylalanine (D)-3-Acetylthio-2-methylpropanoyl chloride (2.4 g., 13.3 mmole) in dry methylene chloride (35 ml.) is added dropwise to a stirred, cooled (–5°), suspension of (L)-phenylalanine, methyl ester, hydrochloride (3.15 g., 14.6 mmole) and diisopropylethylamine (3.86 g., 29.9 mmole) in dry methylene chloride (3 ml.) under nitrogen. After the addition is complete, the reaction is stirred in the cold for an additional 2.5 hours, and then allowed to warm to room temperature overnight. The reaction mixture is concentrated in vacuo. The residue is dissolved in ethyl acetate (125 ml.) and washed with 20 ml. portions of 10% aqueous potassium bisulfate, water, 5% aqueous sodium bicarbonate, water, and brine, then dried over magnesium sulfate, and concentrated in vacuo to give 4.3 g. of crude material. Flash chromatography on silica gel (430 g.) eluting with (3:1) hexanes: ethyl acetate gives 3.8 g. of (S)-N-[3-(acetylthio)- 2-methyl-1-oxopropyl]-L-phenylalanine, methyl ester as a light yellow oil.

A solution of this methyl ester product (3.7 g., 11.4 mmole) in methanol (70 ml.) is cooled in an ice bath under nitrogen and treated dropwise with 1N sodium hydroxide solution (34.3 ml., 34.3 mmole). After the addition is completed, the reaction mixture is stirred in the cold for 15 minutes, then allowed to warm to ambient temperature overnight. The reaction mixture is concentrated in vacuo to remove all of the methanol and the remaining aqueous solution is diluted with water (100 ml.) and washed with chloroform (2×35 ml.). The organic washes are concentrated in vacuo and the residue is dissolved in 1N sodium hydroxide (75 ml.) and washed with chloroform. The aqueous layers are combined and acidified to pH 1 with concentrated HCl and then extracted with ethyl acetate (3×100 ml.). The combined organic extract is washed successively with 75 ml. of water and brine, dried over magnesium sulfate, and concentrated in vacuo to give 3.25 g. of crude product. Flash chromatography on silica gel (325 go) eluting with (40:1:1) chloroform: methanol:acetic acid gives 2.75 g. of white solid (S)-N-(3-mercapto-2-methyl- 1-oxopropyl)-L-phenylalanine; m.p. 108°–109°; $[\alpha]_D$=7.0° (c=1, methanol). TLC (silica gel; chloroform:methanol:acetic acid, 30:1:1) $R_f$=0.24. Anal. calc'd. for $C_{13}H_{17}NO_3S$: C, 58.40; H, 6.41; N, 5.24; S, 11.99
Found: C, 58.31; H, 6.36; N, 5.11; S, 11.68.

EXAMPLE 40

(S),N-(3-Mercapto-2-methyl-1-oxopropyl)-L-leucine

Following the procedure of Example 39 but employing (L)-leucine, methyl ester, hydrochloride, one obtains white solid (S)-N-(3-mercapto-2-methyl- 1-oxopropyl)-L-leucine; m.p. 66°–71°; $[\alpha]_D$= –70.8° (c=1, methanol). TLC (silica gel; benzene: acetic acid, 4:1) $R_f$=0.24.

Anal. calc'd. for $C_{10}H_{19}NO_3S$: C, 51.47; H, 8.21; N, 6.00; S, 13.74
Found: C, 51.28; H, 8.17; N, 5.95; S, 13.76.

EXAMPLE 41

(S)-N-(3-Mercapto-2-methyl-1-oxopropyl)-L-threonine (L)-Threonine (5.0 g., 42 mmole) and sodium bicarbonate (9.8 g., 92 mmole) are dissolved in water (100 ml.) and p-dioxane (80 ml.) is added. The cloudy mixture is cooled to 0° and the pH is adjusted to 8. (D)-3-Acetylthio-2-methylpropanoyl chloride (7.52 ml., 50.4 mmole) is added dropwise over 2 hours while the pH is maintained at 8 by the addition of 1M sodium hydroxide. After the addition is completed, the reaction is allowed to stir for 30 minutes and then washed with ether (2×250 ml.). The aqueous phase is acidified to pH 1 with concentrated HCl and then extracted with ethyl acetate (3×250 ml.). The organic extract is dried over magnesium sulfate, filtered, and the solvent removed in vacuo to give 10.8 g. of (S)-N-[3-(acetylthio)- 2-methyl-1-oxopropyl]-L-threonine as a clear, colorless oil.

This acetylthio product (2.75 g., 10.4 mmole) is flushed with argon and dissolved in 50% concentrated ammonium hydroxide (15 ml.). The reaction is stirred for 3 hours and then washed with ether (2×20 ml.). The aqueous phase is acidified to pH 1 with concentrated HCl and then extracted with ethyl acetate (3×25 ml.). The organic extracts are dried over magnesium sulfate and the solvent is removed in vacuo to give a white semi-solid (1.68 g.). Recrystallization from acetonitrile yields 747 mg. of white crystalline solid (S)-N-(3-mercapto-2-methyl-1-oxopropyl)-L-threonine; m.p. 148°–150°; $[\alpha]_D = -39.1°$ (c=0.56, methanol). TLC (silica gel; methylene chloride:acetic acid:methanol, 8:1:1) $R_f=0.37$. Anal. calc'd. for $C_8H_{15}NO_4S$: C, 43.42; H, 6.83; N, 6.33; S, 14.49
Found: C, 43.48; H, 6.79; N, 6.43; S, 14.21.

EXAMPLE 42

(S)-N-(3-Mercapto-2-methyl-1-oxopropyl)-L-aspartic acid

Following the procedure of Example 41 but employing (L)-aspartic acid, one obtains (S)-N(3-mercapto-2-methyl-1-oxopropyl)-L-aspartic acid; m.p. 129°–131°; $[\alpha]_D=-42.6°$ (c=0.47, methanol). TLC (silica gel; methylene chloride: acetic acid: methanol, 8:1:1) $R_f=0.27$.
Anal. calc'd. for $C_8H_{13}NO_5S$: C, 40.84; H, 5.57; N, 5.96; S, 13.63
Found: C, 40.61; H, 5.68; N, 6.03; S, 13.19.

EXAMPLE 43

(S)-N-(3-Mercapto-2-methyl-1-oxopropyl)-L-isoleucine

Following the procedure of Example 41 but employing (L)-isoleucine, one obtains white crystalline (S)-N-(3-mercapto-2-methyl-1-oxopropyl)-L-isoleucine; m.p. 164°; $[\alpha]_D=-43.4°$ (c=0.53, methanol). TLC(silica gel; acetic acid:toluene, 1:9) $R_f=0.12$. Anal. calc'd. for $C_{10}H_{19}NO_3S$: C, 51.48; H, 8.21; N, 6.00; S, 13.74
Found: C, 51.53; H, 8.38; N, 5.99; S, 13.70.

EXAMPLE 44

(S)-$N^2$-(3-Mercapto-2-methyl-1-oxopropyl)-L-asparagine

Following the procedure of Example 41 but employing (L)-asparagine, one obtains (S)-$N^2$-(3-mercapto-2-methyl-1-oxopropyl)-L-asparagine; m.p. 181°; $[\alpha]_D=-25.2$ (c=0.5, methanol). TLC ( silica gel; methylene chloride :methanol: acetic acid, 4:1:1) $R_f=0.35$.
Anal. calc'd. for $C_{18}H_{14}N_2O_4S$: C, 41.01; H, 6.02; N, 11.96; S, 13.69
Found: C, 40.83; H, 6.09; N, 12.05; S, 13.97.

EXAMPLE 45

(±)-3-[[2-(Mercaptomethyl)-1-oxo-3-phenylpropyl]amino] propanoic acid

2-Acetylthiomethyl-3-phenylpropanoic acid is reacted with oxalyl choride and the resulting acid chloride is then reacted with β-alanine, ethyl ester, hydrochloride in the presence of diisopropylethylamine as more fully described in Example 1 of European Patent Application 136,883 to give (±)-3-[[2-[(acetylthio)methyl]-1-oxo-3-phenylpropyl] amino]propanoic acid, ethyl ester.

A chilled solution of this ethyl ester product in methanol is treated with 1N sodium hydroxide and worked up as described in Example 1 of European Patent Application 136,883 to give (±)-3-[[2-(mercaptomethyl)- 1-oxo-3-phenylpropyl]amino]propanoic acid as a white solid; m.p. 76°–82°. TLC (silica gel; toluene:acetic acid, 4:1) $R_f=0.37$, minor spot at 0.07.
Anal. calc'd. for $C_{13}H_{17}NO_3S$: C, 58.40; H, 6.41; N, 5.24; S, 11.99
Found: C, 58.17; H, 6.34; N, 5.15; S, 11.85.

EXAMPLE 46

(±)-4-[[2-(Mercaptomethyl)-1-oxo-3-phenylpropyl]amino] butanoic acid

2-Acetylthiomethyl-3-phenylpropanoic acid is reacted with oxalyl chloride and the resulting acid chloride is then reacted with 4-aminobutanoic acid, methyl ester, hydrochloride in the presence of diisopropylethylamine as more fully described in Example 2 of European Patent Application 136,883 to give (±)-4-[[2-[(acetylthio)methyl]-1-oxo-3-phenylpropyl] amino]butanoic acid, methyl ester.

A chilled solution of this methyl ester product in methanol is treated with 1N sodium hydroxide and worked up as described in Example 2 of European Patent Application 136,883 to give (±)-4-[[2-(mercaptomethyl)-1-oxo-3-phenylpropyl]amino] butanoic acid as a white solid; m.p. 94.5°–101°. TLC (silica gel; benzene:acetic acid, 4:1) $R_f=0.41$. Anal. calc'd. for $C_{14}H_{19}NO_3S$: C, 59.76; H, 6.81; N, 4.98; S, 11.40
Found: C, 59.81; H, 6.81; N, 4.96; S, 11.37.

EXAMPLE 47

(S)-3-[[2-(Mercaptomethyl)-1-oxo-3-phenylpropyl]-amino] benzenebutanoic acid (isomer A)

2-Acetylthiomethyl-3-phenylpropanoic acid is reacted with oxalyl chloride and the resulting acid chloride is then reacted with (S)-3-amino-4-phenylbutanoic acid, methyl ester, p-toluenesulfonic acid salt in the presence of diisopropylethylamine as more fully described in Example 3 of European Patent Application 136,883. The resulting crude product is chromatographed to give (S)-3-[[2-[(acetylthio)methyl]- 1-oxo-3-phenylpropyl]amino]benzenebutanoic acid, methyl ester (isomer A, faster moving) and (isomer B, slower moving).

A chilled solution of the methyl ester (isomer A) product in methanol is treated with 1N sodium hydroxide and worked up as described in Example 3 of European Patent Application 136,883 to give (S)-3-[[2-(mercaptomethyl)-1-oxo- 3-phenylpropyl]amino]benzenebutanoic acid (isomer A); m.p. 149°–151.5° $[\alpha]_D=+40.3°$ (c=1, methanol). TLC (silica gel; benzene:acetic acid, 7:1) $R_f=0.40$.

Anal. calc'd. for $C_{20}H_{23}NO_3S$: C, 67.20; H, 6.49; N, 3.92; S, 8.97
Found: C, 66.86; H, 6.45; N, 3.93; S, 8.71.

EXAMPLE 48

(S)-3-[[2-(Mercaptomethyl)-1-oxo-3-phenylpropyl] amino]benzenebutanoic acid (isomer B)

A chilled solution of the methyl ester (isomer B) product from Example 47 in methanol is treated with sodium hydroxide and worked up as described in Example 4 of European Patent Application 136,883 to give (S)-3-[[2-(mercaptomethyl)-1-oxo-3-phenylpropyl]amino] benzenebutanoic acid (isomer B); m.p. 148°–150°; $[\alpha]_D=-28.9°$ (c=1.07, methanol). TLC (silica gel; benzene:acetic acid, 7:1) $R_f=0.34$. Anal calc'd. for $C_{20}H_{23}NO_3S$: C, 67.20; H, 6.49; N, 3.92; S, 8.97
Found: C, 66.95; H, 6.53; N, 3.82; S, 8.82.

EXAMPLE 49

(±)-5-[[2-(Mercaptomethyl)-1-oxo-3-phenylpropyl] amino] pentanoic acid

2-Acetylthiomethyl-3-phenylpropanoic acid is reacted with oxalyl chloride and the resulting acid chloride is then reacted with 5-aminopentanoic acid, methyl ester, hydrochloride in the presence of diisopropylethylamine as more fully described in Example 5 of European Patent Application 136,883 to give (±)-5-[[2-[(acetylthio)methyl]-1-oxo-3-phenylpropyl] amino]pentanoic acid, methyl ester.

A chilled solution of this methyl ester product in methanol is treated with 1N sodium hydroxide and worked up as described in Example 5 of European Patent Application 136,883 to give (±)-5-[[2-(mercaptomethyl)-1-oxo-3-phenylpropyl]amino] pentanoic acid; m.p. 78°–79°. TLC (silica gel; benzene:acetic acid, 4:1) $R_f=0.30$ (slight tailing). Anal. calc'd. for $C_{15}H_{21}NO_3S$: C, 60.99; H, 7.17; N, 4.74; S, 10.85
Found: C, 60.80; H, 7.15; N, 4.62; S, 10.73.

EXAMPLE 50

(±)-6-[[2-(Mercaptomethyl)-1-oxo-3-phenylpropyl] amino] hexanoic acid

2-Acetylthiomethyl-3-phenylpropanoic acid is reacted with oxalyl chloride and the resulting acid chloride is then reacted with 6-aminohexanoic acid, methyl ester, hydrochloride in the presence of diisopropylethylamine as more fully described in Example 6 of European Patent Application 136,883 to give (±)-6-[[2-[(acetylthio)methyl]-1-oxo-3-phenylpropyl] amino]hexanoic acid, methyl ester.

A chilled solution of this methyl ester product in methanol is treated with 1N sodium hydroxide and worked up as described in Example 6 of European Patent Application 136,883 to give (±)-6-[[2-(mercaptomethyl)-1-oxo-3-phenylpropyl]amino]hexanoic acid, m.p. 58°–63°. TLC (silica gel; toluene:acetic acid, 4:1) $R_f=0.26$ (slight tailing).
Anal. calc'd. for $C_{16}H_{23}NO_3S \cdot 0.18\ H_2O$: C, 61.46; H, 7.53; N, 4.48; S, 10.25
Found: C, 61.46; H, 7.47; N, 4.40; S, 10.14.

EXAMPLE 51

8-[[2-(Mercaptomethyl)-1-oxo-3-phenylpropyl]amino]-octanoic acid

2-Acetylthiomethyl-3-phenylpropanoic acid is reacted with oxalyl chloride and the resulting acid chloride is then reacted with 8-aminooctanoic acid, methyl ester hydrochloride in the presence of diisopropylethylamine as more fully described in Example 11 of European Patent Application 136,883 to give (±)-8-[[2-[(acetylthio)methyl]-1-oxo-3phenylpropyl] amino]octanoic acid, methyl ester.

A chilled solution of this methyl ester product in methanol is treated with 1N sodium hydroxide and worked up as described in Example 11 of European Patent Application 136,883 to give (±)-8-[[2-(mercaptomethyl)- 1-oxo-3-phenylpropyl]amino]octanoic acid, m.p. 81°–83° (sinters above 68°). TLC (silica gel; benzene:acetic acid, 4:1) $R_f=0.42$.
Anal. calc'd. for $C_{18}H_{27}NO_3S$: C, 64.06; H, 8.06; N, 4.15; S, 9.50; SH 9.80.
Found: C, 63.77; H, 7.84; N, 4.12; S, 9.18; SH 9.66.

EXAMPLE 52

7-[[2-(Mercaptomethy1)-1-oxo-3-phenylpropyl]amino]-heptanoic acid

2-Acetylthiomethyl-3-phenylpropanoic acid is reacted with oxalyl chloride and the resulting acid chloride is then reacted with 7-aminoheptanoic acid, methyl ester, hydrochloride in the presence of diisopropylethylamine as more fully described in Example 8 of European Patent Application 136,883 to give (±)-7-[[2-[(acetylthio)methyl]-1-oxo-3-phenylpropyl] amino]heptanoic acid, methyl ester.

A chilled solution of this methyl ester product in methanol is treated with 1N sodium hydroxide and worked up as described in Example 9 of European Patent Application 136,883 to give (±)-7-[[2-(mercaptomethyl)-1-oxo-3-phenylpropyl]amino] heptanoic acid; m.p. 71°–73° (sinters above 65°). TLC (silica gel; benzene:acetic acid, 4:1) $R_f=0.36$ (trace at 0.27).
Anal. calc'd for $C_{17}H_{25}NO_3S$: C, 63.13; H, 7.79; N, 4.30; S, 9.91; SH 10.22
Found: C, 63.36; H, 7.91; N, 4.21; S, 9.57; SH 9.89.

EXAMPLE 53

(±)-11-[[2-(Mercaptomethyl)-1-oxo-3-phenylpropyl] amino] undecanoic acid

2-Acetylthiomethyl-3-phenylpropanoic acid is reacted with oxalyl chloride and the resulting acid chloride is then reacted with 11-aminoundecanoic acid, methyl ester, hydrochloride in the presence of diisopropylethylamine as more fully described in Example 12 of European Patent Application 136,883 to give (±)-11-[[2-[(acetylthio)methyl]-1-oxo-3phenylpropyl] amino]undecanoic acid, methyl ester.

A chilled solution of this methyl ester product in methanol is treated with 1N sodium hydroxide and worked up as described in Example 12 of European Patent Application 136,883 to give (±)-11-[[2-(mercaptomethyl)-1-oxo-3-phenylpropyl]-amino] undecanoic acid; m.p. 104°–105°. TLC (silica gel; benzene:acetic acid, 4:1) $R_f=0.51$.
Anal. calc'd. for $C_{21}H_{33}NO_3S$: C, 66.45; H, 8.76; N, 3.69; S, 8.45; SH, 8.71
Found: C, 66.12; H, 8.75; N, 3.65; S, 8.45; SH, 8.67.

EXAMPLE 54

N-(Mercaptoacetyl)-L-valyl-L-tryptophan, lithium salt

As described in Example 10 of Australian Patent No. 537,592, a solution of acetylthioacetic acid and hydroxybenzotriazole monohydrate in tetrahydrofuran is cooled to 0° and treated with dicyclohexylcarbodiimide in tetrahydrofuran followed by a solution of L-valyl-L-tryptophan, methyl ester, trifluoroacetate salt and N-methylmorpholine. Work up of the reaction mixture yields N-(acetylthioacetyl)-L-valyl-L-tryptophan, methyl ester.

A solution of this methyl ester product in methanol is treated with potassium hydroxide under nitrogen and worked up as described in Example 11 of Australian Patent 537,592 to give N-(mercaptoacetyl)- L-valyl-L-tryptophan, lithium salt. TLC (silica gel; methanol) $R_f$=0.71.

Anal. calc'd. for $C_{18}H_{22}N_3O_4S \cdot Li \cdot 2H_2O$: C, 51.54; H, 6.25; N, 9.43; S, 7.65; Li, 1.65
Found: C, 51.94; H, 6.03; N, 10.02; S, 7.28; Li, 1.62.

EXAMPLE 55

(±)-N-[N,[2-(Mercaptomethyl)-4-methyl-1-oxopentyl]-glycyl]-L-arginine

As described in Example 7 of U.S. Pat. No. 4,235,885, this compound can be prepared by reacting (±)-N-[2-[(acetylthio)methyl]-4-methyl-1-oxopentyl] glycine, 4-nitrophenyl ester with (L)-arginine to give (±)-N-[N-[2-[(acetylthio)methyl]-4-methyl- 1-oxopentyl]glycyl]-L-arginine. An aqueous chilled solution of this product is then treated with concentrated ammonia to give (±)-N-[N-[2-(mercaptomethyl)-4-methyl-1-oxopentyl] glycyl]-L-arginine; m.p. 132°–146°.

Anal. calc'd. for $C_{15}H_{29}N_5O_4S$: C, 47.99; H, 7.79; N, 18.65; S, 8.54 Found: C, 47.55; H, 7.99; N, 18.34; S, 8.30.

EXAMPLE 56

N-[N-[2-(Mercaptomethyl)-4-methyl-1-oxopentyl]-L-alanyl] -L-arginine (isomer A)

N-[2-(Acetylthiomethyl)-4-methyl-1-oxopentyl]-L-alanine (isomer A) (0.7 g., prepared as described in Example 12) is dissolved in tetrahydrofuran (50 ml.), cooled to −10°, and triethylamine (0.25 g.) is added. Ethyl chloroformate (0.27 g.) in tetrahydrofuran (2 ml.) is added dropwise. After stirring at −10° for 20 minutes, the reaction mixture is filtered into a precooled flask (−30°). L-Arginine (0.44 g.) dissolved in water (5 ml.) is added dropwise to a vigorously stirred solution of the mixed anhydride. The reaction mixture is stored at 0° overnight, then diluted with water (5 ml.), and then concentrated in vacuo to a 5 ml. volume. This solution is chromatographed on cellulose (90 g. of Avicel) using as the solvent system (9:1) methanol:water. The product containing fraction is concentrated in vacuo and then lyophilized to give 0.6 g. of N-[N-[2-(acetylthiomethyl)-4-methyl- 1-oxopentyl]-L-alanyl]-L-arginine (isomer A); m.p. 121°–138°; $[\alpha]_D$=−44° (c=1, 95% ethanol).

The above acetylthiomethyl product is dissolved in water (16 ml.) and purged with argon. Concentrated ammonium hydroxide (2 ml.) is added and the solution is stirred at room temperature for 45 minutes. It is then lyophilized to dryness and suspended in acetonitrile (15 ml.) with 3 drops of water. After stirring for 30 minutes, it is filtered and dried in vacuo at 45° for 3 hours to give tan solid N-[N-[2-(mercaptomethyl)- 4-methyl-1-oxopentyl]-L-alanyl]-L-arginine (isomer A); m.p. begins to soften at 115° to 143°.

Anal. calc'd. for $C_{16}H_{31}N_5O_4S \cdot 0.6H_2O$: C, 48.00; H, 8.10; N, 17.49; S, 8.01 Found: C, 47.92; H, 8.02; N, 17.15; S, 8.07.

EXAMPLE 57

N-[N-[2-(Mercaptomethlyl)-4-methyl-1-oxopentyl]-L-alanyl] -L-arginine (isomer B)

Following the procedure of Example 56 but employing N-[2-(acetylthiomethyl)-4-methyl-1-oxopentyl]-L-alanine (isomer B) (prepared as described in Example 13), one obtains N-[N-[2-(acetylthiomethyl)- 4-methyl-1-oxopentyl] -L-alanyl-L-arginine (isomer B); $[\alpha]_D$=+6.0°.

The above acetylthiomethyl product is dissolved in water and treated with concentrated ammonium hydroxide according to the procedure of Example 56 to give off-white solid N-[N-[2-(mercaptomethyl)- 4-methyl-1-oxopentyl]-L-alanyl]-L-arginine (isomer B); m.p. 140°–150°.

Anal. calc'd. for $C_{16}H_{31}N_5O_4S \cdot 0.7H_2O$: C, 47.79; H, 8.12; N, 17.42; S, 7.97 Found: C, 48.15; H, 7.94; N, 16.93; S, 7.69.

EXAMPLE 58

(±)-N-[N-[2-(Mercaptomethyl)-4-methyl-1-oxopentyl]-β-alanyl]-L-arginine

β-Alanine (1.45 g.) is dissolved in water containing sodium bicarbonate (1.37 g.). This aqueous solution is cooled to 0° and 2-acetylthiomethyl- 4-methylpentanoyl chloride (3.34 g.) in tetrahydrofuran (30 ml.) is added dropwise with the simultaneous addition of more sodium carbonate (1.37 g.) in water (30 ml.). After the addition is completed, the reaction mixture is stirred for 2 hours and concentrated in vacuo to 50 ml. The aqueous solution is acidified with 10% HCl and the product is extracted with ethyl acetate. The extract is dried over magnesium sulfte, filtered and concentrated in vacuo. The resulting oil (4.2 g.) is washed with hexane and the product is allowed to crystallize from a minimal amount of ethyl acetate (5 ml.) to give 2.6 g. of solid (±)-N-[2-(acetylthiomethyl)- 4-methyl-1-oxopentyl]-β-alanine; m.p. 87°–91°.

This β-alanine product (1.4 g.) and p-nitrophenol (0.7 g.) are dissolved in ethyl acetate (100 ml.) and cooled to −5°. Dicyclohexylcarbodiimide (1.0 g.) is added portionwise and the reaction is stirred for 4 hours at 0°. Dicyclohexyl urea is filtered off and the filtrate is concentrated in vacuo to give 2.0 g. of crude N-[2-(acetylthiomethyl)- 4-methyl-1-oxopentyl]-β-alanine, p-nitrophenyl ester.

This crude ester is dissolved in tetrahydrofuran (50 ml.) and cooled to 0°. L-Arginine (0.8 g.) dissolved in water (10 ml.) is added dropwise. After stirring overnight, the reaction mixture is concentrated in vacuo to 10 ml. This aqueous solution is washed with ethyl acetate until colorless. It is chromatographed on microcrystalline cellulose (100 g.) eluting with (1:4) water:methanol to give 0.9 g. of white solid (±)-N-[N-[ 2-(acetylthiomethyl)-4-methyl-1-oxopentyl]-β-alanyl]-L-arginine.

The above acetylthio product (0.4 g.) is dissolved in water (10 ml.), purged with argon, and cooled to 0°. Concentrated ammonium hydroxide (1.7 ml.) is added and the mixture is stirred under argon for 2 hours. This reaction mixture is lyophilized overnight. The residue is stirred with acetonitrile (30 ml.) containing 3 drops of water until the product becomes a granular solid. It is then filtered and dried in vacuo to give 0.3 g. of white solid (±)-N-[N-[2-(mercaptomethyl)-4-methyl- 1-oxopentyl]-β-alanyl]-L-arginine; m.p.123°–134°.

Anal calc'd. for $C_{16}H_{31}N_5O_4S \cdot 0.5H_2O$: C, 48.22; H, 8.09; N, 17.57; S, 8.04; SH 8.29 Found: C, 48.36; H, 7.92; N, 17.35; S, 8.10; SH 8.33.

EXAMPLE 59

(±)-$N^2$-[N-[2-(Mercaptomethyl)-4-methyl-1-oxopentyl]-glycyl] -L-glutamine, ammonium salt (1:1).

A solution of (L)-glutamine (0.58 g., 4 mmole) and sodium bicarbonate (0.34 g., 4 mmole) in water (15 ml.) is treated with solid N-[2-(acetylthiomethyl)-4-methyl-1-oxopentyl] glycine, p-nitrophenyl ester (1.5 g., 4 mmole, prepared as described in Example 7 of U.S. Pat. No. 4,235,885) followed by dioxane (10 ml.). The yellow slurry is stirred at 25° overnight and then filtered. The aqueous mixture is then extracted with ethyl acetate until colorless, then acidified with potassium bisulfate, and extracted with n-butanol. Drying over magnesium sulfate and evaporating gives an oil. Ether trituration gives 0.4 g. of solid (±)-$N^2$-[N-[2-(acetylthiomethyl)-4-methyl-1-oxopentyl]-glycyl] -L-glutamine; m.p. 60°–80°.

This acetylthiomethyl product (200 mg., 0.5 mmole) is dissolved in absolute ethanol (5 ml.), cooled in an ice bath, and treated with ammonium hydroxide (2 ml.) under argon. After warming to 25° over 2 hours, the mixture is evaporated to an oil. Trituration with acetonitrile, filtration, and ether washing gives 0.15 g. of (±)-$N^2$-[N-[2-(mercaptomethyl)-4-methyl-1-oxopentyl] glycyl]-L-glutamine, ammonium salt (1:1) as a white powder that sets to a colorless glass.

Anal. calc'd. for $C_{14}H_{25}N_3O_5S \cdot NH_3$ C, 45.57; H, 7.79; N, 15.18; S, 8.69 Found: C, 45.51, H, 7.96; N, 15.24; S, 8.32.

EXAMPLE 60

N-[N-(Mercaptoacetyl)-L-phenylalanyl]-L-alanine

A solution of dicyclohexylcarbodiimide (29.5 g., 140 mmole) in tetrahydrofuran (40 ml.) is added to a stirred, chilled (−10°) suspension of (L)-alanine, methyl ester, hydrochloride (18.15 g., 130 mmole), N-[(phenylmethoxy)carbonyl]-L-phenylalanine (38.91 g., 130 mmole), diisopropylethylamine (22.6 ml., 130 mmole), and hydroxybenzotriazole hydrate (17.52 g., 130 mmole) in tetrahydrofuran (200 ml.) while maintaining the temperature below 0°. The mixture is allowed to react overnight while warming to room temperature. It is then concentrated in vacuo, taken up in ethyl acetate, and filtered to remove dicyclohexyl urea. The filtrate is then washed with saturated sodium bicarbonate (200 ml.), 10% potassium bisulfate (200 ml.), water (200 ml.), and brine (200 ml.), then dried over sodium sulfate, and concentrated in vacuo to a white solid. Trituration in petroleum ether yields 32.33 g. of white, fluffy N-[N-[(phenylmethoxy)carbonyl] -L-phenylalanyl]-L-alanine, methyl ester.

10% Palladium on carbon catalyst (1.5 g.) is added to a stirred suspension of the above methyl ester product (14.47 g., 37.64 mmole) and p-toluenesulfonic acid (7.16 g., 37.64 mmole) under argon. The reaction vessel is placed under 1 atmosphere of hydrogen and allowed to react overnight at room temperature. After 17 hours, the mixture is filtered to remove the catalyst and the solvent is distilled off in vacuo to give 17.51 g. of white solid N-(L-phenylalanyl)-L-alanine, methyl ester, p-toluenesulfonic acid salt; m.p. 158°–166°.

A solution of dicyclohexylcarbodiimide (90.79 g., 440 mmole) in ethyl acetate (200 ml.) is added to a chilled (0°), stirred suspension of N-hydroxy succinimide (46.04 g., 400 mmole) and acetylthioacetic acid (53.66 g., 400 mmole) in ethyl acetate (500 ml.) while maintaining the temperature below 5°. The mixture is allowed to react overnight while warming to room temperature. After 17 hours, the suspension is filtered and the precipitate is recrystallized from acetonitrile to give 28.42 g. of off-white solid acetylthioacetic acid, succinimide ester; m.p. 98.5°–100°.

This acetylthioacetic acid, succinimide ester (5 mmole) and N-(L-phenylalanyl)-L-alanine, methyl ester, p-toluenesulfonic acid salt (2.2 g., 5 mmole) are suspended in dimethylformamide (15 ml.) and chilled to 0° and placed under a nitrogen atmosphere. Diisopropylethylamine (0.96 ml.) is added and the mixture is stirred overnight, then poured into water (250 ml.) and extracted with ethyl acetate (4×75 ml.). The organic layers are combined and washed with saturated sodium bicarbonate (2×50 ml.), 10% potassium bisulfate (2×50 ml.), and brine (100 ml.), then dried over sodium sulfate, and concentrated in vacuo to an off-white solid. Recrystallization from acetonitrile gives 1.07 g. of white needle-like crystals of N-[N-(acetylthioacetyl)-L-phenylalanyl] -L-alanine, methyl ester.

1N Sodium hydroxide (5.4 ml.) is added to a stirred, chilled (−5°) suspension of the above methyl ester product (0.9 g., 2.46 mmole) in methanol (15 ml.) under argon while maintaining the temperature below 0°. The mixture is allowed to react for 3 hours in the cold, then poured into water (100 ml.), washed with ethyl acetate (2×40 ml.), acidified to a pH of about 1.5 with concentrated HCl, and then extracted with ethyl acetate (3×30 ml.). These organic portions are combined, washed with brine (80 ml.), dried over sodium sulfate, and concentrated in vacuo to a white solid (0.74 g.). Recrystallization from ethyl acetate gives white solid N-[N-(mercaptoacetyl)-L-phenylalanyl] -L-alanine; m.p. 172°–174.5°; $[\alpha]_D=-1.93°$ (c=1.97, methanol). TLC (silica gel; butanol:acetic acid:water, 4:1:1) $R_f=0.66$.

Anal. calc'd. for $C_{14}H_{18}N_2O_4S$: C, 54.18; H, 5.85; N, 9.03; S, 10.33 Found: C, 53.91; H, 5.63; N, 8.82; S, 10.07.

EXAMPLE 61

N-[N-(Mercaptoacetyl)-L-phenylalanyl]-L-phenylalanine

Following the procedure of Example 60, N-[(Phenylmethoxy)carbonyl]-L-phenylalanine and L-phenylalanine, methyl ester, hydrochloride are coupled in the presence of dicyclohexylcarbodiimide, hydroxybenzotriazole hydrate, and diisopropylethylamine. The resulting N-protected dipeptide is hydrogenated in the presence of palladium on carbon catalyst and p-toluenesulfonic acid to give N-(L-phenylalanyl)-L-phenylalanine, methyl ester, p-toluenesulfonic acid salt.

Treatment of this salt with acetylthioacetic acid, succinimide ester in the presence of diisopropylethylamine according to the procedure of Example 60 yields N-[N-(acetylthioacetyl)-L-phenylalanyl]-L-phenylalanine, methyl ester.

A cold (−10°), stirred suspension of this methyl ester product in methanol is treated with 1N sodium hydroxide under a nitrogen atmosphere and worked up as described in Example 60 to give N-[N-(mercaptoacetyl)-L-phenylalanyl] -L-phenylalanine as a white powder; m.p. 228–228.5; $[\alpha]_D=$ −5° (c=1, dimethylformamide). TLC (silica gel; benzene-:acetic acid, 4:1) $R_f$=0.31 (slight tailing).
Anal. calc'd. for $C_{20}H_{22}N_2O_4S·0.24 H_2O$: C, 61.47; H, 5.85; N, 7.06; S, 8.20, SH, 8.46 Found: C, 61.47; H, 5.85; N, 7.06; S, 8.02, SH, 8.30.

EXAMPLE 62

N-[N-(3-Mercapto-1-oxopropyl)-L-phenylalanyl]-L-phenylalanine (L)-Phenylalanyl-(L)-phenylalanine, methyl ester, p-toluenesulfonic acid salt (2.55 g., 5 mmole), dithiobis (2-carboxyethane) dicyclohexylamine salt (1.44 g., 2.5 mmole), and hydroxybenzotriazole hydrate (0.68 g., 5 mmole) are suspended in tetrahydrofuran (60 ml.) and chilled to 0°. A solution of dicyclohexylcarbodiimide (1.03 g., 5 mmole) in tetrahydrofuran (12 ml.) is added over 5 minutes, and the mixture is stirred for 30 hours, warming to room temperature. The dicyclohexyl urea is filtered off, and the filtrate is concentrated. The residue is mixed with ethyl acetate (150 ml., gentle warming) and filtered again. After washing with 10% potassium bisulfate (40 ml.), 50% brine (40 ml.), saturated sodium bicarbonate (40 ml.), and brine (40 ml.), the organic phase is partially concentrated and a precipitate is filtered off. The filtrate is dried over sodium sulfate and concentrated to an off-white crystalline solid dithiobis dimethyl ester product (1.59 g.).

A suspension of this dithiobis dimethyl ester product (1.35 g., 1.58 mmole) in methanol (20 ml.) is chilled to −10°. 1N Sodium hydroxide (3.4 ml.) is added dropwise over 10 minutes. The mixture is stirred overnight, warming to room temperature, and then is partially concentrated to remove the methanol. The solid yellow residue is suspended in water, basified to pH of about 14 with 1N sodium hydroxide, and washed with ethyl acetate (3×60 ml.). The aqueous layer is acidified to pH of about 3 with concentrated HCl (white precipitate forms) and extracted with ethyl acetate (3×40 ml.). Some white solid remains in suspension and is filtered and dried in vacuo. The organic extracts of the acidic aqueous mixture are combined, washed with brine (100 ml.), dried over sodium sulfate and concentrated to a light yellow solid. This material is pooled with the white solid to yield 1.1 g. of somewhat crude product. An analytical sample is prepared by successive recrystallizations of a portion of the crude product (600 mg.) from ethyl acetate to yield 280 mg. of white solid N',N"-[ dithiobis(1-oxo-3,1-propanediyl)]bis-N-(L-phenylalanyl)-L-phenylalanine; m.p. 198°–199°.

A solution of this dithiobis product (120 mg., 0.14 mmole) in methanol (12 ml.) is chilled in an ice bath. Concentrated HCl (1.2 ml.) is added followed by zinc dust (0.67 g.) in 4 portions over 30 minutes. The mixture is stirred in the cold for an additional 30 minutes, then is filtered, concentrated, and poured into 1N HCl (40 ml.). The resulting white precipitate is extracted with ethyl acetate (3×20 ml.), and the extract is dried over sodium sulfate and concentrated in vacuo to a cloudy white oil. This oil is applied to a column of silica gel (15 g., 230–400 mesh) and eluted with (5:1) toluene:acetic acid. Product containing fractions (number 5–7, 7 ml. each) are collected and concentrated in vacuo to give 57 mg. of white, crystalline solid N-[N-(3-mercapto-1-oxopropyl)-L-phenylalanyl]-L-phenylalanine; m.p. 169°–172.5°. TLC (silica gel; toluene:acetic acid, 5:1) $R_f$=0.31 (trace at 0.10 from air oxidation to the disulfide).
Anal calc'd. for $C_{21}H_{24}N_2O_4S·0.35 H_2O$: C, 62.00; H, 6.12; N, 6.89; S, 7.88 Found: C, 62.30; H, 6.04; N, 6.65; S, 7.58.

EXAMPLE 63

N-[N-(Mercaptoacetyl)-L-leucyl]glycine

A suspension of N-[(1,1-dimethylethoxy)carbonyl] -L-leucine (18.5 g., 80 mmole), glycine, phenylmethyl ester, p-toluenesulfonic acid salt (26.99 g., 80 mmole), hydroxybenzotriazole hydrate (10.81 g., 80 mmole) and diisopropylethylamine (14 ml., 80 mmole) in tetrahydrofuran (200 ml.) is chilled to −5° with vigorous stirring. A solution of dicyclohexylcarbodiimide (16.51 g., 80 mmole) in tetrahydrofuran (10 ml.) is added dropwise over 10 minutes. The reaction is allowed to proceed overnight, warming to room temperature. Afterward, the dicyclohexyl urea is filtered off and the filtrate is concentrated in vacuo. The residue, a yellow oil, is taken up in ethyl acetate (400 ml.), filtered again, and washed with 10% potassium bisulfate (150 ml.), water (150 ml.), saturated sodium bicarbonate (150 ml.), and 50% saturated sodium chloride, dried over sodium sulfate, and concentrated in vacuo to give 28.75 g. of N-[N-[(1,1-dimethylethoxy)carbonyl]-L-leucyl] glycine, phenylmethyl ester as a yellow glass.

Cold (−5°) trifluoroacetic acid (30 ml.) is added in one portion to a prechilled (−10°) solution of the above phenylmethyl ester product (20 g., 54.6 mmole) in methylene chloride (50 ml.). The solution is stirred for one hour in the cold and then concentrated in vacuo. Toluene (50 ml.) is added, and the residue is again concentrated in vacuo (twice). The resulting yellow oil is taken up in ether (100 ml.) and p-toluenesulfonic acid hydrate (10.38 g., 54.6 mmole) in ether (500 ml.) is added. The oily precipitate is dried in vacuo (2 days, 0.05 mm. of Hg) to give 29.57 g. of N-(L-leucyl) glycine, phenylmethyl ester, p-toluenesulfonic acid salt as a clear, viscous yellow oil.

A suspension of this phenylmethyl ester product (5.4 g., 10 mmole) and acetylthioacetic acid, succinimide ester (2.31 g., 10 mmole) in dimethylformamide (15 ml.) is chilled to 0° (drying tube). Diisopropylethylamine (1.74 ml., 10 mmole) is added in one portion and the reaction is allowed to proceed overnight, warming to room temperature. Afterward, the light pink suspension is poured into water (100 ml.) and the white precipitate is extracted with ethyl acetate (4×30 ml.). These organic layers are pooled, washed with 10% potassium bisulfate (50 ml.), water (50 ml.), saturated sodium bicarbonate (50 ml.), water (50 ml.), and brine (70 ml.), dried over sodium sulfate, and concentrated in vacuo to give 3.29 g. of light tan solid. Recrystallization of 3.25 g. of this material from (1:4) ethyl acetate:hexane gives 2.89 g. of white crystalline N-[N-(acetylthioacetyl)-L-leucyl] glycine, phenylmethyl ester; m.p. 117°–120°.

1N Sodium hydroxide (12.3 ml.) is added to a cold (−10°), stirred solution of the above acetylthioacetyl product (2.37 g., 6 mmole) in methanol (30 ml.) under an atmosphere of nitrogen. The mixture is stirred in the cold for 3.5 hours, then the methanol is removed in vacuo, and the residue is poured into water (40 ml.). The addition of sodium hydroxide fails to solubilize some suspended material but washing with ethyl acetate (2×30 ml.) produces a clear solution which is acidified to pH of about 1 with concentrated HCl and extracted with ethyl acetate (3×30 ml.). These organic layers are combined, washed with brine (50 ml.), dried over sodium sulfate, and concentrated in vacuo to give 0.88 g. of N-[N-(mercaptoacetyl)-L-leucyl]glycine as a clear, viscous, light yellow oil. $[\alpha]_D$=−27° (c=1, methanol). TLC (silica gel; chloroform: methanol: 37% aqueous acetic acid, 6:4:2) $R_f$= 0.57 (faint tailing).

Anal. calc'd. for $C_{10}H_{18}N_2O_4S$: C, 45.79; H, 6.92; N, 10.68; S, 12.22 Found: C, 45.74; H, 6.83; N, 10.50; S, 12.00.

EXAMPLE 64

(±)-1-[N-[2-(Mercaptomethyl)-1-oxo-3-phenylpropyl]-L-alanyl] -L-proline

A suspension of N-[(1,1-dimethylethoxy)-carbonyl] -L-alanine (189 g., 1 mole), L-proline, phenylmethyl ester, hydrochloride salt (286 g., 1.01 mole), hydroxybenzotriazole hydrate (154 g., 1.01 mole) and diisopropylethylamine (155.8 g., 1.18 mole) in dry tetrahydrofuran (3000 ml.) is cooled in an ice bath under nitrogen and treated with dicyclohexylcarbodiimide (208.2 g., 1.01 mole). The reaction mixture is stirred in the cold for 45 minutes, and then at room temperature for 22 hours. The reaction mixture is filtered to remove dicyclohexyl urea, and the filtrate is concentrated in vacuo. The residue is dissolved in ether (2500 ml.) and washed successively with saturated sodium bicarbonate, 5% potassium bisulfate, water, and brine, then dried over magnesium sulfate, and concentrated in vacuo to give 365 g. of 1-[N-[(1,1-dimethylethoxy)carbonyl] -L-alanyl]-L-proline, phenylmethyl ester as a thick oil.

A solution of this oil (365 g., 960 mmole) in trifluoroacetic acid (1500 g., 13.2 mole) is cooled in an ice bath for 3 hours and then stirred at ambient temperature for one hour. The solution is concentrated in vacuo, and the residue is azeotroped with toluene to give 380g. of the trifluoroacetate salt as an oil. This oil is dissolved in ether (600 ml.) and added to a solution of p-toluenesulfonic acid monohydrate (186 g., 980 mmole) in acetone (200 ml.) and ether (4300 ml.). The mixture is stirred for 20 hours and then filtered to give 366 g. of 1-L-alanyl-L-proline, phenylmethyl ester, 4-methylbenzenesulfonate salt (1:1); m.p. 154°–155°. TLC(silica gel; methanol) $R_f$=0.23.

A solution of 1-L-alanyl-L-proline, phenylmethyl ester, 4-methylbenzenesulfonate salt (1:1) (1.62 g., 3.6 mmole) in methylene chloride (5 ml.) is treated with diisopropylethylamine (465 mg., 3.6 mmole). The resulting solution is cooled to −5° under nitrogen and treated dropwise with a solution of 2-acetylthiomethyl-3-phenylpropanoyl chloride (3.6 mmole, prepared by reacting 2-acetylthiomethyl-3-phenylpropionic acid with oxalyl chloride) in dry methylene chloride (5 ml.) concurrently with diisopropylethylamine (465 mg., 3.6 mmole). After the addition is complete, the solution is stirred in the cold for 2 hours and then allowed to warm to ambient temperature overnight. The reaction mixture is then concentrated in vacuo. The residue is dissolved in ethyl acetate (25 ml.) and this solution is washed with 5 ml. portions of 10% aqueous potassium bisulfate, water, 5% aqueous sodium bicarbonate, water, and brine, then dried over magnesium sulfate, and concentrated in vacuo to give 1.7 g. of crude product as an oil. Flash chromatography on silica gel (170 g.) eluting with (3:1) petroleum ether:acetone gives 1.4. g. of (±)-1-[N-[2-(acetylthiomethyl)-1-oxo-3-phenylpropyl]-L-alanyl] -L-proline, phenylmethyl ester as an oil. TLC (silica gel; petroleum ether:acetone, 3:1) $R_f$=0.24.

A solution of this phenylmethyl ester product (1.4 g., 2.82 mmole) in methanol (20 ml.) is cooled in an ice bath under nitrogen and treated dropwise with 1N sodium hydroxide solution (8.46 ml., 8.46 mmole). After the addition is complete, the reaction mixture is stirred in the cold for 15 minutes and then allowed to warm to ambient temperature overnight. The reaction mixture is then concentrated in vacuo to remove the methanol. The remaining aqueous layer is diluted with water (25 ml.) and washed with chloroform (2×10 ml.). The aqueous layer is acidified to pH 1 with concentrated HCl and extracted with ethyl acetate (3×25 ml.). The combined organic extract is washed with 10 ml. of water and brine, dried over magnesium sulfate, and concentrated in vacuo to yield 1.1 g. of crude product. Flash chromatography on silica gel (110 g.) eluting with (40:1:1) methylene chloride:methanol:acetic acid gives 900 mg. of partially purified product. Flash chromatography on silica gel (90 g.) eluting with (7:1) toluene:acetic acid yields 600 mg. of (±)-1-[N-[2-(mercaptomethyl)-1-oxo- 3-phenylpropyl]-L-alanyl]-L-proline as a white solid; m.p. 151°–175°; $[\alpha]_D$=−112° (c=0.5, methanol), TLC (silica gel; benzene:acetic acid, 4:1) $R_f$=0.52.

Anal. calc'd. for $C_{18}H_{24}N_2O_4S$: C, 59.32; H, 6.64; N, 7.69; S, 8.80; SH, 9.07 Found: C, 59.20; H, 6.69; N, 7.47; S, 8.55; SH, 8.86.

EXAMPLE 65

(R)-1-[N-(2-Mercapto-1-oxo-3-phenylproppyl)-L-alanyl]-L-proline

Dicyclohexylcarbodiimide (3.17 g., 15.4 mmole) is added dropwise over 10 minutes to an ice-cooled solution of (R)-2-acetylthio-3-phenylpropionic acid (3.45 g., 15.4 mmole, prepared as described in Example 37) and hydroxybenzotriazole hydrate (2.59 g., 16.94 mmole) in tetrahydrofuran (50 ml.). The mixture is stirred for 75 minutes at room temperature, filtered to remove dicyclohexyl urea, and dried in vacuo to remove the tetrahydrofuran. The oily residue is taken up in dimethylformamide (50 ml.) and L-alanyl-L-proline, 1,1-dimethylethyl ester (3.1 g., 12.83 mmole) and triethylamine (1.8 ml., 12.83 mmole) are added. The reaction mixture is allowed to stand for 18 hours at room temperature. The dimethylformamide is removed in vacuo and the oily residue is redissolved in ethyl acetate and washed with water, 10% citric acid, and saturated sodium bicarbonate. Ethyl acetate is removed in vacuo and the oily residue is chromatographed over silica gel (400 g.) eluting with (6:1) toluene:acetone. The product is further purified by dissolving in chloroform and washing with water. Removal of the chloroform in vacuo gives 3.2 g. of (R)-1-[N-(2-acetylthio- 1-oxo-3-phenylpropyl)-L-alanyl]-L-proline, 1,1-dimethylethyl ester; $[\alpha]_D$=−20° (c=1.05, chloroform). TLC (silica gel; toluene:acetone, 4:1) $R_f$=0.48.

This 1,1-dimethylethyl ester product (4.4 g., 9.82 mmole) is dissolved in trifluoroacetic acid containing 5% anisole (22 ml.) and is allowed to stand at room temperature for 1.5 hours. The solvent is removed in vacuo and the oily residue is dissolved in ether, and the product is precipitated as a gum with hexane. This gum is then triturated with ether to give 2.6 g. of solid (R)-1-[N-(2-acetylthio-1-oxo- 3-phenylpropyl)-L-alanyl]-L-proline; m.p. (124°) 135°–138°; $[\alpha]_D$=− 23° (c=1.4, chloroform). An additional (0.57 g.) of product crystallizes from the ether/hexane washes.

1N Aqueous sodium hydroxide (20.52 ml.) is added to a solution of (R)-1-[N-(2-acetylthio-1-oxo-3-phenylpropyl)-L-alanyl] -L-proline (2.68 g., 6.84 mmole) in methanol (3 ml.) and the reaction mixture is allowed to stand under argon at room temperature for 15 minutes. The methanol is removed in vacuo, and the aqueous solution is acidified with HCl (about 3N, 7.5 ml.). The acidified solution is saturated with sodium chloride and extracted exhaustively with ethyl acetate. The ethyl acetate is removed in vacuo, and the residue is evaporated from methanol/water and chloroform to give 2.4 g. of (R)-1-[N-(2-mercapto- 1-oxo-3-phenylpropyl)-L-alanyl]-L-proline as a foamy solid; $[\alpha]_D = -78.4°$ (c=1.1, chloroform). TLC(silica gel; ethyl acetate:pyridine:acetic acid: water, 45:20:6:11) $R_f$=0.45.

Anal. calc'd. for $C_{17}H_{22}N_2O_4S \cdot 2H_2O$: C, 52.83; H, 6.78; N, 7.25; S, 8.30 Found: C, 52.54; H, 6.26; N, 7.01; S, 8.16.

EXAMPLE 66

(S)-1-[N-(2-Mercapto-1-oxo-3-phenylpropyl)-L-alanyl]-L-proline

Following the procedure of Example 65, (S)-2-acetylthio-3-phenylpropionic acid (prepared as described in Example 38) is reacted first with dicyclohexylcarbodiimide and hydroxybenzotriazole hydrate and then with L-alanyl-L-proline, 1,1-dimethylethyl ester and triethylamine to give (S)-1-[N-(2-acetylthio- 1-oxo-3-phenylpropyl)-L-alanyl]-L-proline, 1,1-dimethylethyl ester.

Treatment with trifluoroacetic acid and anisole to remove the proline ester group and treatment with sodium hydroxide to give the mercaptan group according to the procedure of Example 65 yields solid (S)-1-[ N-(2-mercapto-1-oxo-3-phenylpropyl)-L-alanyl]-L-proline; $[\alpha]_D = -82.7°$ (c=1.5, chloroform). TLC(silica gel; ethyl acetate:pyridine:acetic acid:water, 45:20:6:11) $R_f$=0.58.

Anal. calc'd. for $C_{17}H_{22}N_2O_4S \cdot 1H_2O$: C, 55.42; H, 6.56; N, 7.60; S, 8.70 Found: C, 55.25; H, 6.18; N, 7.36; S, 8.43.

EXAMPLE 67

(trans)-N-[N-[[2-(Mercaptomethyl)cyclohexyl]carbonyl]-L-phenylalanyl] -L-leucine This compound can be prepared as described in detail in Example 65 of U.S. Pat. No. 4,560,506.

EXAMPLE 68

(trans)-N-[N-[(2-Mercaptocyclohexyl)carbonyl]-L-phenylalanyl] -L-leucine (isomer A)

This compound can be prepared as described in detail in Example 6 of U.S. Pat. No. 4,560,506.

EXAMPLE 69

3-[[1-(Mercaptomethyl)-2-phenylethyl]amino]-3-oxo-propanoic acid

Diisopropylethylamine (4.03 ml., 23.2 mmole) is added dropwise to a stirred suspension of 2-amino- 3-phenyl-1-propanol, hydrochloride (4.35 g., 23.2 mmole) in methylene chloride (100 ml.) at 0°. After all the material is in solution, a solution of malonic acid monoethyl ester (3.06 g., 23.2 mmole) in methylene chloride (25 ml.) is added followed by the dropwise addition of a suspension of dicyclohexylcarbodiimide (4.78 g., 23.2 mmole) in methylene chloride (75 ml.) over 5 minutes. The reaction mixture is then removed from the ice-bath and stirred at room temperature for 16 hours. The dicyclohexyl urea is filtered off and washed with ethyl acetate. The filtrate is evaporated and the residue is triturated with ethyl acetate (about 225 ml.) and again filtered. The filtrate is washed sequentially with 10% potassium bisulfate, water, half-saturated sodium bicarbonate, water, and brine (3×30 ml. each), dried over sodium sulfate, and concentrated in vacuo to give 5.6 g. of light blue colored solid. This material is adsorbed onto a small amount of silica (Merck, 230–400 mesh), dried, and applied to a column of the same silica (350 g.). Elution with 4 l. of ethyl acetate/hexane (3:2) followed by 2 l. of ethyl acetate yields 4.15 g. of 3-[[1-(hydroxymethyl)-2-phenylethyl]amino]- 3-oxopropanoic acid, ethyl ester; m.p. 58°–60°.

Diisopropyl azodicarboxylate (5 ml., 25.4 mmole) is added to a thoroughly stirred solution of triphenylphosphine (6.66 g., 25.4 mmole) in tetrahydrofuran (65 ml.) at 0°. The mixture is stirred at 0° for 30 minutes after which a light yellow precipitate occurs. A solution of thiolacetic acid (1.82 ml., 25.4 mmole) and 3-[[1-(hydroxymethyl)-2-phenylethyl] -amino] -3-oxopropanoic acid, ethyl ester (3.36 g., 12.7 mmole) in tetrahydrofuran (50 ml.) is added over 10 minutes. The mixture is stirred for 2 hours at 0° and 1 hour at room temperature (during which time the mixture turns green and then light yellow), and is then concentrated in vacuo. The resulting residue is taken up in ethyl acetate (125 ml.), washed with saturated sodium bicarbonate (3×30 ml.), dried over sodium sulfate, and concentrated to yield a yellow oil with a white precipitate. The residue is taken up in ethyl acetate:hexane (2:3), filtered to remove the precipitate, and concentrated. The remaining yellow oil (9.19 g.) is applied to a column of silica (Merck, 230–400 mesh, 450 g.) and eluted with hexane/ethyl acetate (3:2) to yield 3.48 g. of a yellow oil. A portion of this material (3.4 g.) is applied to a second column of silica (230 g.) and eluted with hexane/ethyl acetate (4:3) to yield 2.71 g. of pale yellow solid 3-[[1-[(acetylthio)methyl] -2-phenylethyl]amino]-3-oxopropanoic acid, ethyl ester; m.p. 59°–63°.

This acetylthiomethyl product (2.68 g., 8.29 mmole) is dissolved in cold (0°) methanol (35 ml.) and stirred under nitrogen. 1N Sodium hydroxide (35 ml.) is added dropwise to this solution over 10 minutes. The mixture is stirred at 0° for 10 minutes, then warmed to room temperature and allowed to stir for 3 hours. The mixture is then concentrated to about one half volume in vacuo. The residue is diluted with water (40 ml.) and then washed with chloroform (2×20 ml.). The aqueous layer is acidified to pH 1.5 with concentrated HCl. The resulting white suspension is extracted with ethyl acetate (3×15 ml.). The organic layers are combined, washed with water and brine (20 ml. each), dried over sodium sulfate, and concentrated to a white solid (2.05 g.). A sample of this material (1.96 g.) is dissolved by heating in a small volume of toluene/acetic acid (4:1), applied to a column of silica (Merck, 230–400 mesh, 140 g.), and eluted with toluene/acetic acid (4:1) to give 1.83 g. of crude product. This material is dissolved in hot ethyl acetate/hexane and chilled on ice. After considerable scratching, crystals form which are filtered to give 0.719 g. of 3-[[1-(mercaptomethyl)- 2-phenylethyl]amino]-3-oxopropanoic acid; m.p. 109°–112°. TLC(silica gel; n-butanol:water:acetic acid, 4:1:1) $R_f$=0.69.

Anal. calc'd. for $C_{12}H_{15}NO_3S$: C, 56.90; H, 5.97; N, 5.53; S, 12.66, SH, 13.06 Found C, 56.81; H, 6.02; N, 5.35; S, 12.37; SH, 12.65.

EXAMPLE 70

6-[[1-(Mercaptomethyl)-2-phenylethyl]amino]-6-oxohexanoic acid

Following the procedure of Example 69 but employing adipic acid monoethyl ester one obtains 6-[[1-(hydroxymethyl)-2-phenylethyl]amino]-6-oxohexanoic acid, ethyl ester.

Reaction of this ethyl ester product with thiolacetic acid according to the procedure of Example 69 yields 6-[[1-[(acetylthio)methyl]-2-phenylethyl] amino]-6-oxohexanoic acid, ethyl ester. Treatment with sodium hydroxide in chilled methanol yields white solid 6-[[1-(mercaptomethyl)-2-phenylethyl] amino]-6-oxohexanoic acid; m.p. 82°–85°. TLC (silica. gel; benzene:acetic acid, 4:1) $R_f$=0.41.

Anal. calc'd. for $C_{15}H_{21}NO_3S$: C, 60.99; H, 7.17; N, 4.74; S, 10.85; SH, 11.20 Found: C, 60.92; H, 7.15; N, 4.76; S, 10.75; SH, 11.00.

A more detailed description of the preparation of this compound appears as Example 1 in European Patent Application 161,769.

EXAMPLE 71

8-[[1-(MercaDtomethyl)-2-phenylethyl]amino]-8-oxooctanoic acid

Following the procedure of Example 69 but employing suberic acid, monomethyl ester one obtains 8-[[1-(hydroxymethyl)-2-phenylethyl)amino]-8-oxooctanoic acid, methyl ester.

Reaction of this methyl ester product with thiolacetic acid according to the procedure of Example 69 yields 8-[[1-[(acetylthio)methyl]-2-phenylethyl] amino]-8-oxooctanoic acid, methyl ester. Treatment with sodium hydroxide in chilled methanol yields white solid 8-[[1-(mercaptomethyl)-2-phenylethyl] amino]-8-oxooctanoic acid; m.p. 90°–92° (sinters above 87°). TLC(silica gel; toluene:acetic acid, 4:1) Rf =0.33.

Anal. calc'd. for $C_{17}H_{25}NO_3S$: C, 63.13; H, 7.79; N, 4.33; S, 9.91; SH, 10.22 Found: C, 63.13; H, 7.91; N, 4.26; S, 9.90; SH, 10.17.

A more detailed description of the preparation of this compound appears in Examples 2 and 3 of European Patent Application 161,769.

EXAMPLE 72

N-(α-L-Rhamnopyranosyloxyhydroxyphosphinyl)-L-leucyl-L-tryptophan

The preparation of phosphoramidon is described by Umezawa et al. in Tetrahedron Letters No.1, pages 97–100 (1972).

EXAMPLE 73

N-[N,.[Hydroxy(methyl)phosphinyl]-L-phenylalanyl]-L-leucine, dilithium salt

This compound can be prepared as described in detail in Example 1 of U.S. Pat. No. 4,432,972.

EXAMPLE 74

N-[2,[(Hydroxymethylphosphinyl)-1-oxo-3-phenylpropyl] -L-leucine, dilithium salt A mixture of methylphosphinic acid, ethyl ester (661 mg., 6.12 mmole), 2-benzylacrylic acid, methyl ester (900 mg., 5.1 mmole) and bis(trimethylsilyl)acetamide (1.03 g., 5.1 mmole) is refluxed under nitrogen for 7 hours and then stirred at ambient temperature for 16 hours. The reaction mixture is then diluted with chloroform (70 ml.), washed with water (2×10 ml.) and brine, and dried over magnesium sulfate. Removal of the solvents in vacuo gives 2.4 g. of crude product which is chromatographed on alumina (activity III, 100 g.) eluting with ether then ether:methanol (40:1). The product containing fractions are pooled to give 1.14 g. of 3-phenyl- 2-[(ethoxymethylphosphinyl)methyl]propanoic acid, methyl ester.

A solution of this methyl ester product (400 mg., 1.41 mmole) in methanol (1 ml.) is treated with 1N aqueous sodium hydroxide (9 ml.). The mixture is heated in a 50° oil bath for 3 hours and then quenched with acetic acid and concentrated in vacuo. The concentrated reaction mixture is eluted on a 100 ml. AG 50W-X2 ($H^+$) column run in 15% aqueous methanol. Removal of the solvents in vacuo gives 3-phenyl-2-[(hydroxymethylphosphinyl)methyl] propanoic acid.

Carbonyldiimidazole (251 mg., 1.55 mmole) is added to a solution of 3-phenyl-2-[(hydroxymethylphosphinyl)methyl] propanoic acid (342 mg., 1.41 mmole) in dry tetrahydrofuran (8 ml.) at room temperature under argon. After 90 minutes the reaction is cooled in an ice-water bath and treated with L-leucine, phenylmethyl ester, p-toluenesulfonic acid salt (610 mg., 1.55 mmole) followed by the addition of N-methylmorpholine (285 mg., 2.82 mmole). After one hour, the ice bath is removed and the reaction is stirred at room temperature for 16 hours. The reaction mixture is then diluted with ethyl acetate (60 ml.), rinsed twice with 10 ml. portions of 1N HCl, two 10 ml. portions of water, and brine, and dried over magnesium sulfate. Concentration in vacuo gives N-[2-[(hydroxymethylphosphinyl)methyl]-1-oxo- 3-phenylpropyl]-L-leucine, phenylmethyl ester as an oil.

This phenylmethyl ester product (628 mg., 1.41 mmole) is deprotected in two batches by atmospheric hydrogen in methanol in the presence of palladium on carbon catalyst. The reaction mixture is filtered over Celite and the filtrate is treated with triethylamine and then concentrated in vacuo. The residue is then eluted through a column of AG 50W-X8($Li^+$) in water to give the solid dilithium salt after lyophilization. This crude dilithium salt is purified by reverse chromatography on a HP-20 column (25×400 mm.) gradient eluted from 400 ml. of water to 400 ml. of acetonitrile. The product containing fractions are pooled and further purified by elution through an LH-20 column (15× 200 mm.) run in water. The product containing fractions are combined and lyophilized to give 140 mg. of solid N-[2-[(hydroxymethylphosphinyl)methyl] -1-oxo-3-phenylpropyl]-L-leucine, dilithium salt; m.p. 247°–252° (dec.); $[α]_D$= −36.4° (c=0.5, water). TLC (silica gel; chloroform:methanol:acetic acid, 11:1:1) $R_f$=0.15, 0.12.

Anal. calc'd. for $C_{17}H_{24}NO_5P·2Li·0.9H_2O$: C, 53.25; H, 6.78; N, 3.65; P, 8.08 Found: C, 53.43; H, 7.06; N, 3.50; P, 7.80.

EXAMPLE 75

3-[[1-Oxo-2-(phenylmethyl)-3-phosphonopropyl] amino] propanoic acid

Bis(trimethylsilyl)acetamide (5 g., 24 mmole, 6 ml.) is added at room temperature to a solution of 2-benzylacrylic acid (2 g., 12 mmole) and diethyl phosphite (3.3 g., 24 mmole) in methylene chloride(30 ml.). The mixture is stirred at ambient temperature for 30 minutes, concentrated in vacuo at room temperature, and the residue is heated at a bath temperature of 100°–110° for 16 hours. The colorless oil reaction mixture is dissolved in ethyl acetate and extracted with 5% sodium bicarbonate (pH 9–10). The aqueous alkaline solution is washed with ether and acidified to pH of 1–2 with concentrated HCl. The colorless oil-that separated is extracted into ethyl acetate, washed with brine, dried over magnesium sulfate, and concentrated in vacuo to give 3.6 g. of 3-phenyl-2-[(diethoxyphosphinyl)methyl]propanoic acid as a colorless oil.

A solution of 3-phenyl-2-[(diethoxyphosphinyl)methyl]propanoic acid (2.2 g., 7.33 mmole) in tetrahydrofuran (70 ml.) is cooled in an ice-water bath and 1,1'-carbonyldiimidazole (1.3 g., 8.0 mmole) is added. After stirring for one hour, β-alanine, phenylmethyl ester, hydrochloride salt (1.73 g., 8 mmole) is added followed by triethylamine (1.6 g., 16 mmole). The bath is removed and the mixture is stirred at ambient temperature for 16 hours. The solids are removed by filtration. The filtrate is concentrated in vacuo. The residue is dissolved in ethyl acetate, washed with water, 5% potassium bisulfate to a pH of 1–2, water, saturated sodium bicarbonate, and brine, dried over magnesium sulfate, and concentrated in vacuo. The oil residue (3.7 g.) becomes semisolid on standing at room temperature. The residue is chromatographed on silica gel (Whatman LPS-1, 160 g.) eluting with ethyl acetate to give 2.5 g. of 3-[[2-[(diethoxyphosphinyl)methyl]-1-oxo- 3-phenylpropyl] amino]propanoic acid, phenylmethyl ester as a colorless oil.

Bromotrimethylsilane (2.0 g., 13 mmole) is added at room temperature to a solution of the above phenylmethyl ester product (2.2 g., 47 mmole) in methylene chloride (45 ml.). After remaining overnight at room temperature, the mixture is concentrated in vacuo. The residue is taken up in water (25 ml.) and saturated sodium bicarbonate (25 ml.) is added. The resulting alkaline solution is diluted with water to 100 ml., washed with ethyl acetate and ether, and acidified to pH 1–2 by the addition of concentrated HCl. The solid that separates is collected by suction filtration, triturated with refluxing acetonitrile (50 ml.), cooled, and filtered to give 1.5 g. of product after drying in vacuo at 80° for 4 hours. A sample is recrystallized from acetonitrile to give 3-[[1-oxo-2-(phenylmethyl)-3-phosphonopropyl]-amino] propanoic acid, phenylmethyl ester; m.p. 122°–123°.

A solution of this phenylmethyl ester product (1.4 g., 34 mmole) in glacial acetic acid (50 ml.) plus palladium hydroxide on carbon catalyst is placed on a Parr reduction apparatus at 50 psi. After 5 hours, the mixture is filtered through Celite and concentrated in vacuo. Toluene is added to the residue and the mixture is again concentrated in vacuo. This procedure is repeated several times and the glassy solid residue (1.2 g.) remains in vacuo overnight. It is triturated with refluxing ethyl acetate. It is then recrystallized from acetonitrile:water (19:1, 10 ml.) followed by recrystallization from acetone (100 ml.) to give 400 mg. of solid 3-[[1-oxo-2-(phenylmethyl)-3-phosphonopropyl]-amino] propanoic acid; m.p. 138°–140°. TLC (silica gel; n-butanol:pyridine:acetic acid:water, 4:1:1:1) $R_f$=0.50.

Anal. calc'd. for $C_{13}H_{18}NO_6P$: C, 49.59; H, 5.76; N, 4.44; P, 9.82 Found: C, 49.42; H, 5.95; N, 4.50; P, 9.90.

EXAMPLE 76

N-[(S)-2-[(Hydroxymethylphosphinyl)oxy]-1-oxo-3-phenylpropyl] -L-leucine

Diisopropylethylamine (6.97 ml., 40 mmole) is added to a suspension of L-leucine, phenylmethyl ester, p-toluenesulfonic acid salt (15.74 g., 40 mmole) at 0°–5° under argon followed by (S)-2-hydroxy- 3-phenylpropanoic acid (6.65 g., 40 mmole) and 1-hydroxybenzotriazole hydrate (5.4 g., 40 mmole). A solution of dicyclohexylcarbodiimide (8.25 g., 40 mmole) in tetrahydrofuran (25 ml.) is added and the reaction mixture is stirred for 3 hours at 0° then at room temperature overnight. The dicyclohexyl urea is filtered off and washed with ethyl acetate. The filtrate is evaporated and the residue is taken up in ethyl acetate (300 ml.), washed with 10% potassium bisulfate, water 5% sodium bicarbonate, water, and brine, dried over sodium sulfate, and evaporated to give 15.26 g. of a pale yellow crystalline solid. Two recrystallizations from ethyl acetate yields 10.12 g. of N-[(S)-2-hydroxy- 3-phenyl-1-oxopropyl]-L-leucine, phenylmethyl ester as a white solid; m.p. 110.5°–112.5°.

Dibenzyl phosphite (5.24 g., 20 mmole) is added in one portion to a suspension of sodium hydride 60% mineral oil dispersion (832 mg., 20.8 mmole) in dimethylformamide (30 ml.) under argon. The resulting mixture is stirred at room temperature for one hour then at 40° for 30 minutes. The clear amber solution is allowed to cool to room temperature and then a solution of iodomethane (3.36 g., 23.7 mmole) in dimethylformamide (3 ml.) is added over 5 minutes. After an hour of stirring at room temperature, the reaction mixture is poured into 5% potassium bisulfate (200 ml.) and extracted with ethyl acetate (1×100 ml., 4×50 ml.). The combined ethyl acetate extract is washed with 5% sodium bicarbonate (2×50 ml.) and brine, then dried and evaporated to give 4.39 g. of a dark yellow liquid. Flash chromatography on silica gel (Whatman LPS - 1, 325 g.) eluting with ethyl acetate::hexane (3:2) gives 2.27 g. of methylphosphonic acid, dibenzyl ester as a slightly yellow liquid.

Phosphorus pentachloride (1.09 g., 5.25 mmole) is added to solution of methylphosphonic acid, dibenzyl ester (1.38 g., 5 mmole) in dry benzene (7.5 ml.) under nitrogen. The mixture is stirred for 30 minutes at room temperature then at 60° (bath temperature) for 45 minutes. The solution is evaporated. The residue is taken up in benzene and the resulting solution is evaporated. This sequence is repeated to remove traces of phosphoryl chloride. The crude phosphonochloridate is taken up in dry methylene chloride (5 ml.), cooled to 0°–5° under argon and treated with a solution of N-[(S)-2-hydroxy-3-phenyl- 1-oxopropyl]-L-leucine, phenylmethyl ester (1.85 g., 5.0 mmole) and 4-pyrrolidinopyridine (75 mg., 0.5 mmole) in dry methylene chloride (5 ml.). A solution of diisopropylethylamine (0.92 ml., 5.2 mmole) in dry methylene chloride (5 ml.) is added dropwise over 10 minutes. The reaction mixture is stirred for 30 minutes at 0°–5°, then at room temperature overnight. The solvent is evaporated and the residue is taken up in ethyl acetate (150 ml.). This solution is washed with 10% potassium bisulfate, water, 5% sodium bicarbonate, water, and brine, then dried over sodium sulfate, and evaporated to 3.07 g. of a yellow residue. Flash chromatography on silica gel (Whatman LPS - 1, 300 g.) eluting with ethyl acetate:hexane (3:2) gives N-[(S)-2-[[(phenylmethoxy)methylphosphinyl]oxy]-1-oxo- 3-phenylpropyl]-L-leucine, phenylmethyl ester as a white solid.

A solution of this phenylmethyl ester product (950 mg., 1.77 mmole) in ethyl acetate (25 ml.) and acetic acid (2.5 ml.) is stirred with 10% palladium on carbon catalyst (200 mg.) under a flow of hydrogen for 4 hours at room temperature. The catalyst is filtered off and the solvent is evaporated. The residue is dissolved in toluene and the solution is evaporated. The colorless residue is then recrystallized twice from ethyl acetate-hexane to yield 476 mg. of white crystalline solid N-[(S)-2[ (hydroxymethylphosphinyl)-oxy]-1-oxo-3-phenylpropyl]-L-leucine; m.p. 124°–125°; $[\alpha]_D$=–32.3° (c=1.0, methanol). TLC(silica gel; chloroform:methanol:acetic acid) $R_f$=0.38.

Anal. calc'd. for $C_{16}H_{24}NO_6P$: C, 53.78; H, 6.77; N, 3.92; P, 8.67 Found: C, 53.79; H, 6.66; N, 3.86; P, 8.50.

EXAMPLE 77

N-[(S)-2-[[Hydroxy(2-phenylethyl)phosphinyl]oxy]- 1-oxo- 3-phenylpropyl]-L-leucine, dilithium salt Dibenzyl phosphite (11.93 ml., 54 mmole) is added dropwise to a stirred suspension of prewashed sodium hydride (1.45 g., 59.4 mmole) in dry dimethylformamide (40 ml.) under argon at room temperature. After 40 minutes at room temperature, the brown homogeneous mixture is treated with phenethyl bromide (7.38 ml., 54 mmole) and then stirred for 20 minutes. The mixture is then partitioned between 5% potassium bisulfate and ethyl acetate. The organic layer is washed with brine, dried over anhydrous sodium sulfate, and evaporated to a viscous yellow oil (20.6 g.). The crude oil is purified by flash chromatography on silica gel (Whatman LPS-1) eluting with hexane:ethyl acetate (7:3). Product containing fractions are pooled, concentrated, and crystallized from pentane to give 3.92 g. of white crystalline solid (2-phenylethyl)phosphonic acid, dibenzyl ester; m.p. 53°–55°.

This (2-phenylethyl)phosphonic acid, dibenzyl ester is reacted with N-[(S)-2-hydroxy-3-phenyl-1-oxopropyl] -L-leucine, phenylmethyl ester according to the procedure described in Example 76 to give N-[(S)-2[ [(phenylmethoxy)(2-phenylethyl)phosphinyl]oxy]-1-oxo- 3-phenylpropyl]-L-leucine, phenylmethyl ester as a colorless oil.

A solution of this phenylmethyl ester product (1.43 g., 2.3 mmole) in ethyl acetate (35 ml.) and acetic acid (3.5 ml.) is treated with 10% palladium on carbon catalyst (300 mg.) and subjected to a steady flow of hydrogen at one atmosphere of pressure. After 5.5 hours, the reaction mixture is filtered through Celite and concentrated in vacuo to give 1 g. of crude didcid product. A solution of this diacid (855 mg., 1.9 mmole) in a water/acetone/methanol mixture is treated with 2N aqueous lithium hydroxide solution (1.9 ml., 3.8 mole), filtered, and concentrated in vacuo. The residue is chromatographed on a 150 ml. HP-20 column eluting with a gradient from 300 ml. of water to 300 ml. of acetonitrile. The product containing fractions are combined and lyophilized to give 510 mg. of N-[(S)-2-[[hydroxy-( 2-phenylethyl)phosphinyl]oxy]-1-oxo-3-phenylpropyl]-L-leucine, dilithium salt as a white solid; m.p. 212°–225°; $[\alpha]_D = -16.2°$ (c=1, methanol). TLC(silica gel; chloroform:methanol:acetic acid, 15:1:1) $R_f=0.13$.

Anal. calc'd. for $C_{23}H_{28}NO_6PLi_2 \cdot 1.75\ H_2O$: C, 56.28; H, 6.47; N, 2.85; P, 6.31 Found: C, 56.31; H, 6.19; N, 2.90; P, 6.40.

EXAMPLE 78

3-[[N-[(S)-1-Carboxy-2-phenylethyl]-L-phenylalanyl]-amino] propanoic acid a) β-Alanine, phenylmethoxy ester, monohydrochloride

A solution of di-tert-butyl dicarbonate (60 g., 275 mmole) in t-butanol (50 ml.) is added dropwise with vigorous stirring over a period of 75 minutes to a suspension of β-alanine (22.27 g., 250 mmole) and sodium hydroxide (10 g., 250 mmole) in water (25 ml.) and t-butanol (50 ml.). After the addition is completed, the mixture is diluted with 25 ml. of 2:1 t-butanol:water and allowed to stir overnight. The reaction mixture is diluted with water (125 ml.) and extracted with pentane (3×150 ml.). The aqueous layer is cooled in an ice-bath and then acidified to pH 2–3 with a solution of potassium bisulfate (35 g. in 150 ml. of water). The product is extracted into ethyl acetate (4×200 ml.). The combined organic extract is washed with water and brine, dried over sodium sulfate, and evaporated to give 43.74 g. of white solid N-[(1,1-dimethylethoxy)carbonyl]-β-alanine, m.p. 73.5°–76°.

Sodium bicarbonate (25.2 g., 300 mmole) is added to a stirred solution of N-[(1,1-dimethylethoxy)carbonyl] -β-alanine (28.38 g., 150 mmole) in dimethylformamide (125 ml.) under argon followed by the dropwise addition of a solution of benzyl bromide (17.8 ml., 150 mmole) in dimethylformamide (25 ml.) over an hour. The reaction mixture is allowed to stir at room temperature (protected from the light). After 50 hours, an additional amount of benzyl bromide (1.78 ml., 15 mmole) is added. After an additional 40 hours, the dimethylformamide is evaporated. The residue is diluted with water (250 ml.) and extracted with ethyl acetate (3×150 ml.). The combined ethyl acetate extract is washed with 5% sodium bicarbonate, water, and brine, then dried over sodium sulfate and evaporated to yield 28.56 g. of a nearly colorless oil. This material (14 g.) is purified in two portions by flash chromatography on silica gel (Merck, 320 g.) eluting with hexane:ethyl acetate (5:1) to give 12.34 g. of N-[(1,1-dimethylethoxy)carbonyl] -β-alanine, phenylmethyl ester as an oil.

A 1.5 N solution of HCl in acetic acid (240 ml.) is added in rapid drops over 30 minutes to a stirred solution of N-[(1,1-dimethylethoxy)carbonyl] -β-alanine, phenylmethyl ester (12.19 g., 43.6 mmole) in acetic acid (44 ml.) at 15°. After the addition is completed, the solution is stirred for one hour at 15° and then the solvent is evaporated. The residue is crystallized by the addition of ether, triturated and collected to give 9.12 g. of white solid β-alanine, phenylmethyl ester, monohydrochloride; m.p. 87°–89.5°.

b) (S),N-[1-[(1,1-Dimethylethoxy)carbonyl]-2-phenylethyl] -L-phenylalanine

A solution of sodium nitrite (25.9 g., 360 mmole) in water (100 ml.) is added dropwise over 2 hours to a stirred solution of D-phenylalanine (16.52 g., 100 mmole) in 10% sulfuric acid (250 ml.) at 45°–50°. After the addition is completed, the reaction mixture is stirred for 4.5 hours at 50° and then at room temperature overnight. The reaction mixture is extracted with ethyl acetate (3×100 ml.), then the combined organic extract is washed with water and brine, dried over sodium sulfate, and evaporated to yield 14.79 g. of a pale yellow solid. Recrystallization from benzene gives 11.62 g. of (R)-2-hydroxy-3-phenylpropanoic acid as white needles; m.p. 121°–124.5°; $[\alpha]_D=+28.5°$ (c=1.03, acetone). TLC (silica gel; benzene:acetic acid, 7:3) $R_f=0.33$.

Sodium bicarbonate (10.08 g., 120 mmole) is added to a stirred solution of (R)-2-hydroxy-3-phenylpropanoic acid (9.97 g., 60 mmole) in dimethylformamide (50 ml.) under argon followed by the dropwise addition of a solution of benzyl bromide (7.13 ml., 60 mmole) over one hour. After the addition is completed, the reaction mixture is allowed to stir at room temperature (protected from light). After 26 hours, the dimethylformamide is evaporated. The residue is diluted with water (100 ml.) and extracted with ethyl acetate (1×250 ml., 1×50 ml.). The combined ethyl acetate extract is washed with 5% sodium bicarbonate, water, and brine, dried over sodium sulfate, and evaporated to give 12.78 g. of a pale yellow oil. This material is flash chromatographed in two portions on silica gel (Merck, 320 g.) eluting with hexane:ether (7:3) to give 11.68 g. of (R)-2-hydroxy-3-phenylpropanoic acid, phenylmethyl ester as a colorless oil.

Trifluoromethanesulfonic anhydride (0.84 ml., 5 mmole) is added in rapid drops to a vigorously stirred solution of pyridine (0.44 ml., 5.5 mmole) in dry methylene chloride (40 ml.) at −5° under argon. The resulting thick white slurry is stirred for 5 minutes, then a solution of (R)- 2-hydroxy-3-phenylpropanoic acid, phenylmethyl ester (1.28 g., 5 mmole) in methylene chloride (5 ml.) is added. The reaction mixture is allowed to stir for one hour, gradually warming to 5°, and then is stirred for 2 hours at room temperature. The reaction mixture still contains some unreacted starting material. It is cooled to −10° to −15° and pyridine (0.22 ml., 2.75 mmole) followed by trifluoromethanesulfonic anhydride (0.42 ml., 2.5 mmole) are added. The reaction mixture is stirred for 5 minutes in the cold, and then for 15 minutes at room temperature. The solvent is evaporated and the residue is flash chromatographed on silica (Merck, 100 g. packed in hexane) eluting with 9:1 hexane:ether to give 1.64 g. of (R)-2-[[(trifluoromethyl)sulfonyl]oxy]benzenepropanoic acid, phenylmethyl ester as a colorless oil.

A solution of L-phenylalanine, 1,1-dimethylethyl ester (1.4 g., 6.33 mmole) and diisopropylethylamine (0.81 ml., 4.64 mmole) in dry methylene chloride (5 ml.) is added in one portion to a solution of (R)-2-[[(trifluoromethyl)sulfonyl)oxy]-benzenepropanoic acid, phenylmethyl ester (1.64 g., 4.22 mmole) in methylene chloride (10 ml.) under argon. The reaction mixture is allowed to stir at room temperature overnight. The solvent is evaporated and the residue is taken up into ethyl acetate (200 ml.). This solution is washed with water, 5% sodium bicarbonate, water, and brine, then dried over sodium sulfate, and evaporated to give 2.67 g. of a cloudy oil. Purification by flash chromatography on silica gel (Merck, 235 g.) eluting with 4:1 hexane:ether gives 1.64 g. of (S)-N-[1-[(1,1-dimethylethoxy)carbonyl]-2-phenylethyl] -L-phenylalanine, phenylmethyl ester as a clear colorless oil. An analytical sample is obtained by crystallization from pentane, m.p. 54°–56°; $[\alpha]_D$ =+3.1 (c=1.02, chloroform).

A solution of this phenylmethyl ester product (1.63 g., 3.55 mmole) in ethyl acetate (20 ml.) and 95% ethanol (20 ml.) is stirred with palladium hydroxide on carbon catalyst (325 mg.) under a hydrogen atmosphere for two hours. The catalyst is filtered and washed with 95% ethanol (200 ml.) to dissolve some product that had precipitated. Evaporation of the solvent gives 1.33 g. of yellow solid. Purification by flash chromatography on silica gel (Merck, 90 g., packed in chloroform) eluting with 50:1:1 chloroform:methanol:acetic acid gives 1.06 g. of (S)-N-[1-[(1,1-dimethylethoxy)carbonyl] -2-phenylethyl]-L-phenylalanine.

c)
3-[[N-[(S)-1-Carboxy-2-phenylethyl]-L-phenylalanyl]amino]propanoic acid

Finely powdered β-alanine, phenylmethyl ester, monohydrochloride (598 mg., 2.76 mmole) is added to a solution of the product from part (b) (1.02 g., 2.76 mmole) and diisopropylethylamine (0.48 ml., 2.76 mmole) in tetrahydrofuran (20 ml.) under argon followed by 1-hydroxybenzotriazole hydrate (373 mg., 2.76 mmole). The mixture is cooled to 0°–5°, and a solution of dicyclohexylcarbodiimide (567 mg., 2.76 mmole) in tetrahydrofuran (10 ml.) is added. The reaction mixture is allowed to stir for 3 hours at 0°–5° and then overnight at room temperature. The mixture is diluted with ethyl acetate (50 ml.) and filtered to remove dicyclohexyl urea. The solvent is evaporated and the residue is dissolved in ethyl acetate (100 ml.). The solvent is filtered, diluted with ethyl acetate (50 ml.), washed with water, 5% sodium bicarbonate, water, and brine, dried over sodium sulfate, and evaporated to give 1.46 g. of a colorless semi-solid residue. This material is combined with 0.3 g. from another run and purified by flash chromatography on silica gel (Merck, 135 g.) eluting with hexane:ethyl acetate (3:2) to give 1.41 g. of 3-[[N-[(S)-1-[(dimethylethoxy)carbonyl] -2-phenylethyl]-L-phenylalanyl]amino] propanoic acid, phenylmethyl ester as a colorless oil.

A solution of this phenylmethyl ester product (1.41 g., 2.66 mmole) in 95% ethanol (20 ml.) and water (3 ml.) is stirred with palladium hydroxide on carbon catalyst (280 mg.) under a hydrogen atmosphere for 2 hours. The catalyst is filtered and the solvent is evaporated to yield 1.15 g. of a yellow foam. Flash chromatography on silica gel (Merck, 45 g., packed in chloroform) eluting with 50:1:1 chloroform:methanol:acetic acid yields 1.12 g. of 3-[[N-[(S)-1-[(dimethylethoxy)carbonyl]- 2-phenylethyl]-L-phenylalanyl]amino]propanoic acid as a colorless oil.

A solution of this propanoic acid product (1.06 g., 2.41 mmole) in 1.5N HCl in acetic acid (20 ml.) is stirred at room temperature for 3 hours. Evaporation of the solvent and trituration with ether yields a white solid. This solid is redissolved in 1.5N HCl in acetic acid (25 ml.) and allowed to stir overnight. The solution is filtered and the solvent is evaporated. Acetic acid is added to the residue and evaporated (twice), then the residue is triturated with ether to give 1.01 g. of a powdery white solid. An 850 mg. portion of this material is recrystallized twice from acetonitrile-water to give 647 mg. of 3-[[N-[(S)-1-carboxy-2-phenylethyl]-L-phenylalanyl] amino]propanoic acid as a white solid; 219°–220.5° (dec.); $[\alpha]_D$=−31.4° (c =0.99, dimethylformamide). TLC(silica gel; chloroform:methanol: acetic acid, 10:1:1) $R_f$=0.27.

Anal. calc'd. for $C_{21}H_{24}N_2O_5$: C, 65.61; H, 6.29; N, 7.29
Found: C, 65.30; H, 6.28; N, 7.42.

EXAMPLE 79

7-[[N-[(S)-1-Carboxy-2-phenylethyl]-L-phenylalanyl]amino] heptanoic acid

A solution of (S)-N-[1-[(1,1-dimethylethoxy)carbonyl] -2-phenylethyl]-L-phenylalanine, phenylmethyl ester (6.66 g., 14.5 mmole, prepared as described in Example 78) and anisole (1 ml.) in methylene chloride (43 ml.) and trifluoroacetic acid (100 ml.) is allowed to stir under argon for 6 hours. The solvent is evaporated and the residue is twice taken up into toluene and evaporated to dryness. Trituration of the residue with ether gives 5.91 g. of (S)-N-(1-carboxy-2-phenylethyl)-L-phenylalanine, phenylmethyl ester as a white solid; m.p. 185.5°–187.5°.

Solid dicyclohexylcarbodiimide (722 mg., 3.5 mmole) is added in one portion to a solution of the above phenylmethyl ester product (1.41 g., 3.5 mmole), 7-aminoheptanoic acid, phenylmethyl ester, monohydrochloride [951 mg., 3.5 mmole, prepared as described by Smith et al., J. Med. Chem., 20, 1292 (1977)], 1-hydroxybenzotriazole hydrate (473 mg., 3.5 mmole), and diisopropylethylamine (0.61 ml., 3.5 mmole) in dimethylformamide (35 ml.) at 0°–5° under argon. The reaction mixture is allowed to stir, warming gradually to room temperature, overnight. The dicyclohexyl urea is filtered and washed with ethyl acetate. The filtrate is evaporated and the residue is taken up into ethyl acetate (175 ml.). This solution is filtered, washed with 10% potassium bisulfate, water, 5% sodium bicarbonate, water, and brine, dried over sodium sulfate, and evaporated to give 2.48 g. of a pale yellow residue. This residue is dissolved in a minimal volume of chloroform, adsorbed onto Merck silica gel, dried, and applied to a column of the same silica gel (185 g.) and flash chromatographed eluting with 7:3 hexane:ether to give 1.64 g. of 7-[[N-[(S)-1-[(phenylmethoxy)carbonyl]-2-phenylethyl] -L-phenylalanyl]amino]heptanoic acid, phenylmethyl ester as a colorless oil.

A solution of this phenylmethyl ester product (1.64 g., 2.64 mmole) in 95% ethanol (20 ml.) and water (3 ml.) is stirred with palladium hydroxide on carbon catalyst (320 mg.) under a hydrogen atmosphere. After 10 minutes, a white precipitate begins to separate. Two additional portions of 95% ethanol (20 ml.) are added, however, the precipitate fails to redissolve. After 5 hours, the catalyst is filtered and extracted with dimethylformamide (5×20 ml.). The combined filtrate is evaporated to dryness to give 1.13 g., of a yellow solid residue. The material is dissolved with gentle warming in 2% sodium bicarbonate (200 ml.). The solution is washed with ethyl acetate (2×30 ml.) and ether (3×30 ml.), decolorized with charcoal, and then adjusted to pH of about 6 with 1N HCl. The white precipitate that separates is collected and triturated with acetonitrile to give 494 mg. of solid. The filtrate is concentrated to approximately 50 ml. and re-acidified to a pH of about 5 with 1N HCl affording an additional 417 mg. of solid. The two crops of solid are combined and triturated with acetonitrile to give 895 mg. of white solid 7-[[N-[ (S)-1-carboxy-2-phenylethyl]-L-phenylalanyl]amino]-heptanoic acid; m.p. 198.5°–199° (sinters at 185°); $[\alpha]_D$=33.3° (c=1, dimethylformamide). TLC (silica gel; chloroform:methanol:acetic acid, 20:1:1) $R_f$=0.22 (trace at origin). TLC (silica gel; ethyl acetate:pyridine:acetic acid:water, 180:20:6:11) $R_f$=0.42 (trace at origin).

Anal. calc'd. for $C_{25}H_{32}N_2O_5$: C, 68.16; H, 7.32; N, 6.36 Found: C, 67.87; H, 7.26; N, 6.21.

EXAMPLE 80

N-[N-[(S)-1-Carboxy-2-phenylethyl]-L-phenylalanyl]-L-leucine

Solid dicyclohexylcarbodiimide (722 mg., 3.5 mmole) is added in one portion to a solution of (S)-N-(1-carboxy-2-phenylethyl)-L-phenylalanine, phenylmethyl ester (1.41 g., 3.5 mmole), prepared as described in Example 79, L-leucine, phenylmethyl ester, p-toluenesulfonic acid salt (1.38 g., 3.5 mmole), 1-hydroxybenzotriazole hydrate (473 mg., 3.5 mmole) and diisopropylethylamine (0.61 ml., 3.5 mmole) in dimethylformamide (70 ml.) at 0°–5° under argon. The reaction mixture is allowed to stir, gradually warming to room temperature, overnight. The dicyclohexyl urea is filtered and the filtrate is evaporated. The residue is dissolved in ethyl acetate (200 ml.) and this solution is washed with 10% potassium bisulfate, water, 5% sodium bicarbonate, water, and brine, then dried over sodium sulfate, and evaporated to give 2.2 g. of an off-white semi-solid residue. This residue is dissolved in a minimal amount of chloroform, adsorbed onto Merck silica gel, dried, and applied to a column of the same silica gel (165 g.). Flash chromatography eluting with 4:1 hexane:ethyl acetate, yields 1.85 g. of N-[N-[(S)-1-[(phenylmethoxy)carbonyl] -2-phenylethyl]-L-phenylalanyl]-L-leucine, phenylmethyl ester as a colorless oil.

A solution of this phenylmethyl ester product (1.85 g., 3.05 mmole) in 95% ethanol (40 ml.) and water (3 ml.) is stirred with palladium hydroxide on carbon catalyst (370 mg.) under a hydrogen atmosphere for 2 hours. The catalyst is filtered and the solvent is evaporated. The still-moist residue is recrystallized from acetonitrile-water to give 1.15 g. of white solid N-[N-[(S)-1-carboxy- 2-phenylethyl]-L-phenylalanyl]-L-leucine; m.p. 185°–186.5°; $[\alpha]_D$ =48.0° (c=0.99, dimethylformamide). TLC (silica gel; chloroform:methanol: acetic acid, 15:1:1) $R_f$=0.40 (trace at origin). TLC (silica gel; ethyl acetate:pyridine:acetic acid:water, 180:20:6:11) $R_f$=0.28 (trace at origin).

Anal. calc'd. for $C_{24}H_{30}N_2O_5 \cdot 0.6\ H_2O$: C, 65.92; H, 7.19; N, 6.40 Found: C, 65.90; H, 7.34; N, 6.46;

EXAMPLE 81

(trans)(R,R)-N-[N-[(2-Carboxycyclohexyl)carbonyl]-L-phenylalanyl] -L-leucine

A sample of (trans)(R,R)-1,2-cyclohexanedicarboxylic acid (0.6 g., 3.5 mmole, prepared as set forth in Example 27(a) of United States Patent 4,499,079) is suspended in acetyl chloride (7 ml.), flushed with nitrogen, and heated under reflux for 2 hours. The resulting clear, yellow solution is concentrated in vacuo, benzene (5 ml.) is added, the mixture is again concentrated. The residue is taken up in tetrahydrofuran (6 ml.), treated with benzyl alcohol (0.54 ml., 1.5 equivalents) and flushed with argon. Diisopropylethylamine (0.22 ml., 1.3 mmole) is then added (mixture turns pink), and the solution is stirred overnight at room temperature. The solvent is removed in vacuo, and the residue is poured into saturated sodium bicarbonate (80 ml.). After washing with ether (2×25 ml.), the aqueous solution is acidified to a pH of about 2 with concentrated HCl and extracted with ethyl acetate (3×20 ml.). These extracts are combined, washed with water and brine (20 ml. each), dried over sodium sulfate, and concentrated in vacuo to give 0.58 g. (trans)(R,R)-1,2-cyclohexanedicarboxylic acid, monophenylmethyl ester as a clear, light brown oil.

A suspension of this monophenylmethyl ester (0.5 g., 1.9 mmole), N-(L-phenylalanyl)-L-leucine, phenylmethyl ester, monohydrochloride (0.78 g., 1.9 mmole), and hydroxybenzotriazole hydrate (0.26 g., 1.9 mmole) in tetrahydrofuran (10 ml.) is flushed with nitrogen and treated with diisopropylethylamine (0.66 ml., 3.8 mmole). The mixture is chilled in an ice/methanol bath, and a solution of dicyclohexylcarbodiimide (0.39 g., 1.9 mmole) in tetrahydrofuran (5 ml.) is added over 10 minutes. After stirring overnight while warming to room temperature, ethyl acetate (20 ml.) is added and the mixture is filtered to remove dicyclohexyl urea. The filtrate is concentrated in vacuo, taken up in ethyl acetate (50 ml.), washed with 10% potassium bisulfate (twice), saturated sodium carbonate (twice), water, and brine (25 ml. each), and dried over sodium sulfate. Concentrating in vacuo gives a gummy white solid which is adsorbed onto silica gel (Baker, 5 g. of 60–200 mesh) and applied to a column of silica gel (Merck, 80 g. of 230–400 mesh). Eluting with hexane/ethyl acetate (20:7) and concentrating the product containing fractions in vacuo gives 0.74 g. of (trans)(R,R)-N-[N-[[2-[(phenylmethoxy)carbonyl] cyclohexyl]carbonyl] -L-phenylalanyl]- L-leucine, phenylmethyl ester as white foamy amorphous solid.

An argon flushed solution of this phenylmethyl ester product (0.71 g., 1.2 mmole) in 95% ethanol (30 ml.) is treated with 10% palladium on carbon catalyst (70 mg.). The mixture is hydrogenated under a positive pressure of hydrogen, with thorough stirring, overnight at room temperature. After filtering the mixture through Celite, the filtrate is concentrated in vacuo to give 0.41 g. of a light brown solid.

An analytical sample is prepared by recrystallization of 0.33 g. from ethyl acetate/hexane to yield 0.243 g. of white solid (trans)(R,R)-N-[ N-[N-[(2-carboxycyclohexyl)carbonyl]-L-phenylalanyl]-L-leucine; m.p. 183.5°–185°. $[\alpha]_D = -39.8°$ (C =1.0, methanol). TLC (silica gel; toluene:acetic acid, 9:2) $R_f$=0.30.

Anal. calc'd. for $C_{23}H_{32}N_2O_6 \cdot 0.35$ $H_2O$: C, 62.95; H, 7.56; N, 6.39 Found: C, 62.95; H, 7.58; N, 6.15.

EXAMPLE 82

N-[N-[2-(Mercaptomethyl)-1-oxo-3-phenylpropyl]glycyl] -L-arginine

As described in Example 35 of Australian Patent No. 537,592, a solution N-[2-[(acetylthio)methyl] -1-oxo-3-phenylpropyl]glycine in tetrahydrofuran is treated with triethylamine, cooled to 0°, and then treated with ethyl chloroformate. After the mixture is stirred at 0° for 40 minutes it is filtered into a solution of arginine and worked up to yield N-[N-[2-[(acetylthio)methyl]-1-oxo-3-phenylpropyl] glycyl]-L-arginine.

This acetylthiomethyl product is treated with concentrated ammonium hydroxide as described in Example 35 of Australian patent 537,592 to yield N-[N-[2-(mercaptomethyl)-1-oxo-3-phenylpropyl]glycyl] -L-arginine; m.p. 120°–137°.

Anal. calc'd. for $C_{18}H_{27}N_5O_4S \cdot 1.75$ $H_2O$: C, 49.02; H, 6.97; N, 15.88; S, 7.27 Found: C, 48.89; H, 6.67; N, 16.17; S, 7.28.

EXAMPLE 83

The in vitro neutral endopeptidase activity is determined using a fluorometric assay procedure. The assay is based upon the cleavage of the fluorescent dansylated tripeptide Dns-Gly-Phe-Arg to form Dns-Gly. The latter is extracted from the acidified mixture by ethyl acetate and is strongly fluorescent.

The incubation mixture employed for the assay contains the substance Dns-Gly-Phe-Arg (0.5 mM), tris(hydroxymethyl)aminomethane -HCl buffer (pH 7.5, 50 mM), an enzyme preparation in 0.05% Triton X-100, and water or inhibitor diluted to a final volume of 0.25 ml. The enzyme preparation is purified from rat kidney according to the procedure described by Almenoff et al. in Biochemistry Vol. 22, p. 590–599 (1983). The inhibitor is preincubated for 10 minutes with the enzyme preparation and buffer before the reaction is initiated by the addition of the substrate. Incubation is carried out at 37° for 30 minutes and the reaction is stopped by the addition of 0.25 ml. 1N HCl and extraction of the Dns-Gly product into 1.5 ml. of ethyl acetate. Relative fluorescent intensity (RFI) of the ethyl acetate extract is measured using a Ferrand Spectofluorometer at excitation and emission wavelengths of 342 and 508 nm., respectively, corrected for the RFI of a zero-time control, and compared with assays lacking inhibitor.

Runs are made at different concentrations of test compound and by use of a mathematical model the $IC_{50}$ is determined. The $IC_{50}$ is the concentration of test compound that inhibits activity of the enzyme by 50%.

| Compound tested | $IC_{50}(\mu M)$ | Compound tested | $IC_{50}(\mu M)$ |
|---|---|---|---|
| Example 1 | 0.0066 | Example 31 | 0.0053 |
| 2 | 0.380 | 32 | 0.0089 |
| 3 | 0.720 | 33 | 0.009 |
| 4 | 0.290 | 34 | 0.012 |
| 5 | 0.020 | 35 | 0.0069 |
| 6 | 0.013 | 36 | 0.072 |
| 7 | 0.054 | 37 | 0.016 |
| 8 | 0.280 | 38 | 0.087 |
| 9 | 0.0039 | 39 | 0.015 |
| 10 | 0.510 | 40 | 0.190 |
| 11 | 0.170 | 41 | 0.730 |
| 12 | 0.0033 | 42 | 0.036 |
| 13 | 0.0022 | 43 | 0.064 |
| 14 | 0.091 | 44 | 0.220 |
| 15 | 0.030 | 45 | 0.0089 |
| 16 | 0.370 | 46 | 0.006 |
| 17 | 0.014 | 47 | 0.018 |
| 18 | 0.069 | 48 | 0.052 |
| 19 | 0.110 | 49 | 0.022 |
| 20 | 0.021 | 50 | 0.059 |
| 21 | 0.280 | 51 | 0.020 |
| 22 | 0.0067 | 52 | 0.026 |
| 23 | 0.049 | 53 | 0.076 |
| 24 | 0.047 | 54 | 0.680 |
| 25 | 0.120 | 55 | 0.530 |
| 26 | 0.032 | 56 | 0.023 |
| 27 | 0.0057 | 57 | 0.028 |
| 28 | 0.0078 | 58 | 0.095 |
| 29 | 0.017 | 59 | 0.330 |
| 30 | 0.020 | 60 | 0.031 |
| Example 61 | 0.120 | Example 72 | 0.0038 |
| 62 | 0.740 | 73 | 0.0072 |
| 63 | 0.310 | 74 | 0.950 |
| 64 | 0.006 | 75 | 0.040 |
| 65 | 0.062 | 76 | 1.200 |
| 66 | 0.078 | 77 | 2.200 |
| 67 | 0.970 | 78 | 0.013 |
| 68 | 1.200 | 79 | 0.940 |
| 69 | 0.012 | 80 | 0.330 |
| 70 | 0.0031 | 81 | 1.200 |
| 71 | 0.014 | 82 | 0.015 |

EXAMPLE 84

The depressor response to test compounds in conscious mineralocorticoid hypertensive rats is determined according to the following procedure.

Male Sprague-Dawley rats (approximately 150 grams) are anesthetized with sodium pentobarbital and indwelling vascular catheters are implanted in the abdominal aorta and vena cava using the methods of Weeks et al., Biological Medicine, Vol. 104, p. 646 (1960).

Before closing the abdominal incision, a pellet containing 100 mg. of deoxycorticosterone acetate (DOCA) is placed in the peritoneal cavity. DOCA is released from the pellet at a constant rate for 21 days.

The rats are housed individually and given saline (0.9% sodium chloride) to drink and fed normal rat chow for the next 3 to 4 weeks. Afterwards, the catheters are opened and mean arterial pressure (MAP) is measured via a Statham pressure transducer and a strip chart recorder. Patency of the arterial catheter is maintained by the infusion of saline from a pressurized reservoir at approximately 10 to 15 µl/min.

Following 2 hours of acclimation, the test compound is injected intravenously. Each dose is delivered as 1.0 ml./kg. +0.03 ml. (an amount sufficient to fill the void volume of the catheter). The MAP is recorded for at least 4 hours.

| Compound tested | Change in MAI (mm. of Hg.) | Dose (µmole/kg.) |
|---|---|---|
| Example 1 | −65 ± 14 | 300 |
| 35 | −56 ± 3 | 300 |
| 39 | −55 ± 4 | 300 |
| 52 | −41 ± 8 | 300 |

| Compound tested | Change in MAI (mm. of Hg.) | Dose (μmole/kg.) |
|---|---|---|
| 64 | −44 ± 5 | 300 |

EXAMPLE 85

The capacity of the test compounds to enhance the depressor response to exogenous ANP 99–126 in conscious spontaneously hypertensive rats (SHR) is determined according to the following procedure.

Indwelling vascular catheters are implanted in the abdominal aorta and vena cava of male SHR rats using the methods of Weeks et al. The rat is allowed at least one week recovery time. On the day of the experiment, the aortic catheter is opened and attached to a Statham transducer via a 3-way stream divider. This system allows for a continuous slow infusion of saline (approximately 10 to 15 μl/min.) from a pressurized reservoir to maintain patency of the arterial catheter. Mean arterial pressure (MAP) is continuously monitored on a strip-chart recorder.

Two hours after beginning the blood pressure measurements, the test compound (or the vehicle used to dissolve the compound) is injected intravenously (1.0 ml./kg.) and flushed in with 0.3 ml. of saline. 30 minutes later, a challenge of 3 nmole/kg. of ANP 99–126 is delivered (1.0 ml./kg. +0.3 ml. saline flush). Sufficient time is allowed after the ANP 99–126 injection to observe the maximal depressor response and a 50% recovery.

MAP is determined before ANP 99–126 administration and at 5 minute intervals until the blood pressure recovers by at least 50%. A mathematical model is used to calculate the area under the curve which extends from the time that the MAP falls to 50% of the maximal depressor response to the time of 50% recovery. Results are plotted as the log dose of inhibitor vs. the area under the curve.

The $ED_{600}$ is the dose required to increase the area under the blood pressure over time curve for exogenous ANP to 600 mm Hg. X minute.

| Test compound | $ED_{600}$ (μmole/kg.) |
|---|---|
| Example 1 | 22.8 |
| 35 | 9.2 |
| 36 | 8.22 |
| 52 | 15.5 |
| 66 | 2.93 |

EXAMPLE 86

The renal function following administration of test compounds is determined according to the following procedure.

A catheter is contructed as follows. Pieces of 18 gauge metal tubing (about ¼ inch in length) are inserted into two lengths of microbore Tygon tubing (0.04 inch inner diameter ×0.07 inch outer diameter). A short segment of Tygon tubing of larger diameter (0.104 inch inner diameter x 0.144 inch outer diameter) is sealed around both metal fittings. This end is to be implanted in the bladder. In order to keep the tip from becoming plugged by particulate matter, 4 holes are punched along its length.

To implant the catheters, male rats are anesthetized with sodium pentobarbital and the urinary bladder is exposed via a midline abdominal incision. A small slit is made in the dome of the urinary bladder and the tip of the catheter is inserted into the lumen. The catheter is secured by a silk suture and the free ends are routed subcutaneously to the base of the skull. The tubing is protected by a metal spring and the end of the spring is anchored to the skull with dental acrylic. The catheter tubing is filled with 0.2% nitrofurazone solution and tightly plugged. The rats are left undisturbed for 3 to 5 days before the tubes are opened. Urine is gently withdrawn from the bladder by a withdrawal pump attached to one of the tubes. The other tube serves as a vent to allow air to enter the bladder so that a suction could not be created. The opening of the intake tube is protected by a Millipore filter so that foreign particles are removed before the air reaches the bladder.

During the course of the experiment, urine is collected in tared containers at specified intervals. Urine volume is determined gravimetrically (1 gram =1 ml.) and the rate of flow is calculated from the total volume/time of collection (ml./min.). Sodium concentrations are measured using a Nova-1 Ion Selective Electrode Analyzer. Electrolyte excretion rates (μ Eq./min.) are calculated by multiplying the ion concentration (μ Eq./ml.) by the urine flow (mi./min.).

Urine is collected twice at 20 minute intervals prior to administration of test compound. The compound is administered intravenously and urine is collected at 20 minute intervals over the next 4 hours.

According to this procedure administration of the compound of Example 52 at an intravenous dose of 30 mg./kg. plus 3 mg./kg./min. for 20 minutes caused a 2.6-fold increase in the rate of sodium excretion in conscious spontaneously hypertensive rats. The compound of Example 1 at an intravenous dose of 100 mg./kg. caused a 2.4-fold increase in sodium excretion.

What is claimed is:

1. The method of producing diuresis, natriuresis, and lowering blood pressure in a mammalian host which comprises administering to said host an effective amount of a neutral endopeptidase inhibitor of the formula

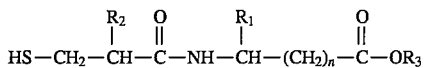

wherein:

$R_2$ is benzyl;

$R_1$ is hydrogen or benzyl;

n is an integer from 1 to 9; and $R_3$ is hydrogen or a pharmaceutically acceptable salt forming ion.

2. The method of claim 1 wherein:

$R_1$ is hydrogen.

3. The method of producing diuresis, natriuresis, and lowering blood pressure in a mammalian host which comprises administering to said host an effective amount of a neutral endopeptidase inhibitor of the formula

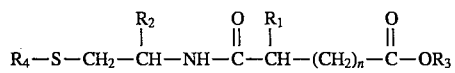

wherein:

$R_4$ is hydrogen or

$R_1$ and $R_2$ are independently selected from the group consisting of hydrogen, lower alkyl, $-(CH_2)_q$-cycloalkyl,

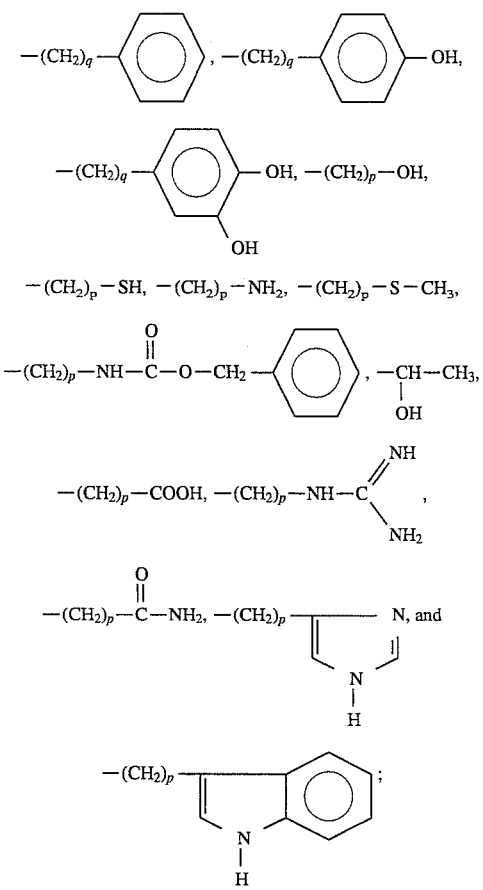

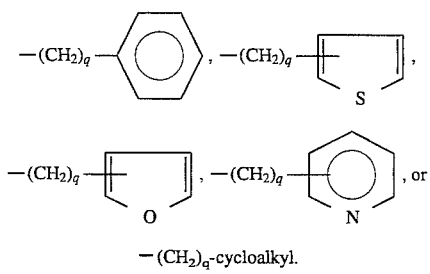

q is zero or an integer from 1 to 4;

p is an integer from 1 to 4;

n is zero or an integer from 1 to 15;

$R_3$ is hydrogen, lower alkyl, benzyl, benzhydryl, or a pharmaceutically acceptable salt forming ion; and $R_6$ is lower alkyl,

4. The method of claim 3 wherein:

$R_4$ is hydrogen;

$R_2$ is benzyl;

$R_1$ is hydrogen;

n is zero or an integer from 1 to 5; and $R_3$ is hydrogen or a pharmaceutically acceptable salt forming ion.

5. The method of producing, diuresis, natriuresis, and lowering blood pressure in a mammalian host which comprises administering to said host an effective amount of a neutral endopeptidase inhibitor of the formula

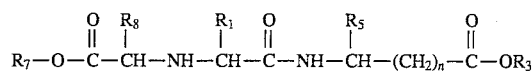

wherein:

$R_1$ and $R_5$ are independently selected from the group consisting of hydrogen, lower alkyl,

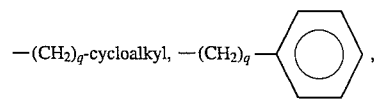

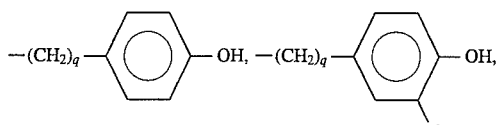

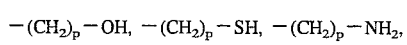

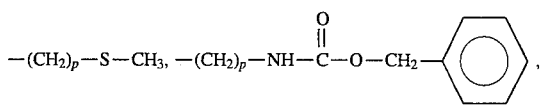

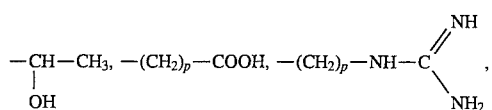

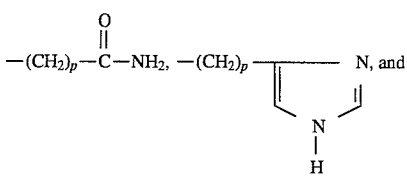

$R_8$ is hydrogen, lower alkyl,

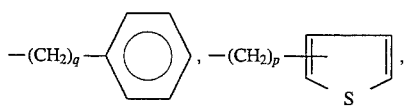

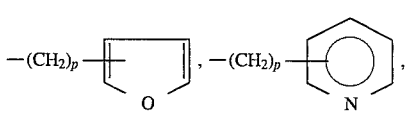

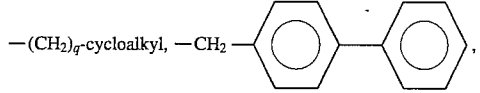

or a 1- or 2-naphthylalkylene of the formula

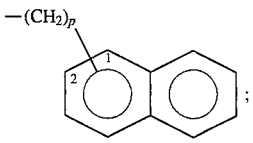

q is zero or an integer from 1 to 4;

p is an integer from 1 to 4;

n is zero or an integer from 1 to 15; and $R_3$ and $R_7$ are independently selected from the group consisting of hdrogen, lower alkyl, benzyl, benzhydryl, and a pharmaceutically acceptable salt forming ion.

6. The method of claim 5 wherein:

$R_1$ and $R_8$ are both benzyl;

$R_5$ is hydrogen and n is zero or an integer from 1 to 5 or $R_5$ is straight or branched chain lower alkyl of 1 to 4 carbons and n is zero; and $R_3$ and $R_7$ are both hydrogen or both a pharmaceutically acceptable salt forming ion.

7. The method of producing diuresis, natriuresis, and lowering blood pressure in a mammalian host which comprises administering to said host an effective amount of a neutral endopeptidase inhibitor of the formula

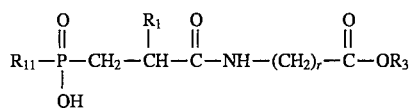

wherein:

$R_1$ is hydrogen, lower alkyl,

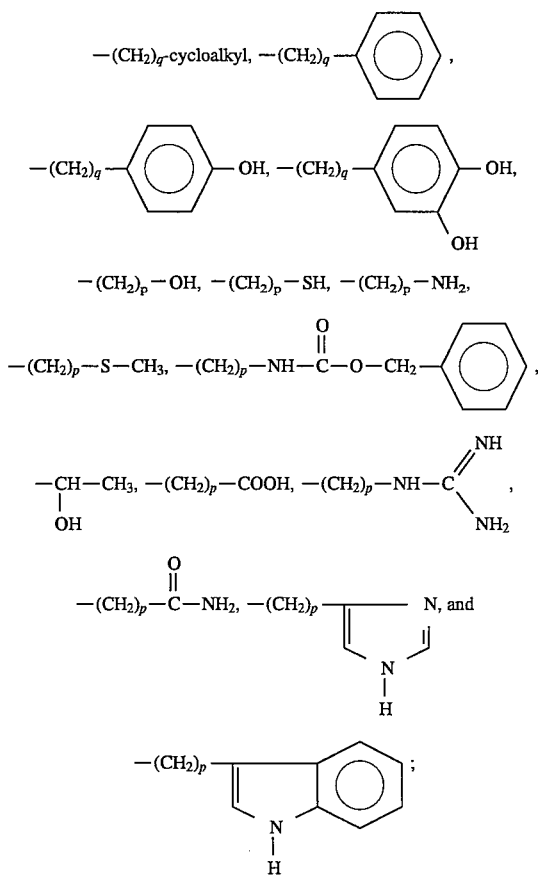

$R_{11}$ is lower alkyl,

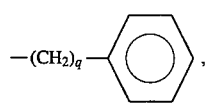

hydroxy, —O(—lower alkyl —(CH$_2$)$_q$-cycloalkyl

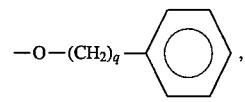

or —O—(CH$_2$)$_q$-cycloalkyl;

$R_6$ is lower alkyl,

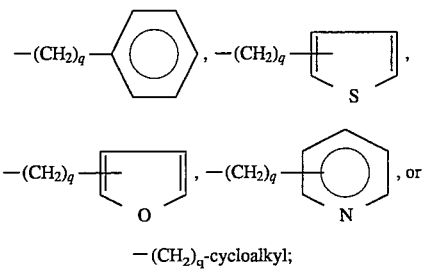

—(CH$_2$)$_q$-cycloalkyl;

q is zero or an integer from 1 to 4;

p is an integer from 1 to 4;

r is an integer from 2 to 4; and $R_3$ is hydrogen, lower alkyl, benzyl, benzhydryl, or a pharmaceutically acceptable salt forming ion.

8. The method of claim 7 wherein:

$R_{11}$ is hydroxy;

$R_1$ is benzyl;

r is two; and $R_3$ is hydrogen or a pharmaceutically acceptable salt forming ion.

9. The method of producing diuresis, natriuresis, and lowering blood pressure in a mammalian host which comprises administering to said host an effective amount of the neutral endopeptidase inhibitor N-(α-L-rhamnopyranosyloxy-hydroxy- phosphinyl)-L-leucyl-L-tryptophan.

10. The method of producing diuresis, natriuresis, and lowering blood pressure in a mammalian host which comprises administering to said host an effective amount of neutral endopeptidase inhibitor of the formula

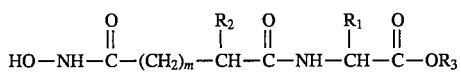

wherein:

$R_1$ and $R_2$ are independently selected from the group consisting of hydrogen, lower alkyl,

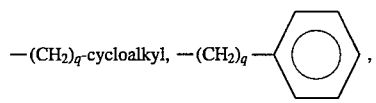

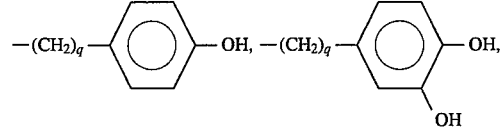

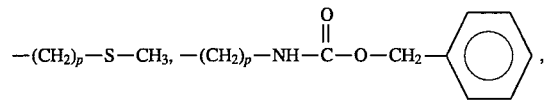

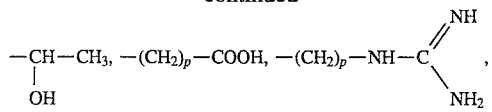
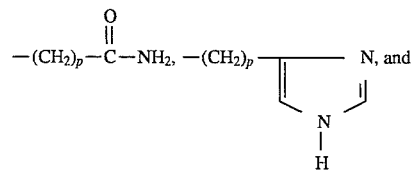
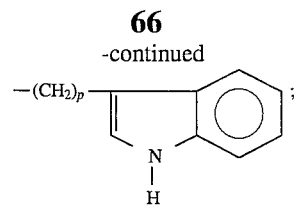
m is zero or one;
q is zero or an integer from 1 to 4;
p is an integer from 1 to 4; and
$R_3$ is hydrogen, lower alkyl, benzyl, benzhydryl, or a pharmaceutically acceptable salt forming ion.
* * * * *